United States Patent
Guegler et al.

(10) Patent No.: US 6,579,709 B2
(45) Date of Patent: Jun. 17, 2003

(54) ISOLATED HUMAN KINASE PROTEINS, NUCLEIC ACID MOLECULES ENCODING HUMAN KINASE PROTEINS, AND USES THEREOF

(75) Inventors: Karl Guegler, Menlo Park, CA (US); Ellen M. Beasley, Darnestown, MD (US); Valentina Di Francesco, Rockville, MD (US)

(73) Assignee: Applera Corporation, Norwalk, CT (US)

(*) Notice: Subject to any disclaimer, the term of this patent is extended or adjusted under 35 U.S.C. 154(b) by 0 days.

(21) Appl. No.: 09/964,469

(22) Filed: Sep. 28, 2001

(65) Prior Publication Data

US 2002/0034803 A1 Mar. 21, 2002

Related U.S. Application Data

(62) Division of application No. 09/738,894, filed on Dec. 18, 2000, now Pat. No. 6,331,423.
(60) Provisional application No. 60/208,331, filed on Jun. 1, 2000.

(51) Int. Cl.[7] .......................... C12N 9/12; C12N 15/00; C12N 1/20; A61K 38/51; C07K 1/00
(52) U.S. Cl. .................. 435/194; 435/320.1; 435/325; 435/252.3; 435/6; 424/94.5; 530/350
(58) Field of Search ............................... 435/194, 320.1, 435/325, 252.3; 530/350; 424/94.5

(56) References Cited

U.S. PATENT DOCUMENTS 5,532,151 A  7/1996 Chantry et al. ............. 436/194

FOREIGN PATENT DOCUMENTS

WO   WO 01/38503 A   5/2001
WO   WO 01/68869 A   9/2001

OTHER PUBLICATIONS

Wong et al., Mol. Vis., 4, 27, 1998.*
International Search Report dated March 26, 2002, whole document.
Weiss, Ellen R et al., "The cloning of GRK7, a candidate cone opsin kinase, from cone and rod–dominant mammalian retinas.": MOLECULAR VISION, SN, Atlanta, US, vol. 4, p. 27, Dec. 08, 1998.
–& DATABASE EMBL 'online!' Accession No. AF063016; Dec. 11, 1998.
Benovic, Jefferey, L., et al., "Molecule cloning and expression of GRK6: A new member of the G protein–coupled receptor kinase family." Journal of Biological Chemistry, American Society of Biological Chemists, Baltimore, MD, US vol. 268, No. 26, pp. 19521–19527, 1993.
Hisatomi, O et al., "A novel subtype of G–protein–coupled receptor kinase, GRK7, in teleost cone photoreceptors." Febs Letters, Elsevier Science Publishers, Amersterdam, ML, vol. 424, No. 3, pp. 159–164; Mar. 13, 1998.
DATABASE EMBL 'online!' Accession No. AC068693; May 07, 2000.

* cited by examiner

*Primary Examiner*—M. Monshipouri
(74) *Attorney, Agent, or Firm*—Celera Genomics; Justin Karjala

(57) ABSTRACT

The present invention provides amino acid sequences of peptides that are encoded by genes within the human genome, the kinase peptides of the present invention. The present invention specifically provides isolated peptide and nucleic acid molecules, methods of identifying orthologs and paralogs of the kinase peptides, and methods of identifying modulators of the kinase peptides.

4 Claims, 27 Drawing Sheets

```
   1 ATGGTGGACA TGGGGCCCT GGATAACCTG ATCGCAAGA    TACTT
  51 G AGGCC  G AAGC CTCGG ACTGGACAG CAAAGA    TAGC CC CC
 101 GGCCTAG C  GGCCCTGCCC GGGCTG AGG GCTGCG GA G CC CCAG
 151 AAGCTGTCCC TGAACTTCCA CAG CTGTGT GAGCAGCA   C AT C TCG
 201 CCGCCTCTTC CGTGACTTCC TAGCCACAGT GCCCACGTT  CGCAAGGCCC
 251 CAACCTT CT ACAGGACGTG CAGAACTGGG AGCTGG GGA GGAGGGACC
 301 ACCAAAGACA GCCCGCTGCA GGGCTGGTC GCCACT T  C AGTGCCC
 351 TGCCCCGGGG AACCCGCAAC CCTTCCTCAG CCAGGC  TG C TACCAAGT
 401 GCCAAGCAGC CACCACTGAG GAAGACCGAC TGGCTGCAGT GACGCTGGCC
 451 AAGGCTGAGG CCATGGCTTT CTTGCAAGAG CAGCCCTTTA AGGATTCGT
 501 GACCAGCGCC TTCTACGACA AGTTTCTGCA GTGGAAACTC TTCGAGATGC
 551 AACCAGTGTC AGACAACTAC TTCACTGAGT TCAGAGTCCT GGGGAAAGGT
 601 GGTTTTGGGG AGGTATGTGC CGTCCAGGTG AAAACA  T  GGAAGATGTA
 651 TGCCTGTAAG AAACTGGACA AGAAGCGGCT GAAGAAGAAA GGTGGCGAGA
 701 AGATGGCTCT CTTGGAAAAG CAAATC TGG AGAAGGT A  CAGCCCTTTC
 751 ATTGTCTCTC TGGCCTATGC CTTTGAGAGC AACACCCATC TCTGCCTTGT
 801 CATGAGCCTG ATCAATGGGG GAGACCTCAA GTTCCACAT  TACAACGTGG
 851 GCACGCGTGG CCTGGACATG AGCCGGCTCA TCTTTTAC C GGCCCAGATA
 901 GCCTGTGGGA TGCTGCACCT CCATGAACTC GGCATCGTCT ATCGGGACAT
 951 GAAGCCTGAG AATGTGCTTC TGGATGACCT CGGCAACTGC AGGTTATCTG
1001 ACCTGGGGCT GGCCGTGGAG ATGAAGGGTG GCAAGCC AT CACCCAGAGG
1051 GCTGGAACCA ATGGTTACAT GGCTCCTGAG ATCCTAAT G GAAAGGTAAG
1101 TTATTCCTAT CCTGTGGACT GGTTTGCCAT GGCATCCA   ATTTATGAAA
1151 TGGTTGCTGG ACGAACACCA TTCAAAGATT ACAAGGAAAA GGTCAGTAAA
1201 GAGGATCTGA AGCAAAGAAC TCTGCAAGAC GAGGTCAAAT TCCAGCATGA
1251 TAACTTCACA GAGGAAGCAA AAGATATTT  CAGGCTCTTC TTGGCTAAGA
1301 AACCAGAGCA ACGCTTAGGA ACCACAGAAA AGTC GAT A  TCCCAGGAAA
1351 CATCATTTCT TTAAAACGAT CAACTTT C  CGCCTGGAAG CTGGCCTAAT
1401 TGAACCCCCA TTTCTGCCAG ACCCTTCAGT GGTTTAT C  AAAGACATCC
1451 CTGAAATTGA TGATTTCTCT GAGGTTCCGG GGGTGGAAT  TGATGACAAA
1501 GATAAGCAGT TCTTCAAAAA CTTTGCCGACA GGT CTG TTC CTATAGCATG
1551 GCAGGAAGAA ATTATAGAAA CGGGACTGTT TGAGGAACTG AATGACCCCA
1601 ACAGACCTAC GGGTTGTGAG GAGGGTAATT CATCCAAGTC TGGCGTGTGT
1651 TTGTTATTGT AA (SEQ ID NO:1)
```

FEATURES:
Start Codon: 1
Stop Codon: 1660
3'UTR: 1663

Homologous proteins:
Top BLAST Hits

|  | Score | E |
|---|---|---|
| gi\|4001826\|gb\|AAC95001.1\| (AF063016) G protein-coupled receptor... | 961 | 0.0 |
| gi\|3061335\|dbj\|BAA25670.1\| (AB009568) OlGRK-C [Oryzias latipes] | 659 | 0.0 |
| gi\|992673\|gb\|AAC50410.1\| (U33168) G protein-coupled receptor ki... | 499 | e-140 |
| gi\|6166188\|sp\|P32298\|GRK4_HUMAN G PROTEIN-COUPLED RECEPTOR KINA... | 499 | e-140 |
| gi\|4506529\|ref\|NP_002920.1\| rhodopsin kinase [Homo sapiens] >gi\|... | 491 | e-137 |
| gi\|132637\|sp\|P28327\|RK_BOVIN RHODOPSIN KINASE (RK) >gi\|108911\|p... | 490 | e-137 |
| gi\|3005018\|gb\|AAC09274.1\| (AF040752) G protein-coupled receptor... | 489 | e-137 |
| gi\|3005016\|gb\|AAC09273.1\| (AF040751) G protein-coupled receptor... | 489 | e-137 |
| gi\|992674\|gb\|AAC50411.1\| (U33168) G protein-coupled receptor ki... | 487 | e-136 |
| gi\|1770422\|emb\|CAA66802.1\| (X98118) G protein-coupled receptor ... | 486 | e-136 |
| gi\|971259\|gb\|AAC50408.1\| (U33056) G protein-coupled receptor ki... | 486 | e-136 |
| gi\|3005005\|gb\|AAC09270.1\| (AF040749) G protein-coupled receptor... | 485 | e-136 |

FIGURE 1A

BLAST to dbEST:

```
                                                    Score     E
gi|10964566 /dataset=dbest /taxon=96...               62    4e-07
gi|10141448 /dataset=dbest /taxon=96...               62    4e-07
gi|2899516  /dataset=dbest /taxon=9606 ...            62    4e-07
gi|2237572  /dataset=dbest /taxon=9606 ...            62    4e-07
gi|4703322  /dataset=dbest /taxon=9606 ...            62    4e-07
gi|10216415 /dataset=dbest /taxon=96...               58    7e-06
gi|4074280  /dataset=dbest /taxon=9606 ...            58    7e-06
```

EXPRESSION INFORMATION FOR MODULATORY USE:
library source:
Expression information from BLAST dbEST hits:
gi|10964566  Skin
gi|10141448  Skin
gi|2899516   Germinal center B cells
gi|2237572   Colon
gi|4703322   Kidney
i|10216415   Lung
i|4074280    Colon Expression information from PCR-based tissue screening panels:
Fetal lung

FIGURE 1B

```
  1 MVDMGALRPL IANTAYLQAR KPSDCDSKEL QRRRELALP GLQGCAELPQ
 51 RLSLNFHSLS EQQPIGRRLF RPFLATVPTF RRAATFLFDV QNWELAFFCP
101 TKDSALQSLV ATCASAPAPG NPQPFLSQAV ATKQAAFIS EERVAAVTLA
151 KAEAMAFLQE QPFKDFVTSA FYDKFLQWKL FEMQPVSPKY FTEFRVLGKG
201 GFGEVCAVQV KNTGKMYACK KLDKKRLKKK QGEPMALLEK EILEKVSSPF
251 IVSLAYAFES KTHLCLVMSL MNGGDLKFHI YNVGTPGLDM SRVIFYSAQI
301 ACGMLHLHEL GIVYRDMKPE NVLLDDIGNC RLSDLGLAVE MKGGKPITQR
351 AGTNGYMAPE ILMGKVSYSY PVDWFAMGCS IYEMVAGPTP FKDYKFKVSK
401 EDLKQRTLQD EVKFQHDNFT EEAKDICRLF LAKKPEQRLG SREKSDDPRK
451 HHFFKTINFP RLEAGLIEPP FVPDPSVVYA KDIAEIDDFS EVRGVEFDDK
501 DKQFFKNFAT GAVPIAWQEE IIETGLFEEL NDPNRPTSCE EGNSSKSGVC
551 LLL (SEQ ID NO:2)

FEATURES:
Functional domains and key regions:
[1] PDOC00001 PS00001 ASN_GLYCOSYLATION
N-glycosylation site Number of matches: 2
      1     418-421 NFTE
      2     543-546 NSSK

[2] PDOC00004 PS00004 CAMP_PHOSPHO_SITE
cAMP- and cGMP-dependent protein kinase phosphorylation site Number of matches: 2
      1     20-23 RKPS
      2     33-36 RRRS

[3] PDOC00005 PS00005 PKC_PHOSPHO_SITE
Protein kinase C phosphorylation site

Number of matches: 5
      1     79-81 TFR
      2     187-189 SDK
      3     213-215 TGK
      4     348-350 TQR
      5     544-546 SSK

[4] PDOC00006 PS00006 CK2_PHOSPHO_SITE
Casein kinase II phosphorylation site

Number of matches: 9
      1     23-26 SDCD
      2     58-61 SLCE
      3     85-88 TFLE
      4     138-141 TTEE
      5     139-142 TEEE
      6     380-383 SIYE
      7     399-402 SKED
      8     407-410 TLQD
      9     537-540 TGCE
```

FIGURE 2A

```
[5] PDOC00008 PS00008 MYRISTYL
N-myristoylation site

Number of matches: 5
     1      5-10   GALDNL
     2     41-46   GLQGCA
     3    108-113  CLVATC
     4    287-292  GLDMSR
     5    338-543  GCEEGN

[6] PDOC00009 PS00009 AMIDATION
Amidation site 65-68   IGRR

[7] PDOC00266 PS00294 PRENYLATION
Prenyl group binding site (CAAX box)

550-553  CLLL

[8] PDOC00100 PS00107 PROTEIN_KINASE_ATP
Protein kinases ATP-binding region signature 197-220  LGKGGFGEVCAVQVKNTGKMYACK

[9] PDOC00100 PS00108 PROTEIN_KINASE_ST
Serine/Threonine protein kinases active-site signature 312-324  IVYRDMKPENVLL
```

Membrane spanning structure and domains:

| Helix | Begin | End | Score | Certainty |
|---|---|---|---|---|
| 1 | 109 | 129 | 0.729 | Putative |
| 2 | 296 | 316 | 0.640 | Putative |

FIGURE 2B

BLAST Alignment to Top Hit:
```
>gi|4501826|gb|AAC95001.1| (AF063016) G protein-coupled receptor
          kinase GRK7 [Spermophilus tridecemlineatus]
          Length = 548

Score =  961 bits (2457), Expect = 0.0
 Identities = 468/552 (84%), Positives = 506/552 (91%)
 Frame = +1

Query: 4     VDMGALDNLIANTAYLQARKPSDCDSKELQRRRRSLALPGLQGCAELRQKLSLNFHSLCE 183
             +DMG LDNLIANTAYLQARK +D DS ELQRRRRSLALPG QGCAELRQ LS FHSLCE
Sbjct: 1     MDMGGLDNLIANTAYLQARK-TDSDSRFLQRRRRSLALPGPQGCAELRQSLSFHFHSLCE 59

Query: 184   QQPIGRRLFRDFLATVPTFRKAAIFLEDVQNWELAEEGPTKDSALQGIVATCASAPAPGN 363
             QQPIGRRLFRDFLATVP + +A  FLEDVQNWELAEEGP K S LQ L ATCA  P P
Sbjct: 60    QQPIGRRLFRDFLATVPKYSQAVAFLEDVQNWELAEEGPAKTSTLQQLAATCARDPGP-- 117

Query: 364   PQPFLSQAVATKCQAATIEEERVAAVTLAKAEAMAFLQEQPFKDFVTSAFYDKFLQWKLF 543
             Q FLSQ +ATKC AA+T EER   V AKAE M FLQEQPF+DF  S FYD+FLQWKLF
Sbjct: 118   -QSFLSQDLATKCRAASTDEERKTLVEQAKAETMSFLQEQPFQDELASPFYDRFLQWKLF 176

Query: 544   EMQPVSDKYFTEFRVLGKGGFGEVCAVQVKNTGKMYACKKLDKKRLKKKGGEKMALLEKE 723
             EMQPVSDKYFTEFRVLGKGGFGEVCAVQV+NTGKMYACKKLDK+RLKK+GGEKMALLEKE
Sbjct: 177   EMQPVSDKYFTEFRVLGKGGFGEVCAVQVRNTGKMYACKKLDKRRLKKRGGEKMALLEKE 236

Query: 724   ILEKVSSPFIVSLAYAFESKTHLCLVMSLMNGGDLKFHIYNVGTRGLDMSRVIFYSAQIA 903
             ILEKV+S FIVSLAYAFESKTHLCLVMSLMNGGDLKFHIYNVGTRGL MSRVIFY+AQ+
Sbjct: 237   ILEKVNSPFIVSLAYAFESKTHLCLVMSLMNGGDLKFHIYNVGTRGLAMSRVIFYTAQMT 296

Query: 904   CGMLHLHELGIVYRDMKPENVLLDDLGNCRLSDLGLAVEMKGGKPITQRAGTNGYMAPEI 1083
             CG+LHLH LGIVYRD+KPENVLLDDLGNCRLSDLGLAVE++  KPITQRAGTNGYMAPEI
Sbjct: 297   CGVLHLHGLGIVYRDLKPENVLLDDLGNCRLSDLGLAVEVQDDKPITQRAGTNGYMAPEI 356

Query: 1084  LMGKVSYSYPVDWFAMGCSIYEMVAGRTPFKDYKEKVSKEDLKQRTLQDEVKFQHDNFTE 1263
             LM K SYSYPVDWFAMGCSIYEMVAGRTPFKD+KEKVSKEDLK RT++DEV F H+NFTE
Sbjct: 357   LMDKASYSYPVDWFAMGCSIYEMVAGRTPFKDFKEKVSKEDLKRTMKDEVAFHHENFTE 416

Query: 1264  EAKDICRLFLAKKPEQRLGSREKSDDPRKHHFFKTINFPRLEAGLIEPPFVPDPSVVYAK 1443
             E KDICRLFLAKKPEQRLGSREK+DDPRKH FF+T +NFPRLEAGL+EPPFVPDPSVVYAK
Sbjct: 417   ETKDICRLFLAKKPEQRLGSREKADDPRKHPFFQTVNFPRLEAGLVEPPFVPDPSVVYAK 476

Query: 1444  DIAEIDDFSEVRGVEFDDKDKQFFKNFATGAVPIAWQEEIIETGLFEEINDPNRPTGCEE 1623
             D+ EIDDFSEVRGVEFDDKDKQFF+ F+TGAVP+AWQEEIIETGLFEEINDPNRP G  +
Sbjct: 477   DVDEIDDFSEVRGVEFDDKDKQFFQRFSTGAVPVAWQEEIIETGLFEEINDPNRPSGDGK 536

Query: 1624  GNSSKSGVCLLL 1659
             G SSKSGVCLLL
Sbjct: 537   GDSSKSGVCLLL 548 (SEQ ID NO:4)
```

Hmmer search results (Pfam):

| Model | Description | Score | E-value | N |
|---|---|---|---|---|
| PF00069 | Eukaryotic protein kinase domain | 248.8 | 7.7e-71 | 1 |
| PF00615 | Regulator of G protein signaling domain | 31.9 | 9.7e-08 | 2 |
| CE00359 | CE00359 bone_morphogenetic_protein_receptor | 22.3 | 1.3e-05 | 1 |
| CE00220 | CE00220 ACTIVIN_RECEPTOR | 8.3 | 0.084 | 2 |
| PF00433 | Protein kinase C terminal domain | 8.2 | 0.3 | 1 |
| CE00031 | CE00031 VEGFR | 5.6 | 0.084 | 1 |
| PF01821 | Anaphylotoxin-like domain | 5.6 | 0.17 | 1 |

FIGURE 2C

```
CE00022  CE00022 MAGUK_subfamily_d                      4.2          1.4    1
CE00203  CE00203 ERBB_RECEPTOR                          1.0          6.4    1
CE00292  CE00292 PTK_membrane_span                    -75.7      0.00015    1
CE00287  CE00287 PTK_Eph_orphan_receptor              -86.7        0.011    1
CE00286  CE00286 PTK_EGF_receptor                    -123.0       0.0016    1
CE00291  CE00291 PTK_fgf_receptor                    -129.4         0.23    1
CE00290  CE00290 PTK_Trk_family                      -179.1       0.0062    1
CE00016  CE00016 GSK_glycogen_synthase_kinase        -221.2       0.0002    1
CE00288  CE00288 PTK_Insulin_receptor                 247.1            9    1

Parsed for domains:
Model    Domain  seq-f  seq-t    hmm-f  hmm-t      score   E-value
PF00615   1/2       55     78 ..      1     24 [.    29.2   5.6e-07
PF01821   1/1      141    159 ..     17     35 ..     5.6      0.17
PF00615   2/2      162    176 ..    129    143 .]     3.0        14
CE00203   1/1      299    324 ..    848    873 ..     1.0       6.4
CE00031   1/1      288    338 ..   1043   1093 ..     5.6     0.084
CE00220   1/2      300    339 ..    320    367 ..     5.6      0.51
CE00220   2/2      349    362 ..    382    395 ..     2.9       3.2
CE00359   1/1      312    362 ..    272    327 ..    22.3   1.3e-05
CE00290   1/1      192    398 ..      1    282 []  -179.1    0.0062
CE00286   1/1      191    419 ..      1    263 []  -123.0    0.0016
CE00288   1/1      191    426 ..      1    269 []  -247.1         9
CE00022   1/1      308    439 ..    138    272 ..     4.2       0.4
CE00291   1/1      191    448 ..      1    285 []  -129.4      0.23
CE00292   1/1      191    448 ..      1    288 []   -75.7   0.00015
PF00069   1/1      191    454 ..      1    278 []   243.8   7.7e-71
CE00287   1/1      191    457 ..      1    260 []   -86.7     0.011
PF00433   1/1      455    471 ..      1     17 [.     3.2       0.3
CE00016   1/1      110    499 ..      1    433 []  -221.2    0.0002
```

FIGURE 2D

```
   1 CCAGGAGCCG CACTTTGCAG TAAGCGAGA TCACGCCACT GCACGCCACT
  51 CTGGGTGATA GACCGACATT CTTCTCAAA ATAAAAATTA AAAAAAATAA
 101 AAAATATATA TAAATATGTA TATATCTCTC ATATCAATGC TACCTTTTC
 151 TCAAGGTTCT ACCTTGCTAG GTTGCCACTA CATTCCTAAG AACCACGGA
 201 AAAGGCATTT GCTCCTCCGA ACAAATTATC AGACCAATTT CTCACTACTG
 251 AACAATGTGG ACCGGGGTAA CATATAAAGA ACAGAAAAGT ATCCAACATT
 301 TCCCGTGTTG GTTTCAAAGC AGACAGCATC GTTCAGAGCA GCGGTCACCG
 351 GTGCAGATCG CCCATCTCCA CGCAGATGT GATCGTTTCC AGCGCAGCCG
 401 TGCAAAGCCA AAGGGCACCC ACCAGTTCAT TACATAATTC CTGGTAGCAT
 451 GAGGCCAACT GTGTATGTGC TCTAGGGGAA CAGTCGGAGG CTCTGACAGC
 501 CACACCAAGG CGATCATGAC TATCTTTTCA CAAAGTGTAT GCTACCACTT
 551 GTTTGGAAAA AGACTGACCA GCTTTTTTCC CCCTCCTTCT CCCTCTCTCT
 601 TTTTTTTGCT TGTAAACACT TTGGTATAAT ACTGAATGAC TTGTTTTAA
 651 GCTGCCTTAG CCTTGCTTTG TGAAGAAAAA GCCTGAGTAT CCTTTCCCTG
 701 TGGGCACAG GTTGTTATTT TTGGAGCAGA AGTTCTTAGC CTGATCTCTG
 751 TCTAGATCAA TTTCTGTCTT GATGAGGCCG AGGTCTGTGA CAGCGCGGAG
 801 CGTCCTCCGT GGAACGAAGC TTCCTGGCTT GGTGGGGCGC ATGGGCAAAG
 851 ATGTTGAGGG GCCACGTCTG AAACTTCACT GCTCTTGGCT CCACCGGAAG
 901 GCTCCTTGGC ATTCAGAGTC TGCTCGTTAG ATTGTGCCCT TGGAACAGTC
 951 GCGACCGCAT GCCCGTGAGT GGGTGCTTTC TGTCTTTGCG ATCATGGAAA
1001 ATTCTTGTCT CATTCAGAGC CGAGACACTC CAGGCCAAGT CCCTTCATTT
1051 CAGGAATATG GCTTTTTCTG CTTATACTGC TTCATGGTAT GTTTGGGTG
1101 GAGATGGCCC CTCTTTTTTT TTTTTTTTT TTTGAGACGG AGTCTCGCTC
1151 TGTGGCCCAG ACGGGAGTGC AGTGGCGCAA TCTCGGCTCA CTGCAAGCTC
1201 CGCCTCCCGG GTTCACGCCA TTCTCCTGCC TCAGCCTCCC GAGTAGCTGG
1251 GACTACAGGC GCCCGCCATC AAGCCCGGCT AATTTTTTTT TTTTTTTGTA
1301 TTTTTTTTAG TAGAGACGGG GTTTCACCGT GTTAGCCAGG ATGGTCTCGA
1351 TCTCCTGACC TCGTGATCCG CCCGGAGATG GCCCTCTTT TAACCCAAGG
1401 TACTCCAGGT CACAGACTCC TCAGAGCTAA GACAGCTGCA GGATTTCTGC
1451 AAGCTATTCA GGGTGCATCT GCCCTGGCCA ACACTGCAGT CCTTAGGGCC
1501 TCTGGGAACA CATCTCGGGA CTCAAAGCTC ACAACATCCC CTCTGTAACC
1551 TGCTCTTCGT GTCAGGCTGC TAGAACCTGG GAGGAAACTC CTCTGACTTC
1601 TCACAGTTCC TCTGCCTGAC CTGCTATTCC TAGGAGTTTA CATAGCTTGA
1651 GGCTGATAGG AAACAAGTAA AATTAGAAAC AGATTAAACT ACTGCATCAG
1701 CAACAAATTA GATGACAACG GTATGATCAC TTCCTTGGAA CACAGTTCTA
1751 GCTAGATATT CAGGGTACAG GCCTATGTGG AGAAAGACCC TAAGATGAAG
1801 GGACCAGTGG GGGAGGTGGC CCCGGCAGGT GTCCCAGCAG CTTTCGCCTT
1851 GGCAGGTGGG AGCATGACCT ATCGTGTGCA CTTCCTGGCG GGCTATACAT
1901 AGCCAGTCAA AGCTTCTTAC AAGAGAAACC TCTTTCACAC CCTCCACGGG
1951 TCCCACCCAC AGGCCACAGG ACTCACTGTA AATCCCTTCG ACGTTGTCTC
2001 ACCCGGGAAG GGAAAGCAGC CAGCAGCCCT CCAGCCCTCT TGTGCTTTCC
2051 CTGGGAGTGC CCCCCGTGCT CAGCCATGGT GGACATGGGC GCCCTGGACA
2101 ACCTGATCGC CAACACCGCC TACCTGCAGG CCCGGAAGCC CTCGGACTGC
2151 GACAGCAAAG AGCTGCAGCG GCGGCGGCGT AGCCTGCCCC TGCCCGGGCT
2201 GCAGGGCTGC GGGAGCTCC GCCAGAAGCT GTCCCTGAAC TTCCACAGCC
2251 TGTGTGAGCA GCAGCCCATC GGTCGCCGCC TCTTCCGTGA CTTCCTAGCC
2301 ACAGTGCCCA CGTTCCGCAA GGCGGCAACC TTCCTAGAGG ACGTGCACAA
2351 CTGGGAGCTG GCCGAGGAGG GACCCACCAA AGACAGCGCG CTGCAGGGGC
2401 TGGTGGCCAC TTGTGCGAGT GCCCCTCCC CGGGGAACCC GCAACCCTTC
2451 CTCAGCCAGG CCGTGGCCAC CAACTGCCAA GCAGCCACCA CTGAGGAAGA
2501 GCGAGTGGCT GCAGTGACGC TGGCCAAGGC TGAGGCCATG GCTTTCTTGC
2551 AAGAGCAGCC CTTTAAGGAT TTCGTGACCA GCGCCTTCTA CGACAAGTTT
2601 CTGCAGTGGA AACTCTTCGA GATGCAACCA GTGTCAGACA AGTACTTCAC
2651 TGAGTTCAGA GTGCTGGGGA AAGGTGGTTT TGGGCAGGTA AGTGTCTCCC
2701 AGTAGCCAGG CTAGAAGCTC AAGCATAGAG CATGAAGGG GGTAATGTTG
2751 CCTTTCTTTT TTTAAATCTC AGTTACTTAG AACTAATTTC AGCACCATAT
2801 GTGGAGGATT TCTAGCCCCG TCTCCCCAGC CCCCTTCTT GTGTGTGCCA
2851 TGGTGTGAAA TAAAACACAA ATGGCATGAG ACAGACAAGC AAAATTTATA
2901 CTTGGCCAAG ACTCTGTCAT GGGTCTCCAT TAGGAACGTG CTGAGATGCC
```

FIGURE 3A

```
2951 TGGACACTTC AGAGAATGAT AC AATGTGT GA AGAAGA" CTCC TTC
3001 C TAAATT T GATAATGAAG   A TTCAAG AAAAATGGAT AT TA  A A
3051 ATA TCTAAC TAGCTGGGTC T GTGACAT  CC  TAA CC CAGC ACTT
3101 GGAGGCTGAA GCAGGAGAAT CA  T GAGCC TG GAGG  GG AGGT GCAG
3151 GAG CAAGAT CGTGCCACTG CA TCCACC  TG GTGACAG AGCAA ACT
3201 AAAAAAAAAA AAAAAAGAA AGAAAGAAAA GAAGAAAAC ACTTA CTT
3251 AAGTAAGGTT GAGAACCTCT TTTGTACCAC TGTTGTGCC AGCT  CTC
3301 TTTTAAGTAA TAAAAAATAT TT AGGTAAA ATTTGCT GA TATAAAACTA
3351 ACCATTAACT GTTTTAAAAT GTACAATGCA GT GCACTTC GCACAAATG
3401 AATG TGGGT AAGCAACACC T AATCTGGA TCAAGACAC TCTCATCAC
3451 CCTGTGCCCA TTAATAGTGC CT CCCATCC CTCTCCTCC  CCAGC CTGA
3501 CAACCACTAG TCCGCTTTCT GT CTAGGG AT TGCC TAT TCTGC TGTT
3551 T CACACAATA TGTGACCTTT T GTGTCTGGC TTC TTTCAC  CATTAGAAT
3601 TTTTTGGGGT TCATTCACAC T TAGCATGT GTCAATACTC CATT  TTT
3651 TATGGCTGTA TAATATTCCA TC TATGGA  GTACTACAT  TCATC TAGCC
3701 ATTCATCTGT TGATGGACAC TT GGCTGTT TTCACCT  T GGCTATTGT
3751 TATGGTGCTG CTATTCATGC ACAAGTATT  GT  GAA CC TTGT TT CAT
3801 TTCTCTTGGA TTTATGCCCA GGAGTGGAAT TGCTAGGGCA TATGGTCATA
3851 CTATGTTTAA CTTTTCAAGG AGCCACCAAA CTTCCACAT TTT TATTC
3901 CACCAGCAAT GCTTAAAGGT TTCGATT CT CCACATCCTT GCCAACACT
3951 GATATTTTCC TGTATTTTTT TATGAAGGCC TGCCTAGTGA GGTGAAGGAG
4001 TATCGCACTG TAGTCCCCAC TT TT CT GA GAACACTTCT TATT ACAG
4051 TACTCCTTTC TCCAATGCCT AACATCTTTC CACCCACCTC CTCCTTTAT
4101 ATCTCCACCT CTCTGCAGTA CCATCTACTT CTACCTCTTT CTCT CT TT
4151 CTTTCTCCTT TAAGGTATGT GCCGTCCAGG TGAAAAACAC TGCGAACAT
4201 TATGCCTGTA AGAAACTGGA CAAGAAGCCG CTGAAGAAGA AAGGTGGCGA
4251 GAAGATGGCT CTCTTGGAAA AGGAAA CT  GGAGAAGGTC AGCAC  CTT
4301 TCATTGTCTC TCTGGCCTAT GC TTTGACA GCAAGACCCA TCTCTGCCT
4351 GTCATGAGCC TGATGAATGG GGGAGACC C AACTTCCACA TCTACAACGT
4401 GGGCACGCGT GGCCTGGACA TGAGCCGCGT GATCTTTTAC TCGGC CAGA
4451 TAGCCTGTGG GATGCTGCAC CTCCATGAAC TCCGCATCGT CTATCGGGAC
4501 ATGAAGCCTG AGAATGTGCT TCTGGATGAC CT GGCAACT GCAGCTTAT C
4551 TGACC TGGGG CTGGCCGTGG AGATGAAGGG TGCCAAGCCC ATCACCCAGA
4601 GGGTGAGTGA CTCTCCACCT GC CCAAGTG CGGGCACAG AGTTGGAAAG
4651 GAGGGGAGAG GGCTTTTCTA TTCCCAGGGC AAATAGAGCC TTGGACTTAA
4701 TTCTTTTGGT TTTTTTTCCT AAAGCGCT A CGTTGTCATC TTGCCTTAAG
4751 ATGAGTGGTG TAAGAGGATT AGATTCATTG GCTATTTGAG GGCTA CTT
4801 CTCTCCTCTC ACACGGGATC GGGGAGCCTC CTTTGTGAGT TGGGGATGC
4851 CTGTGCTTTT GTGATGAGAT GGAAAAAGCT GAATCCATAG TCATGGTCCG
4901 GGTGTGTCAA TAACCACCTC TATGGTGCTG TGTTCCTGAG CCAATAGACC
4951 CTTGGGTTCC TTTTCTGGAA AA GAACGGG CTGGACCCTA AAATTCCATG
5001 ATCCTAGGAG GTAAACTTTA ATCAGATAAG AAAAAGAATG ATCCGGCTGG
5051 G CTCATGGC TCACGCCTGT AATCCCAGCA CTTTGGGGAG GCCGAGGCGG
5101 GTGGATCTGC TGAGGTCAGG AGTTTGAGAC CAGCCTGGCC AACATGGTGA
5151 AACCCCATCT CTAGTAAAAA TACAAAAATT AGCCAGGCAT GGTGACAGGC
5201 GCCTGTAATC CCAGCTACTC GGGAGGTTGA GGCAGGAGAA TCGCTTGAAC
5251 CCAGGAGGCG GAAGTTGTAG TGAGCCGAGA TCATGCCACT GCACTCCAGC
5301 CTGCTCGACA GAGCAAGACT C GTCTCAAA AAAAAAAAAG AAAG AAGAA
5351 AAAGAAAAAA GAAAAAAAAT AAAGAAAGAA GGAAAAAGAA TGATCCTCTC
5401 ACACCTAGAA CATTAAAAGT AAAATATCTC CTTTCCTGTT TAGTGTGGAA
5451 TGGGCGAATG TTTTGCATTG GATGAAGATG ATATTTAAA TGAAAATATA
5501 TGGAAGAAAA CAAAGGCAAC TGATGTTTAT TTTAATCAGT T TGTTCAAA
5551 GTGACTTGCT TAAAATTCTT TGGTTAAAAA GAGAATTATA ATTAAGCGAT
5601 TATGTTAGGT GAACGACGGA AAATCTCTGG AATTCTAACA TCTTTACCTC
5651 TGAGTCTCTG TGCACAAAGG T GGAGATTC CACAGCAAGG CAGGGCTCA
5701 AACCTGGCTC TTAAATGGT T ACTTAAAACC TCATTTTTGT ACAGTTTTCA
5751 GCCTACAGGG CCCAAAGGAA ATGA GAAAAA TCATGGCAAG TTTG GAAAC
5801 TGC TGTGGTG ATTTTATGTG GC TGTAATGG AAGGGATGTT GACAAGAC G
5851 AAGCGCTGGG CTTTCACAGG T G  GGAATG CCTTCTTGTA GGGGAAGAG
```

FIGURE 3B

```
5901 GGTTCTTGAA GGGTTTTAAG AAGGGAAATC AGATGATTAG ATTTTTTGTGT
5951 TAAAAAGAGG AATGGGGCAA CAATTTGGAA GTTAGATGGT AGGTGGGAC
6001 ATCAGTTAGG AGGCTAAGGT AGTGAGTGCC CCAGGCAAGA AATAATGGGG
6051 GTCTGTACAG GACAGTGCGA TTGAAGAACT GGGAGCAAAT TGGACTTTT
6101 GGAAAGAGAT CTGATGGGAC TTCAGGACCA GCTGGGTATG CGGGTCAGGG
6151 GAAAGTGAGG GTCTCTAGCT CCAGTGGCCA GAAGGAAGAG CACATTTGTA
6201 GGCAAGCTGG CAAGTTTAAT TGTCATTATG CTGTCTATGA GGTTCCTGTA
6251 GAAGGGACAG GCAGAGATGT TCACTAGGCA TTTAGATCTA TAGGCCTGGT
6301 CCTGTGGAGG AAGACCTGGG ATAGACGTGG GGATTTGCAG ITATTATGGT
6351 TTGGGAAGCA GAGGGCACTG CTGAGTCACT GGGAAAGAGT AGGGGAAGAA
6401 GACCAGGAAC AGAAGCTGAA AAACACCAAC ATGTGGGGGT ATAGAAGAAA
6451 AGGAGCCCTG AAGAGCTTTA AGAAGTAGGA GGCTACTTGG GAGGCTGAGG
6501 CAGGAGAATG ACGTCAACCC AGGAGGCGGA GCTTGCAGTG AGCTGACATC
6551 ACACCACTGC ACTCTAGCCT GGGCTACAAA GCGAGACTCC ATCTTAAAAA
6601 AAGAAAAAAA AAAAACAAG TAGGAGGAAA GGCAAGACTG ATATAGTCAT
6651 AGGAGCTGTA TCAGTTAGAG ATGGGTTTCA GGGGCATATC CTAGAAAACC
6701 CAAATAACAA TAGATTAAAC AAGACAGAGG TTTATTTTTC TTATTTAACA
6751 GGGTGTGGAA ATAAGCACTT GCCAGCATTA GTTCAGCAGC TGCAGAATAA
6801 TGGGATCTGC ATCTTTATAA TTCTAGCCTT TTCCATCTGC TGCAAGATGC
6851 CTGCTGTAGC CCCAGCCATC AGGGCCATGT TCCAGGTAGC AGAAGGAGG
6901 AAGGGTCAGG AGTAAATAGG CATGCATGCA GCAGTTGAGT GTGGCCCCT
6951 TTAGGAGCTT TCCCTGAAGC TCCATCCAAC AGCTTTCACT TAGATGTCAC
7001 TGGCTAAGAC TGTGATCTGG CCACCCCCTA GCTGCAGAGG AAGCTGACAA
7051 ATGACATTCT TGAAAATTCT TTGGTTAAAA AGGGAATTAT AATTAAGCGA
7101 TTATAATTAC TGAATTATAT CTGGGCTCAG GAGAAGATCA CCCGGCTCAT
7151 GTCCAGGCCA TGTGTGCCCA CGTTGTAGAT GTGCAACTTC AGGCAGGGT
7201 GAAGCAGCGG GTTCTAGTTA GTAAGGATGA AGAACAGCTG GATATTGAGC
7251 AGGTAACTAG CAGCCTCTGC CACAGGAGCC AAAGAAGAGC ATTTCAGGGA
7301 GGAAAGTGTG GTCAAAGTGT CAAGTGTTGC AAAGACGTAA CGTTGCCTCT
7351 GGGATTTGGC AATTAGGAAA TCAGTGTAAG GAATCGTGA GGTCTCAATT
7401 CAGACTCTGC AGGTTGGATT GATCTAGAAG TAGGGAATGA GACTCTGGAA
7451 GGGGAGACT GGTCCCTAGA AGGGGATACA GTGGGGAAAT GCAGTTTTGA
7501 GATGGGCAGG GCAGAGCGGG TTTAGATGCT GAGGCAAAAG CCAGCAGAGT
7551 AGTGTTGAT CCTGTGGGAA GGAAAGACAG TAGATGATGG CAGAGAATGT
7601 GGGCAGGAGC TGAAGTAACA CCGTCTCCTC TGTGGGTGGG AAGGAGGAGC
7651 AGGCCAGGGA GGTGACAGAG TGTTTGCCTC CTTGGGACAT TCCTATGAAC
7701 ACAGGAACGC TGTGAATCGT GGATCCATGT CTCCCTAGGC TGGAGAAAAC
7751 TGAAGTGCAG CACTTCACAG TTTGGCATTT GTATTGTCCA TTGTGCTGAG
7801 CAGGAGCCTT CCTTCTGAGT CGCCCATGGA CATGTATCAC ACTAATTGTT
7851 GCTATATCTC GACCTTGCTG GAGGCTTAGG GGACACATAG AGCTTTGGCT
7901 CACTCCAGTC TCCTTTCTCA GTCTCCTCAG GCTCTGTTCA TGGCCCATGG
7951 CCATTTGGAA GGACAGCTCC TTCCTTGGCT CCCGGGTGCA GCTCTCTGGC
8001 TCATCTGGAA CCTGCAGGAA GGTTTCTGTG CCTCCCCAGT GCTGTCCGCT
8051 ACCAGGAACG TACTTAGTAG AGAGGCTCAC TGCCTACAGA CCTTTGGCCC
8101 TTTTACCTCT GCGTCCCTCT CCGTCCCGTG AGACCACACT TCAGGGTTA
8151 GGCCACTTGC CTCATCCAAG AAGTTTTATG CCCCAGTTTC CGGGCCTGCC
8201 ACGGAAGCCC AGGGGACCAT CAGGAAGGGT GAGGGGAGAG ACATGGAGAG
8251 CAAGATTGAA AGCCATAAAA AACAAAGAGA AGAGAAAGGA AGGCCTCCTT
8301 TCTTCACTGT TTACCCTTCT ACACAGCTAA GTAAACCCCC TTAGTTTCCT
8351 ATTCATTGCA GCTCCCACAC ATATAATTGG GCTCACAAGT AGACTGTAAG
8401 GTCATTATAT TCACAACATT TCACAGAAAA AAAAGACAGA TCATAGTTAC
8451 AGGGCTTCTG TAACCACTAA CGTTCAGTTG TGATGTCAAG ATACTGTGTT
8501 AGAGAATTAC TGTCAACATT AATTCTGTGG TTTGAATGAG TCCTCAAAAT
8551 TTGATGTGTT GCAAACTTAA TCTCCAATGT GCCAGTGTTG GAGAGGTGGG
8601 GCCTTTAAGA GGTGAGTGGA CCATGAGGGC TCTGCGGCTG TGAATAGATG
8651 AATGGATTAA TGGGTTATCA CAGGAGTGGA AATGGTAGCT TTATAAGAAG
8701 AGAAAGACCT GAGCTAGCAC ATCAGCACAC TCAGCCCAC GCGATGCCCT
8751 GAGCCATCTC AGTACTCCTC AGAGAGTTCC CACCAGCAAT AAGACTCTCA
8801 TCCTCTCACC AGACATTTCC CTCAACCTTC CTTTCCTTAT AAAATACTTT
```

FIGURE 3C

```
 8851 CCTTATAAAA TACTTAGTCT TATATACTCT GTCATAAGCA ATACAAATA
 8901 AGTTAAGACA GAAGAGGTAA TAAGGAAAAA TCACCCTGAT GATGAAGTT
 8951 GAACTCTGCA TTGAGTCTGA GCAGTTCTTC CAGAAAAGTT AAGCATCAT
 9001 GGCTTTGGAA ATTTGGCTAG CTTTTTCTCA TTCAGACAGT TATTTAGTCT
 9051 TGTATAAGTT GGGATTTCTT TCTACTAAAT ATAACAGAAT AGCAGATTT
 9101 GGTATAGATT TGGCTGTTCA GCAATTCAC GGACAAGATT TCTGTTAAAA
 9151 ATCTCCTGGC TTGCGCTGGG TGTGGTGGCT CAGGCCTAAT CCCAGCACTT
 9201 TGGGCCCAGG AGGACAAGAC CAGTCAATAG TGCGAACCTC ATCTCTTAAA
 9251 AAAAATTTTT TTGTTTTCTT TTAGGCTGGC CGTGGTGGCT CACACCTGTA
 9301 ATCCCACACT TTGGGAGGCC AAGGCAGGTG GATCCCCTGA GGTCAGGAGT
 9351 TCGAGACCAG CCTGGCCAAC ATGTGAAAC CCTGTCTCTA CTAAAAATAC
 9401 AAAAATTACC CAGGCATGGT GGTGGGTGCC TGTAATCCCA GCTACTTGGG
 9451 AGGCTGCTGT GGGAGAATCA TTTGAACCCG GGAGGTGGAG GTTTTAGTGA
 9501 GCCAAGATCA TACCACTGCA CTCCAGCCTG GATGAAAGAG AAAGACTCTG
 9551 TCTCAAAAAA AAAAAAAAAT TGTTTTAAAC TTAGCCAGGT GTGGTGATGC
 9601 ATGCCTGTGG TCCCAGCTAC TTGGGAGGCT GAGGTGGGAG GATTGCTTGA
 9651 GCTCAGGAGT TCAAGGCTTC ACTGAGCTAT GATCATGCCA CTGCACTCCA
 9701 GCCTGGGTGA CAGAACAATA CCCTGTCTCA AAAAAAAAAA AAAAAATCTT
 9751 TTGGCCTTTT CCTCCTTGTC ACAAGTGGCT GTTGCAACTC CAAATATTGA
 9801 GTCTGCATTC CAGGAGAAGA AAAAAGAGGA GAAAAGAACA ACATCCACAG
 9851 ATACCTGCTT ATAGCCCATT AGCCAGGACC ATGTCATATG TTCACTTCTA
 9901 GCAGCAAAGG AGGCTGAAAA ATAGAGTATT TCATTTTCCA GCCTCTGTTT
 9951 TGGCGGATGT TAAAGGAGAG GAGGAATGAG ATTAGGTGTT GGGTGAGCTC
10001 ACAGCATCTG CCACACCAGG CCCCAGGAAA AAAATATTGA TCAGGATTAG
10051 GAAATCAAAT TCAGATTCAT TACTTTTACA GACATTGGAA CTAAAGAATG
10101 ATTGTGACAA TGGTATCCTA GACAAAATTC TAAGATGGCC CCCATCAAT
10151 GACCCTTGCT TGCCCTTGTA TAATCCCCTC CCCTTGAGTG TAGACAAGAC
10201 CCGTGAGTAT GATGAGATAT CACTGCCATG GTTGTGTTAT GTTACAGGGC
10251 AAAAGGGACT TCAGAGTTTT AATTACAGTT ACTAGTAGCA GGGTGTTGTG
10301 GCTCACGCCT GTAATCCTAG CACTTTGGGA GGCTGAGGCA GGCAGATCAT
10351 GATGTCAGGA GATCAAGACC ACGCTGGCTA ACACAGTCAA ACCTGTCTC
10401 TACTAAAAAT ACAAAAAAAT TAGCTGGGCA TGATGGCACG TGCCTGTAGT
10451 CCCAGCTACT TGGGAGGCTG AGGCAGGAGA ATCGCTTGAA CCCAGGAGGC
10501 AGAGGTTGCA GTAAGCCAAG ATCACGCCAC TGCACTCCAG CCAGGGTGAC
10551 AGAGTAAGAC TCTCGGAAAA AAAAAAAAAA AGTTACTAGT TAGTTGACTT
10601 TGAATTCATC AAAAGAGAAA TTATCCAGGT GGGCCTGACT TCATCACACC
10651 TATCCTTTCA ATATGGGCAT AGAGGCTAGA GACAGCAGAA CTCAGAAATG
10701 TAAAGCACAG AGGGCCTCTG TGCACCCTGC TGGCTTTGAA GATGGAGGAG
10751 CAAGGTGTGT AGGTGGACTC TAGGCACTCA GAGCTGCCTC TCCCTGACAG
10801 CCAGCAAGGA AACAGGGGCC TCCTTTCTAC AGCCAGAGTG AACTGAATTC
10851 TGCCATCACC ACATACACTT GGAAGAGGAC CTTGGGCTCC ACATCAGAAT
10901 GTAGCCTGAC CAACATCTCC ATTTTATTAG CCTTGTGAGT CCATGACCAA
10951 AGAGCCCTGC CATGCTGTGC CAGAACTTCT GACCTACGGA ACTGCAAGCT
11001 AATAAATGAA CTGTTTTAAG TTACTAAGTT TGTGGTAATT TGTTACACAT
11051 CAGTAGAAAA CTCATACAAA TAGTTAATAA GGAAGGTAG CCAGAGAAAT
11101 ATTGTAGGGT AGCATCAAAA TTAGTGGAGA AGGGCTGGGT GCTATGGCTG
11151 ATGCCTATAA TCCAGCAGT TTGGGAGGCT GAGGCGGGTG GATCACCTGA
11201 GGTCAGGAGC TTGAGACCAG CCTGGCCAAC ATGGTGAAAC CTCATCTCTA
11251 CTAAAAATAC AAAAATTAGC CAGATATGAT GGCAGGCACC TGTAATCCCA
11301 GCTACTCAAG TGGCTGAGGC AGGAGAATTG CTTGAACCCTG GGAGGCAGAA
11351 GGTTGCAGTG AGCCAAGATT GCGCCACTGC ACTCCAGCCT GGGCAACAAA
11401 GTGAGACTCT GCCTCAAAAA AAAAAAAAA AAAATTAAT AGAGAAGATA
11451 TCAACGTGCT GGACACTGTT AGAGGGATAA TATTTTCCTT TCTCACAGGA
11501 ATCAGAATAC CTACCACCAG TCAGGTGCTG TGACTCACGC CTGTAATCCC
11551 AACACTTTCG GAAGCCAAGG TGGGAGAATC CCTTGAGGCC AGAAGTTTGA
11601 GACCAGTCTA GGCAACATAG CAAGACTTTG TCTCTTAAAA AAAAAAAA
11651 AAAAATTACC TGGGCATGAT GGTATGCACC TGTAATCCCA GCTACTCAGG
11701 AGGCTGAGGC AGGAGGATTG CTTGAGCCTG GCAGTTTGAG GCTGCAGGTA
11751 GCCGTGATCA CACCACTGCA CTCCAGCCTG AGTGACAGAG CAAGACCCTG
```

FIGURE 3D

```
11801 TCTCTAAACA AA AAACAAA CAAAAAACCA CAACAAAAAC AAATAATAAC
11851 TACTCCCTAC CTTAATAGAA CCGGAGCCTG TAATTGAATT CAGAACTTTG
11901 CACATGATT. CTCCAAGTGG GTAACTCTTC CCTGGGTATG AGCTCCGCCT
11951 CCCTGGGGGC GCACAGGCCC TTCTCGCCA CTGAAGGACA CTGGGTAAAG
12001 TACTTTGGAT GTTGTTCTAC AGGCAGTAGG GAGCCATTGA AGCTTTTTGA
12051 ACAAGAAAGT GCCATCACCA GAGTGATTCC TTAGGAACAT CATTCTGACA
12101 CTATCTAAAA TGAAAGAGAA AGAGACTAGA GCTGGGGAGA AACGGGAACC
12151 CACCAAGAGC TACTGTAATA ATCTGCATAT GAGCTAATGC GGGGCTGAGG
12201 CTGGGTCCTG GGCTCTAAAC AGAGCTCAGC CCCCTGGCCT CTTACCTGGG
12251 CTCCATCAAG ATCCAGACCT TTACATGCTT CTCTTAAAAT GGGGCTGTCC
12301 TCAGTGGAGG GCTAGGGGAC AGAGAACAGC TCCTAGAACA CGGTGACTTC
12351 TGCCCCGTGG GGTCTTCTGG CAGCTGGTAC CTGGGTAGTG ACTCCGGGAG
12401 GTGCTTCAAG GATGGAAAGG AGCAGGTCTG CCCAGGTTTG AGAGACTGAG
12451 GCAGACACGC AAGGAGATGC CGGGGCTGAA GAGCATTGGC CTGGGAGGCT
12501 GAAACCTGAG GTCTTGTCCC AGCTTCATCA CTCATTCACC ATGTCTGCCC
12551 TCTCAAGTGG GCCTTAAGAC GTCTCTGCAA TTGCTACCAC TTTTGAGTCT
12601 ATGAGATAGT CTTTGAATTA TCTGGAGGAA AGAACTTTCC GGTTTGAAAC
12651 AAAGTCTCAT TCTGTCGCCC AGGCTGGAGT GCAGTGGTGT GATCTCAGCT
12701 CACTGAAACC TCTACCTCTC ACGTTCAAAG CACTACTAAC GCCTCCCTGA
12751 GGTTCAAGCG CCACCATGCC TGGCTAATTT TTGTATTTTT AGTACAGATG
12801 GGATTTCACC ATGTTGGCCA ACTAGTCTT GAACTCCTGG CCTCATGTGA
12851 TCAACTTGCC TCAGCCTCCT AAAGTACTGG GATTGCAGGT GTGAGCCACT
12901 GCACCTGGCC TAGGAGGAAA GAAGTTTTAA ACTCAAAAGA TGAATAGATA
12951 GAGTAGGTTA CTGTGATTTA CTGGACTATC AATCAGAGTT ATTATGGGAC
13001 AGAACTATGT TACTTCAGAA AAATGAAATT AACGGTTTAC ATAACTAGGA
13051 AGCCCTGGCC TGATCCAGCT GTCTGAGCAG TGTCCCTCGG AGTCTCTGTC
13101 TCTGTTTCCC AGCTTCGCTC TTCTCTGTGT TGCCCTCACT CTCAGGCAGG
13151 TACTCCCTGC ACGGGAGCCA CCAGTCGCCC CATACACTTC CTACCAACTG
13201 AACCACTCCC ACAGAGGGAA AACATTTTCT TTATGAATAG TTCCTTCACA
13251 GTTCCCAGAG AGGGCGCTCA CTGGACAACT CAGGTCACAT GTCCAACCAC
13301 AACCAATCCC ATGGCCGAG ACTAGATCAC TGCCTGTCCC AGGAGCCAGA
13351 GGAAGGTCTG TCCCACGTAA ATCTCATGGA TCGAGACCAG AAGAATGTGT
13401 TCCCCACAGG AAAATCACAA TGCAAAAGAT CGGGACTGGA TGCCAAATGG
13451 GCAAAAAAAA AAAAAAAAAA AAAAAAAAAA AACACAAAAC AGTGCAGGCC
13501 CCTAATAACT GCTGTTACCT CAATGGTTTG AAAAGTTTAA AACCTTCTG
13551 ACCCCTTAAT CACGGGATCA TGAGACCTAA GAGTTCCAAG TAGGTAACTC
13601 TTTTCTACAT ATGAGCTCAG CCTCTTGGGA CCCTTTACAA AAAGATTCTC
13651 AGTTAGGTAC TCTTCTGAGC TCCATTGTAC AGGTAGGGAA ATTGAGACCC
13701 AAAGTCACAG TACTAGTATG AGATATGATT CCAGGCACAT CAGATTTAAA
13751 AGCGCTCACA GTTTTGACTC CATCTTATTG AGTTCATGCA CATGCCAACA
13801 TATAGCCTTA TGTTTTTTTG TTTGTTTGTT TGAGACACAC TCTCACTCTG
13851 TAGCCCAGGC AGGAGTGCAG TGGCACGATC TCAGCTCACT GCAACCTCCG
13901 CCTCCCAGGT TCAAGTGATT CTCCCGCCTC AGCCTGCCGT GTAGCTGGGA
13951 TTACAAGCGC ATGCTACCAC GCCCAGCTAA TTTTTTGTAC TTCTAGTAGA
14001 GACAGGGTTT CACCGAGTTA ACCAGGGTGG TCTTGATCTC CTGACATGAT
14051 CTGCATGCCT CGGCCTCCCA AAGTGCTGGG ATTACAGGCC TGAGCCACCG
14101 CACCCAGCCA GCATTATGGT TTTTAATGCT ATAAAAGGCT TTTCACTTAG
14151 TAAGACTCAG ACACAATAAG TGCATGTGAT GACATTAGCA TATCTTCCCA
14201 GTCTGGTCTG ATATGGACAC CAACCACAAG CCTAGCTGAA CTTCTAAGAA
14251 AGGAAGACTT CAGAAAAGGA TCAGCCCCAC CTACACAGCC AATGACGGCC
14301 ATTAATATPT CAGAGCCAGC TTCTTACCCA TAGGTGCAGG ACAATTAAAC
14351 ATGTTCCAGC CACTGTCTAC ATGCACTTTT TTTTTTTTT CTTAGATGGA
14401 GTCTTGCTCT CTTGCCCAGG CTGGAGTGCA ATGGCACAAT CTTGGCTCAC
14451 TGCCACCTCT GCCTCCAGGG TTCAAGCAAT TCTCATGCCT CAGCCTCCTG
14501 AGTAGCTGTC ATTATAGGCA CCCACCACCA CACTCGGCTA ATTTGTGTAT
14551 TTTTAGTAGA GTCGGGGTTT CACCATCTTG GCCAGGCTGG TCTGGAACTC
14601 CTGACCTCAG GTGATCTGCC CACCTCGGCC TCTCAAAGTG CTGGGATTAC
14651 AGGCGTAAGC CACCGCGCCC GGTCAACATG CACTTTTAAT AAATGTGATA
14701 AGCACTTCTG CCTGTGCTCA GTTGACATCT ACATGCACAC ACTGAAACTA
```

FIGURE 3E

```
14751 CTTTGTATCA TTGTAAAAGA TTCCAAGTAA ATATAATACG AATATTGGGC
14801 AGTGAGGATC ATGCTTGTAC TTTTTAAATT CAGAATCTA TTTGGTGAGC
14851 AGTGACCTTC AGCTATTATG CAATATGAGT CTTTAAAATT TCCTATTTTG
14901 TTAGGAATGG GAATCAGGTT AGAATAGTGA CCCAGAAGCT TGTTACATGT
14951 TTAGATACCT GGTCCTGCCT TGAAGTCTCT GACCAACTCC TCACATTCAG
15001 AGGGATAATG GGAGACAGAG CTTTGGTATT ATATTTATTT CAAGCATCT
15051 ATTGTACCAA ATACAATGCT AGAGACATAC TGGAAAGGTG ATTTTTAAAA
15101 GACCTCTCAA CATGTTTTCT TGCGAGTTAA TGCCTCCATA TGTCACAACC
15151 ATCATGACCA TCCCCCCCAG TTTTTTTTTT CTTTAAGTGC TCACTTCTCA
15201 GATCTAGCTT AAGAAAGACA TACAGGAGAG GCATTCTGGT CACATGAGCC
15251 ATGAAGTCAT GGTCACACTT TGGCCTGACC AAAAGGATTA CCACCAGCAT
15301 TGACCAAATT TAATTCCTAC TAACTTTTGA CCCCTACAGA AATTTGAAAT
15351 CTATTCTTAA ATTATTTACC ACTACCAAGG GCATTCAAAA ATATTCATTA
15401 CAGTCTGTAA TTACTTTTAA CATTCCTTCA TCCAAAAGGC ATGCCTTTAT
15451 TCACTCACTC ACTCACTTGT TTATTCAACT TACATGTATC AAGTGTTTCC
15501 CACATGCCAG GACTCTTCTA AATATGAGGG ATAGCCAGGT GCCGTGGCTC
15551 ATGCCTGTAA TCCAGCACT TTGGGAGGCC AAGGTGGGCA GATCACTTGA
15601 GGTCAGGAGT TTCAGACCAG CCTGGCCAAC ATGGTGAAAA CCTGTATCTA
15651 CTAAAAATAC AAAAATTAGC TGGGTGTGGT GGCGGGCCCC TATAATCCCA
15701 GCTACTTCGG AAGCTGAGGT AGGAGAATCG CTTGAACCCG GAAGGCGGAG
15751 GTTGTAGTGA GCCCAAATCA TGCCATTGCA CTCCAGCCTG GGAGACAGAC
15801 CGAGACTCCA TCTAAAAAAA AAAAAAAAAA AAAAAATTG AGGGATAGAA
15851 GGAAGAGCAG AAAATGCACA TGATTCCTGC CTTCATGAAG CTTACAGTCT
15901 AGTGGGGAAG ATAGAACTTA ATAAACATTC AGACTGGCCG TGGTGGCTCA
15951 TGCCTGTAAT CCCAGCACTT TGGGAGGCCG AGGCGGACAG ATCACTTGAG
16001 GTCAGGAGTT CGAGACCAGC CTGGCCAACC TGGTGAAACC CTGTCTCTAC
16051 TAAAAATACA AAAATTAGC CGGGCATTGT AGCACATGCC TGTAGTCCCA
16101 GCTACTCGGG AGGCTGAGGC AGGGAATTG CTTGAACCCA AGAGACGGAG
16151 GCTGCAGTGA GTCGAGATCA TGCCACTGCA CTCCAACCTG GGCAACAGAG
16201 CAAGATTTTG TCTCAAAAAA AAAAAAAAAA GGGAACTTAA TAATCATTCA
16251 AATAAGTATT AAATATCACT TATGATAAAT GCTGGGAAGA CATGGTACAT
16301 TGGGCTCTCC AAGGAGGATT TGACTTAATA TCTGAAAATC AAAAAGTAAA
16351 CCACATGGGA AATTCAACTT ACATGATACT AGAAGGAAAG GAATTCACTC
16401 AGCAAAGAGG TTCCGGTGGT GTCTCAGATT GGGCTCCCTG GAAACAGACT
16451 GAGACAGATT TACACATGGA AGATATTGGG GAGCTATGAT ATTGTGAAAT
16501 ATGTGTTTGG TCTTCATCCC ATTTTCTGGC ATACAACTCC AAATCTTCAA
16551 AGTGAAAAGC ATCTTTTTGT ATATTAATGA GTTGACTGAT GGCTGGCAGC
16601 CCCTAGGAAG CTGCAGGATG GAGACTGCTC ACCAGAAAAG CCAAGGTAGG
16651 ATTAGAGGGT TAGGACTTTC AGCCTATCCC CAATGGCCA ATGATTTTAT
16701 CAATCATGCC TGTGTAATGA ACACTCCATA AAAACCCAAA AGGGCAGGGT
16751 TCAGACAGCT TCCTGATAGC CAATCACGTG GAGGCTTCCA GGAAGATGAA
16801 CAAGAACACA TCCACGTGCT GGGAGTGTGG CTCACCCCAG CTCCATGGGG
16851 ACAGAAGCTT CTGAACTTGG GACCCTTCCA GACTTGGTCC TGTATGACTC
16901 TTCATTTGGC TGCTTATTTG TGTCATTTAA AATATCCCTT ATAACAAACC
16951 AGAAAACATA AGTGTTTCCC TGCATTCTGT GAGCTGCTGT GGCAAATTAA
17001 TTGAACCCAA AGAGAGGTTT GTGGGGACCT CAATTACAG CTGCTGGGTC
17051 AGAAGTTTTG AAGCCTGGA CTTGCCACTC GCATTCAAAG CCTAGAGGCA
17101 GCCTTGGGGA CTGAGCCCTC ACCCTGTAGG ACCTGGCACT GTCTCCAGCA
17151 GATAGTGTCA TAATGCATTT GAATTAGAGG ACATCCAGCT CGCATCTGCT
17201 GCAGAATGGA TTCCTGGCTG GTTGTGTTT TCAGAGTATT GTGGGAGAAA
17251 CTGAGTTTGT TTCTTCTACT CAGGAGTGCT CTCCTGAGAT GCAGCCATGA
17301 GGAAGGCAGG ACTGGGCAGA GAGAACCTCA CCCCTAGTGC GGCAGGCGGT
17351 GGGGACTAAG ACCTCAGCCA TCCTTCAGGG AGCTCTGGAG TTGGGATGAC
17401 TCTTCTGAGT TGGCCCAAAT TGAGGTGGGG TCCAGACTTG TGTATCCCTA
17451 AGGATGCAGT CACTGACTGT GAGTAGCTGC CAGAAGGGGG CGGAAGCCTG
17501 GGATGCCATC CCCGCTGCAG AAGGCAGTTC CCACGGAGGG GTGCAGCTGT
17551 GAGCCATCAC CAAGCAGTGG CCCCAGCCAG GCATGGCTGC ATAAATTTGG
17601 GGGCTCACTG TGAAATAAAA ATATAGGGCC TCTTCTTCAA ATATCGGGAA
17651 AAAGCCTCCT TTCATGCTCT ATTTTTCAAC CAGCCATAGG CTTTGGATTT
```

FIGURE 3F

```
17701 GCTATTTAAT GTCATACTTC CCCAGGCTCT GGGATACTCA AAGAGTCAGT
17751 AGAGACCCTC ACAGACACCC AGGGCTCCAA CCCACGACTC CACCTCAGGA
17801 AGCATGTGCC TGACCCCAGC CCTCCCTGCA CCTGAGTCCA GTCCCCTACC
17851 AGGCAGAAAG TGGCAATAGT CACTGGGTCA GGGTGGGCGT AGAAGTGGGA
17901 GGTGGGGAAG CAGACAGCCA TGAACCCATC CCGGGCAGGC AAGCAGGTGG
17951 CAGGAGGGGG ACTGTGTGAG CTGAGGCTCC AAGTACGCCT CTATTGGCTT
18001 ATTGGACTTC ACTTAAAACA CACAAATTCA AAGATAAATG ATTACAAACA
18051 GCATTAAACC CCAGTAAAGG TATGCCTCTG AGCACAGGGC CCTGTCCATG
18101 GGCACTGGAA ACTGGCCTGG CACCAGCAGC TGGACGGTGG GGGCCAAGAA
18151 CCTGAACAGG GGATTGGAGC CAAGTAGCCC CCACAGGTGG GGAAGAGCAT
18201 TTCAGGCCAT GGGAATAGTC TGGGCAAGTA TCTCTTGCTT TAGGGAAAT
18251 GAAAAGGAAG CCAGGAAATG AAAAGCACAT CCTAAGACGA AATGTGGTTC
18301 AAATGAAGAT GGAGAGGTGG CAGGGGCCAG ACGGAACCTG GCATTATGGG
18351 CCATGTTAAG GACTTTGGGT GATCGTCTCT GATCACTGGA AAAGCTGTGG
18401 CAGGGTTTCA TGAAGGGGAC AACATGTTTC AAATTTTGTT TTGAAAAGAT
18451 TACCCCAGGT GAAGTGAAAC AGATTGGAGG AGATTCAGGT AGTTTGTGGT
18501 CTTTCTAATC CAGGTAAGAG GTGATGGGGC TCAGACCACA GAGGGAGTAG
18551 TGGAGACAGA ACGCAGTGGA TGAATTGGGG CGATATAATA TTTCAGAGTG
18601 AATAGGCCTC AGTGATGGTT TGGATACGGG GTTAAGCCAG ATGGGGTGTC
18651 AAGAATGATT TGTTAGATAA GGCTGTGTCA CAAGCACAGA CTTAGACCCT
18701 GAGTACTAAA CAGGGAACCA GGCAAACAAA GACCCTGAAT ACTAAACAGG
18751 GAACCAGGCA AACAAATGCC TGCCTTCATG AAGTTCCAGG AGAGGAAAGG
18801 GATGGACAAG GACATGGGCA GTGATAATAC GGTGTGATCA GGGTTGTCTG
18851 AGCTGGGTAC ATAGGAAGGG CACCCAGCCC AACATGACGA CCTGGAGTCA
18901 CAGGGTCAGG AAGGGCTTCC AAGGGGAAGG GACAACCAAG CTAAGACTTA
18951 AAAGACATGA AGCCAGACAG GTAAAGAGGA AGGAGCATGC GCTAGGTAAA
19001 GGGATCAGCA GAGCTCAATA GTCCTCAATG GCGGGTGATT GTGCCAAACT
19051 TCCTGGGGAT ACTTGGCAAT GTCTGGAGAC AGTTTTGGTT GTCATGACTG
19101 GGGAACTGCT ACCAGCATCT AGTGGGTAGA GGCAGGGATA CTGCCAAACA
19151 TCTTACAATG AATAGCACAG CCCCCAACAC AAAGCATATT CAGCCCACAA
19201 CATCCACAGT GCCACACTTG AAAACCCTGC CATAAAGGCC TCCCAGCACA
19251 AGGCCTGAGG CTCAGTCGCA GAACAGAGTG GCTTTGCAGC TGGCTGCAGT
19301 GTGGAGTCAT GAGGTGGGAG GGGTGACTAA CGATACAACT AGAGAGTTTA
19351 GCAGACACCA GGCCCTAGGG GCTGGAGGAG TTGCACAAGG GGAGTTTGAA
19401 CCTATTGGCA AGGGTGCTGG GGAACCGATG AAAGGTTTTT AGCAGGGAAG
19451 TGACAAAATC AATCTTGGGG CCAGGTGTGG TGGCTAATGC CTGTAATCTC
19501 AGCATTTTGG GAGGCCAAGG CACAAGGATT ACTTGACCCT AGCAGATGGA
19551 GACCAGCCTG GGCAACAAAG CGAGACTCTG CTCTATCTTA AAAAAAAAAA
19601 ATAGCCTTGG AATTACATCA AAGAGAAGGA GTTAGAATGA GCACAGAAAG
19651 GCTGGGAGGG AAGCAGAGGA CTCAGGGAAC TGTGGGCTTG CACATTGTCT
19701 AATGGACTCA CGGGAATAAG GAGAGGCTGG GCCAGGGGGT CTGCAGGATG
19751 CGGCAGGAGG GGGCTGTCAT GTGACATGAT ACAGTTCAGG GACCTAATGG
19801 TTGCCGTGTC ATCTAATCTA ATATACACAC ATGTTAGAAG CTCAGAGCAT
19851 TCATTTAGAT CATGCGCAGC TGATGAAATA TAGTCCTGCA GGTCAAGGAG
19901 AAAGGAGCTT GAGCATTTGA ATCCTGGTTC TGCCACTTAC TCCTGGCTGC
19951 TGTGTACAGA TGTGCAGGCT GACTCCCCTG CATGGGAGAG TGGGGCTGA
20001 CGTCACATGG CAGGCTGGTT TGCTCCACGC ACCAAGACAT TTGCAGTGCC
20051 TTCTAATTGG CACAAATCTA CTCATGGGTT GGCCACACCC CTGCACATGA
20101 TCTTACGCAA GTCAGACTGC TTCTCTGAGC CTGCTTAATA CTGCCTGCCT
20151 TTAGCGTTGA TGACAAGATT AAGAAACAAA GTAGATAAAT GCCTAGCCGA
20201 GGGTCAGCCA CTTGGTAGGC ACTCAAGAAA TGATTGTACA AGAAGCTCCA
20251 GACCTTCAGT CACAATCCCC GCTGTTGCAA TTGTTTCTGC CTCACCTGAC
20301 AGGCACTGTA GTTGCTCAGG TGACCTCTGC AGCTGTGCTT TGTTCTCTGC
20351 GAGGCACAGG GAGCCAGCGG GACCCCAAGG CTGCAGCAGT GGGCAGTGGG
20401 TGAGCAGCTT GCATCTGGGT TGAGCCAAGC AGACACTCAC AGTTGTCTTG
20451 CTTCCTCACA GCTGTGTGGG GTTTCATTTG TGGTTTTCTT CTGAGCATCT
20501 TAGAGGCACC GTGGAAAGTA TGCCTCAGCC TCCTGCCAGA GAGATTCATA
20551 GCACATGAAA CCACTGAAGA ACACGCTCAA GTGAAAGAAC GGGAACTATT
20601 GATCTCTGAC CATGTGCCAG GCCCTGCCTT TCAGTCTGAT GGAGTCTTGT
```

FIGURE 3G

```
20651 GTAGCTGTCC TGCCTGAGAC AACCAGAAAC TAGGCATCCT AACAAAAGCT
20701 GCTAATACAT ACTGTGGTAG CAGGCCTGCT TGGCCCAGG TTTTGGGTCG
20751 ACACCCAATC TGTTTTATCG TTTAATCTTT TCTCACAGTC CCATAACGCA
20801 AGAACTGTTG AGGCTCACAG GCGTTCAGTA ACGGCTTGTG CGTGACCGGC
20851 TTATAACTGG TAGAGCTGGG ATCTGAACTA CAGCAAACCA ACGCAGTCT
20901 GGGAGCCATT TCACCCCAGA CTCTATGCCT GTAAAAAGTG TTATTGTGAC
20951 GACCCCTCTT TTGGGCTCCC TGTGTGGCCT CTGTGAAATG CGTGTCCTTC
21001 CAGGGGTCTC AGGGAGAGCA GGAAGCCGCC TTTGATGGGA TGCGCCCTCC
21051 CCGCCCAGGA AGTGGCGGCA GAAAGCGAGC CCTCAGAAGC CAGGGGCAGG
21101 AGCGGCCTCC GCGCGACACT GGGCGCTCC TGATTCTGCG GCCTGGGGCC
21151 GAGCATGCGG GGCGGGCGGA CCCTCGAGCT AAGTCCCCTG GGGTCCCAGG
21201 GCCGCATTCC TCCGAGGTCT GCAAAGGCCA CTGCTTAAAG GCGCAGAGGA
21251 GCAGCTGGGA ACGAGAACAA AGCGGCCAGG CCCCCCTCGG AGGAAGGAAG
21301 GAGAGAGCCC CAGGAAACAG CTGATAGCGC TAAGCTCAGC TTGTTTTTTT
21351 CCTCTGCTCA ACAGTTCTCC TCCCACGGCA AACAAAACAT GTACATTCTG
21401 ATTCCCTCTT CTGTTTGGAT TGTGCTGTCG ACTGGATCTG GTTTCTGATG
21451 AGCTGGGGGA AGAGGCATCC GCGGGCGATT TCTGGCTCGG CCTGCCAGTG
21501 TGCTTTTGCT GGGCCGCGCC GGGANTGGCG GAGCTTCCTC TCCGGCTCCT
21551 TTCTCCCCGT CTGCGTCGCT AATCCAGCCT GGCCCGGCCA CCCCAAGGGA
21601 AGACACGGCC GTTTCTTTTG ATAGTGGAAT TCCAGGTTGC CAAGTTTTCA
21651 GATTTAATGG GAGGTGGAGG GTTGCTCCTG TCCTTGACCT TGAAGGACCT
21701 GCGCACACTC ATACTTTTTC ATGGACTTGT AAAACTGTTA AGAGGTGAAC
21751 TGTGCCCTCT CAGCTCCACC AGAAGCCCCT CCATGTTCTC TGCACTGCGA
21801 AGGTCACAGT CTGGTTCCTG GTTGTCCAGA GCCACACTCG GACTTGTCC
21851 AGGCCAGCCT GGGCCCTGCC AGTTCGGTTC AGAGTGACAC CTACAGGGTC
21901 AATGGAAGAG GCCAGCACCC AACAGCAAGA ACAATGTAGG GGGTATCTGG
21951 ACGGGCTTGG GATCTTAATC ACACCTTAAG GTGTCTACCT TCCCCAATGT
22001 CTGGACACCT GTTGGTCACA GGTGGCCCTG ATGGACTAA GCTTGAGATT
22051 ACTGTACTAG AAGGACTTCC CGCTGCCCCT GAGGGCATGG GGAGGGGCA
22101 CTGGCACTGC CAGGCGTGCT AAACCCCGTG ACGTCTGTTG TTCGATGTCG
22151 CCCAATGCTG GGTATACTTG GTTTTGCCT GACCAGCTGT TGACTGTGTG
22201 GGTCTGGAAA GGGCACCATA AAACCCAAAG TAAAATAAGG TAAAACCCAG
22251 AAAAGGATAA AACACATACA CACACACACA CCCACACACC CCTCCACTAA
22301 GAGGTGCTCA TACTCGGGCA ATCCCTACAG CCCTGGGCAT GGCGGTTCTG
22351 GTCACATGCA CTGAAGGAGA CGGTTCTGAT GCTGCTGACA CAGAGGCGCA
22401 GGGCCCTGTG TAACTGCAGG AGTTAAACCC AGCTGTAAGA GGTCAGCGTG
22451 GTTGGACCTG CTCCACGCTG CTTGGCGCGT TCTCTCCTCC CACCCTACTC
22501 TGAGGAGGCA GTTCACATGC AGAAGACAAA TGGCATAAAG GGCAGGCAAT
22551 TAATTTTTTC AGCTGGAGGC TGCAATGGAA TGTGGGTGCT TAAAGTCTGG
22601 CGTGCGCCTC TAATTCCATT CTCCTCAGTG AAATACCTCC GCTCTTCAAG
22651 GAGGTGGTGC CCTTCAAAGC TACCATGGCT GACATTTTCT GTCTTTAGGA
22701 CCAAGAGGTG AATTTAGTCC TGAAAATTAT TTGGAATGAA TCTAAGGCCT
22751 TCCTGCACGC TGTCTCATGC TCTTTCCACT ACACCAGGCC GTCTACAGTG
22801 CTGTAAAGAT GGCAGGCCAA TTCTTTACTT ATTTCCTTGG GGAGGTGCTT
22851 GCAGAGCATG GCCCAGGGTC TGGTCCCATC TCCAGAACC CTCTGCTCTG
22901 TGGAGCAGCC GAGCCAGCCT GAAACAGGCA AAAAATGGAG AATTCACTGG
22951 GATAAGGGGA AGGGAAACAT CTTTAGCAAG AATGCTAAAG ATCAAGGACT
23001 TAGTACTGGG CAAATGGGGA GAGGCAAGAA GGGGACTCTA CAAGGGAGAA
23051 AAGAAATCCT GAAGGGAACT TGGAGGGGTA AGAAAAGTC ACTTCACCTA
23101 CTTCTATAGA GGCGGAATAA TGTAGTAGTG AAAAGCGCAG GCCAGGGCAG
23151 GCATGGTGGG TCACGCCTGT AATCCCAGCC CTTTGGGAGG CTGTGGCGGA
23201 TGGATCACAG GAGGTCGGGA GTTCGAGACC AGCCTAGCTA ACATGGTGAA
23251 ACCCTGTCTC TACTAAAAAT ACAAAATTAG CCGGGCGTGG TGGTGAGCCC
23301 CTGTAATCCC AGCTACTCAG GAGGCTGAGG CAGGAGAATC ACTTGAACCT
23351 GGGAGGTGGA GGTTGCAGTG AGCCAAGATC ATGCCACTGC ACTCCAGTCT
23401 GGGTGATAGA GTGAGGCTCG GTCTAAAAAA AAAAACAAG GTGCAGCCTG
23451 TGTGTGATTC TTAGGTTGGT GATCTTAGGC AAGATTTAAC CTCTCTATGG
23501 TTCAGTTTCC TAATCTGCAA AATGGACGCT ATCTCATAGG GTTATATGG
23551 AGATCAAATG AGGAATTCAC ATAAAGCACT ACAGAAAATA TTTAGGCATGG
```

FIGURE 3H

```
23601 AATAAGCACT CAATAATGTT TTCCATTATT ATTTCCAATT TTTCTTCAG
23651 CATGTGTTTC ACAATCCTTT GTTCATGCA AGGTATGTTG T TACTTCA
23701 CCCTACACCT TCTACCGAGC AACTTAGGTT TATCCAATAT CTTCATTAGT
23751 AACTTTAATC CTTAATGTCA CTCACCTTTG AAATGTGCTC ATTGCACGGG
23801 TGCCACACAG AGCAAGCTCG CAATAAATGT TGCTGAATAA AATTTACTGA
23851 CTGCCACTGA CTTAACTTCG TTTGGATGTT GTTTATAGTT TCTTTATGCC
23901 TCTGCCACCC CAGCAGAGTC ATAAAGAACC AGACAGAATC AGGACCCAAG
23951 AACATGAGGC CCAAAGGAGA GCTGTGGGAA GTGAAATACT ATATTCAGCG
24001 AGACCCTCAG CTCCTTCCCA TCTCAGTTCC CCAAATGACA GCAAGCAGGC
24051 TGATACTTCT CAGGTGGGGT ATCCAGATAT CCCACCTGAT CCCTCTTGTC
24101 AGTTGATAAG CTGGACTCCA CATAGCTTAT AGTCAGCTTT TTGGTGCTTC
24151 ACTCTTAAAT ATGAATGACT AGACAAAGAT CAATTGTCAT TTCTAAAAAA
24201 AAAAAAAAAA AAAAAAAACT CTTCAAAATG AAAGACAGAA CCAAAACAAT
24251 CAGAGGAAAA GAACTTGTAG AAAACAGGAA CGATGCAGGG AATACAAGAG
24301 ACTATTTTCT AAAACTTGTA ATTATTATCT TTTGAGATTA AAGACAAGAT
24351 AAGGCCTCCA TGAAACAAGA ACAAATGCTG TAAATCAAGG AACATTCAGA
24401 GAACAACAAG GACATTTGGA AATAAAAAAT ATGTAAATAC ATTTGCAGAA
24451 AAACATGGAC AAATCTTAAA GATATGTTAA ATACAATAAG TCAGACATGA
24501 AAGAATACAT ACTATACTGT ACCATTTATA CAACATTTAA GGACAGACAA
24551 AACTAATCTA TAGTAACAGA AATCAAAAAG TGTTTGCCTG AGAAGTGGCG
24601 AGGACTGACT GGCAAGGGGC ACAAGGGAAC TTTCTGGACA GACAGAAATG
24651 TTTTATATCT TGTTTGGGTG GTATTTATGA GGGCGTATTT AATTATTAAA
24701 ATTCATTGAG CTGAATGTCT AAGAACTGTA CACGTTATTG TATATTAATT
24751 ATGTATCAAT AAAATCATAT TGGCAAAACT CAAAAGTTAA GTAGAAGAAT
24801 TAAGCCACTA TGTCTAGCCA TCAGTTTACA ACAAANNNNN NNNNNNNNNN
24851 NNNNNNNNNN NNNNNNNNNN NNNNNNNNNN NNNNNNNNNN NNNNNNNNNN
24901 NNNNNNNNNN NNNNNNNNNN NNNNNNNNNN NNNNNNNNNN NNNNNNNNNN
24951 NNNNNNNNNN NNNNNNNNNN NNNNNNNNNN NNNNNNNNNN NNNNNNNNNN
25001 NNNNNNNNNN NNNNNNNNNN NNNNNNNNNT GGGGAAAAAA CACAGAGGAG
25051 GAGCCTATAA AAGAGATTTA AGAGCCAATC ATTGTATGAA CCACATTTGA
25101 TCCAAATTTA AACAAAAGTT TAATGATTGT TTAAATGATT GTATGATTTA
25151 AGTTTAAATT TTACTTTTAA AAGTTTATAG GACAGTTCGT ATACAAATAT
25201 GTCCAGATAA TATTAAATAA TTATTCTTAT CTTTTAAATG AGATAATGTT
25251 ATTGTAGTGC TTTGTTTTAG TGTGTTTTCT AAGTGACCTT ATCTTTTAGA
25301 CATTCATAGT GAAATACAAA TGATGCATGA CTAGAATAGT CAGGAGAAGT
25351 GGGAAGGGAC ATAGATGAGA CAATATTGGC CATGTGTGGG TAATTGTTGA
25401 AGCCAGGTGA ACACTACTTT GGGTTTATTA TTCTGCCTCT GTTTTGTATA
25451 TATTTGAAGT TTCCCATAAT AAAATACTTT TTTAAAAATA GAAGAATTCG
25501 GGAAAAAAT GGGGGAACTT TCCCCCTATG CCCCTCAAAA AGAAATAAGA
25551 GACAAGAATG GACATTAGGA GCAAAAGGTA AGAAACATAA AGGATAAGTT
25601 CAATATTTCT GAAAAAAAGA GAAGAGACAA AATGCAAGGG AGAAAATGAT
25651 CAAAGAAATA CTATGAGAGG CTGGTTGTGG TGGCTCATGC CTGTATCCCA
25701 GCACTTTGAG AGGCCAAGGC AGGAGGATCC CAGAACTAGC CTGGGAAACA
25751 GAGAGAGACC CCGTCTGTAC CAAAGAAAAA AAAATTAACC AGGCATGGTG
25801 GCATGCACCT GTGGTCCAG CTACTCAGGA GGCTGAAGTG GGAAGACTGC
25851 TTGAGCCTAG GAGGTGGAAG CTGCAGTTAG CCACGATTCA ACCACTGCAC
25901 TTCCAACCTG GGTGACAGAC TGAAACTCTC TTTCTCTCTT TCTCTGTCAC
25951 ACACACACAC ACACACACAC ACACACATAG TGTGAGATAA TTTCCCAGTG
26001 TAGACAGCCA TTGGTTTCTG GATTGAGGGG CCAGCTGATA GCCATGATAG
26051 CCATGATAGC CAGCACCGTG GATGAAAAAA GCCCCACATC AAAGTATGTC
26101 CTTGAGAAAT TTCATCATAT TGGTGTACTG GACCACAAAC CTCACATACC
26151 TTCCTACATT CCCTCTACTG CCTCCTTTTC TCTCCCTCTT GGACAGTTCT
26201 CTGTCAGCAG CATATCCAGG CTGCGTTGCC CCTCCACTTT CAGAGCTGGA
26251 TAAAACATCA TCTGGATAAA ACATCATCCT GTGGGTATG GAGCTTATT
26301 TCCTGGGCAG CTGCTAATCA ACTGGATGAC ATGTCGGCAA TATAGCTCTT
26351 CGGATAATCC CTGACCAATG GAAACGGGAG ATGGGAAGGA CTGGGCAGCT
26401 GCATCCCCT CATCCACTCT CTCCTGTGCT TCCTCCTTGT CCCTCTTCCA
26451 GAAGACTCCC TTGTGCCTGA TGAACCAGCA GCCAGCTGGG CACCACATCC
26501 CCCTTCCCTC ACTCTCCTTT TCCCTTCTGC ATATTCTATT ATAAAATCTT
```

FIGURE 3I

```
26551 CCAAGCATAG AGCAAAGTTC AAAGAATTTC AGAAAGAATT TCACAAAAA
26601 TTCAGAAAGA ATTCACACG AGCACCTTTC AAATACCCAT TACCTAGAGT
26651 TTATCACTGA CATTTTTAAC AGCTTTACTC AGATATAATT TAACTACTAT
26701 AAAAACCATG CATTTAAAGT GTACTGGCTG GGCGCAGTGG CTCACGCCTG
26751 TAATCCCAGC ACTTTGGAAG GCCAAAGAGG ATGGATCACC TGAGCTCAGG
26801 AGTTTAACAC CAGCCTGGCC AACATGGTGA AACCCTGTCT CTACTGAAAA
26851 AAAAAAAAAA AAAAAGCCA GGCGTGGTGG TGCACGCCTG TACTCCCAGC
26901 TATTCAGGAG CTGAGCCAGA AGAATCGCTT GAACGGGGGA GGTGGAGGCT
26951 ACAGCCAGCC AAGATCACCC CACTGCACTC CAGACGGCGA CAGATGTCTC
27001 AAAAAAAAAA ATTACTGGTT TTTAGTATAT TTACAGAGGT CTGCAAACAT
27051 TACCACAATC AATTTTAGAA CATTTCTTC ACCCCAAAA GAAATCCCAT
27101 ATCCTTCAGC AGTCACTTCC ATTACACTGC TCTTCCATCC CTAAGCAACC
27151 ATTCATCTAT TTTCTGTCTC TATGGAATTG CCTATATTAG ACACCTGTA
27201 TAAATGGAAT CATGTAATAC ATGGTCATTT GTGACTAGCT TCTTCCATTT
27251 AGCATGTTTT CAAGGTTCAC GAAGCATGTA TCAGTACTTC ATTCCTTTCT
27301 TCCCCTCTCT CCCCTCCCCC AAGACGGAGT CTTGCTGTGT CATTCAGGCT
27351 GGGGTGCAAT GGCACCATCT CGGCTCACTG CAACCTCTGC CTCCCAGGTT
27401 CAAGCGATTC TCCTGTCTCA GCCTCCCAAG TAGCTGGGAT TACAGGCACG
27451 CCCAGCTATT TTTTGTATTT TTAGTAGAGA CGGGTTTTCA CCATGTTGAC
27501 CAGGCTGGTC TCAACTCCTG ATCTCATGAT CCGCCCGCCT CAGCCTCACA
27551 AAGTGCTGGG ATTACAGGCA TGAGCCACCA CCTCCCGGCT AGTACTTCAT
27601 TCCTTTCTAT GGCCAAATAA TACTCCCTTG TATATCTCTA ACATTTACT
27651 AGATTTGCTT TATCAAATGT CCATCTATCC ATCCTCTCTA TCCATCCATG
27701 TAATCAATCT TACATCTTTT ATTTTCGAGT AAACTCACTT CTCTTTTTC
27751 CAAGCCCTTG CACCTTCAGC TTGCACACCT CTCAAATAAA GCTCATATCA
27801 CTATCCTGTG TGCAAAGGAG GCTGGGAGAG ATGTTGTCTT TAGTCATCTG
27851 GGATTTCGTG ATAGAGGGAG GCAAAGGAAA AGGGAGACTG GGAATAGATT
27901 CTGCTACCTT AGCATACAGT TTCTCAATCC CATCTCCCCT CCCTCCATGG
27951 CATGCCCCAA ATCATGTATT CTAGAAACAC CAAATTCCTT AAAGCTCCCT
28001 CAATACCTTA CACTTTTTCT GACTCCATCT CTTGCACATG CTCATTACCT
28051 GGATAGCCTT CTAGGTGTTT CCCTCATATT CAGCCAGCTG TGCCTCTTCA
28101 GTGAAGTATT CTCAACACAC ACACACATAC ACACACTCAC ATAACACACA
28151 CATACACATA CACACATACA CATACAGGCA CTCACACACG CATACACACG
28201 CTCATACATA CACACACTCA CACACATGCA CATATACACA CACATACACA
28251 TGCACAGATA CACACATACA CACATGCTCT CATATACACA TGCACATTCA
28301 CACATACACT CACCCTCACA TACACATACA TATGCACACT CACATGCACA
28351 CATACACACA TGCTCACATA CACGCACACA TACACACATG CACATACAAA
28401 CATGCTCACA TACACTCACA TGCACACATA CACATACACG CTCTCATACA
28451 CATGCTCACA TACACTCACA TGCACATTAA CACATACGCA TGCTCACACA
28501 CACATGCATA CTCACACATA CACTCACATA CACACATACA CACCACACTC
28551 ACATACACAC ACCCACTCGC ACACACACAT ACACTCACAC ACATCATAC
28601 ACCCACACAC GCATACACCC ACTCACACAC ACTCATATGC CCACACACAC
28651 ACACACACAC GCACATACAC TCACATACAC ACACAATCAC ATACACACAC
28701 AATCAGATAC ACACACATGC ACACACTGAC CCCGTGGCC CCCTGCGCG
28751 TGCTCCACAC TCTATTGAAT CAACCTTCTG ACCTGTCTGT CTCTACCAGT
28801 CTCTAAATCC TCAAGGGCAA GGGCCAGGCC TTACAGCTCT CGGTATCCCT
28851 GGAACTCATT GCAGGGCATG ACTCAACAAA TGTTTTCTGC GTAGTGAATG
28901 GAAACATCT AGTCACCGTC TTTGTCGTTA TTTATTTAAA AACATGGCAT
28951 GCACCAGGTG AGGCCCTGTG ATAAGTGCCT GGATTTGGAG ACAAAGATGA
29001 GTAAGACTGT ATCCTGGGCC TCAGAGGCGC CTACAGGACC CTTTTGTCTG
29051 GACAAATGCA AAACTGGACA AGACGCCAGG GCAACAGATG TAAACCGGGA
29101 CTGTCCCAAG CAAACCGGAA CATATGGTCA CCCAAATTAT ATACCAGCTT
29151 CTCTGAAAAC AGCACTGCCA TGCTGACTCA TGCACAGCCC GTTAGATCCT
29201 AGTCACTTCC AGAACTTTCT TGTTCAGGCC AATCACTCTT CATTAGTACT
29251 TGGATTATTC ATGTTTTTC TTGTTGTGAT CCATGTAGAA ATTATCCATG
29301 AAATTTCATA TTTCTAAAGC ATTACATTAA AAAATACTTA AGCAACTAGA
29351 AATAAAACAC CTAATGCACA GCTCACACT TTCTAATGTT TTCTTCATAG
29401 AGACGGGGTC TCACAAAGTT ACCCAGGCTA GAGTGCTGTG GCTCGTCTAT
29451 CGCACTACAG CCTCGAACTC CTTGGCTGAA GGGATCCTCC CATTTCACCC
```

FIGURE 3J

```
29501 TTTTGAGTAG TTGGACTAC AGGCACACAC CACTGCATCC AACTTTTCCA
29551 ACCTTTCCTC AAGTACTGAA ATGCATAGTT GTAATCAGTG GGTCACAATT
29601 ATTACATATA TAAATTCCTT GGTATTAACA ATACACTCTG GTTTATCATC
29651 TTATTCATGG GCTTTGGGT GTTTCCAGCT CGTGACCATT CTGACTTAAT
29701 GAACTTATCA ACATCTCAAT ATAGATTCCT TTTCTTTCT TCTGAGTCTC
29751 TTCTTTGACG TACATACTCC ACAGTTAAAT AATCTGGTTG AAAGACAGGA
29801 ACAATTTGTT ACCTTTCGTT TCCCATTGCT CTCTCTCATA TCCCTCTCTG
29851 AAAAGTCCGA GTCGGCCAGG CACGGTGGCT CACACTGTA ATCTCAGCAC
29901 TTTGGGAGGC CGAGGCGGGA CCATCACTTG AGGTCAGGCG TTCAAGACCA
29951 GCCTGCCCAA CATGGTGAAA CCCCATCTCC ACGAAAAATA CAAAATTAG
30001 CCAGGCGTGG TGGCAGGCGC CTGTAATGCC AGCTACCTGG GAGGCTGAGG
30051 CAGGAGAACG GCTTGAACCT AGGAGGTAGA GGTTGCAGTG AGCTGAGACC
30101 AGGACCCTGC ATTCCAGCCT GGGTGACACA ATGATACTCC ATCTCAAAAA
30151 TATATATATA TATATACACA CACACATATA TATTTGAGTA AATACATGTA
30201 TTAAAATCAA TGCAGCCATA AAAGACAAT TATTGCATGA TTCCACTTAT
30251 ATGAGGTACC TAGAGCAGTC AAATTCATAG AGAGAGAAAG TAAAATGGTG
30301 GTTGCCTGGC GTTGAGGGGA GGAAGAATGC CAAGTTGTTT AATGAGTGTA
30351 AATTATCGGT TTTGCAAGAT GAGTAGTTCT GGAGATTGGT TGCACAACAG
30401 TGAGAATGTA CTTAACACTA CTGAACTTAC ACAAGTATAT ATAAATAGAT
30451 GTAAATTTTA TGGGGTAATT TACCATATGTATG TACATATANN NNNNNNNNNN
30501 ATGTCTTATA TATAGAAATA AATATGTATG TACATATANN NNNNNNNNNN
30551 NNNNNNNNNN NNNNNNNNNN NNNNNNNNNN NNNNNNNNNN NNNNNNNNNN
30601 NNNNNNNNNN NNNNNNNNNN NNNNNNNNNN NNNNNNNNNN NNNNNNNNNN
30651 NNNNNNNNCT CAATTAAAAT GACAGTGTTA ATTATTCAGT GCAGAGACAG
30701 GCAGAGGAGA GCGATGTTAA TGTTATTACA TAGCACACAG AGTAAGAAAC
30751 ATGATAGACT AGACAACATA TGAACATTTA ATATTAGTAA TAAAGTGCTC
30801 AACCTTAAAA AATCAATAAT ACATCTAATT TTCTATTATC TGTGAAATTT
30851 TTAAAAAAGC AGAGCTTAGG GGATCTTATA GACATCCACT TGAACTTTTC
30901 ATCTTAAAGA TGAGGTGATG AGCCTAAGAG AGGTAACAGA TTTTCCCACA
30951 TCAGGAGCAG CTACGGCTTC CCTTTTCATG TGACCTTAGC CACCAACTCT
31001 TTATCTCATT GGCCAAAACG GGTCGCATGG CCTCCCCTGG CTGCACCCAA
31051 AGCTGCCGGG AAAGCAGCAC AAAGAATAGG TTAGACACAT TGCCACCCCA
31101 AACAAATTAG GGTTCCCTCA ACAAGGGAAG AAAAGGAGAA TGTGTATTAC
31151 GTAGGCAGTC AGCAGTGTCT GCTACACTCA CCTTAGTGTC TTTGTTCTGT
31201 GTTGTCTTGT TTTTTGTTTG GGATGTTACA GGCTGGAACC AATGGTTACA
31251 TGGCTCCTGA GATCCTAATG GAAAAGGTAA GTTATTCCTA TCCTGTGGAC
31301 TGGTTTGCCA TGGGATGCAG CATTTATGAA ATGGTTGCTG GACGAACACC
31351 ATTCAAAGAT TACAAGGAAA AGGTCAGTAA AGAGGATCTG AAGCAAAGAA
31401 CTCTGCAAGA CGAGGTCAAA TTCAGCATG ATAACTTCAC AGAGGAAGCA
31451 AAAGATATTT GCAGGCTCTT CTTGGCTAAG AAACCAGACC AACGCTTAGG
31501 AAGCAGGTAA ACTAGCATGT AACAGAGAGG ATTGCTGACA CCAGTATTGT
31551 CCACAGGGAT TAGGAGAATA CTTTTGATTT GTGGCAAAGT CTTGGAATTA
31601 AGTATTATCA TTTTCTTATT TTTATTGCA TATTATATGG TTAAACATTT
31651 CTAATACTTT CAAACACTAT TAGCACTTTG CTATGGAACA ATTTCCCAAG
31701 ATGTATTTTA AGGGAAAAG TGAGGTGCAA AGCAGCTTCC GTTAAAAAAA
31751 GAAAAAACAA TACATAATTC AAATGCTTGT ATAGAACATT TCAAGGAATT
31801 TATAGGATTC CTTATGTCAG ATGAAGGGAA ATTGGGGCT GGGGATGGGG
31851 ATGCAAATAA GAATTTTCAC TGTATCACCT TAGTTTCTTT TGCATCTGAA
31901 CCATGTTGAC TAAATAAATG TATTAAAATC ACATGCAGCC ATAAAACAAA
31951 ACAAATATTA CATGATTCCA CTTATATGAG GTACCTAGAG TAGTCGAATT
32001 CATAGAGACA GAAAGTAGAA GGCCGGGCAG GGTGGCTCAT GCCTGTAATG
32051 CCAGTACTTT GGGAGGCCGA GTCACGAGGTC AGGAGTTCAA
32101 GACCAGCCTG GCCAAGATGG TGAAACCCCA TCTGTAATAA AACTACAAAA
32151 ATTAGCCGGG GGCGGTGGCA GGTGCCTGTA ATCCCAACTA CTCGGGAGGC
32201 TAAGCAGGA GAATCGCTTG AACCCAGGGA GGAGAGGTTG CAGTGAGCCA
32251 AGATCAAGCC ACTGCACTCC AGCCTGGGTG ACACAGTGAA ACTCCATCTC
32301 AAAAAAAAG AAAGAAAGTA AGTAGAACGG CAGTTTCCTG GGCCTAAGGG
32351 GAGGAGAAAT GGGAAGTTGT CTAATGAGTA TAAATTTCT GTTTTACAAG
32401 ATGAAGAGTT CTGGAGATTG GTTGCATAAC AACGTAGTGT GAATGTACTT
```

FIGURE 3K

```
32451 AACACTGTTA CATCATCTAT TCAAAAATAA TTAAAACACG CGGGCACAG
32501 TGGCTCACAC TGTGAGCCAG GCATCGTGGT TCACGCCAGC ACTTGGGAGG
32551 TTGAGGTNNN NNNNNNNNNN NNNNNNNNNN NNNNNNNNNN NNNNNNNNNN
32601 NNNNNNNNNN NNNNNNNNNN NNNNNNNNNN NNNNNNNNNN NNNNNNNNNN
32651 NNNNNNNNNN NNNNNNNNNN NNNNNNNNNN NNNNNNNNNN NNNNNNNNNN
32701 NNNNNNNNNN NNNNNNNNNN NNNNNNNNNN NNNNNNNNNN NNNNNNNNNN
32751 NNNNNNNNNN NNNNNNNNNN NNNNNNNNNN NNNNNNNNNN NNNNNNNNNN
32801 NNNNNNNNNN NNNNNNNNNN NNNNNNNNNN NNNNNNNNNN NNNNNNNNNN
32851 NNNNNNNNNN NNNNNNNNNN NNNNNNNNNN NNNNNNNNNN NNNNNNNNNN
32901 NNNNNNNNNN NNNNNNNNNN NNNNNNNNNN NNNNNNNNNN NNNNNNNNNN
32951 NNNNNNNNNN NNNNNNNNNN NNNNNNNNNN NNNNNNNNNN NNNNNNNNNN
33001 NNNNNNNNNN NNNNNNNNNN NNNNNNNNNN NNNNNNNNNN NNNNNNNNNN
33051 NNNNNNNNNN NNNNNNNNNN NNNNNNNNNN NNNNNNNNNN NNNNNNNNNN
33101 NNNNNNNNNN NNNNNNNNNN NNNNNNNNNN NNNNNNNNNN NNNNNNNNNN
33151 NNNNNNNNNN NNNNNNNNNN NNNNNNNNNN NNNNNNNNNN NNNNNNNNNN
33201 NNNNNNNNNN NNNNNNNNNN NNNNNNNNNN NNNNNNNNNN NNNNNNNNNN
33251 NNNNNNNNNN NNNNNNNNNN NNNNNNNNNN NNNNNNNNNN NNNNNNNNNN
33301 NNNNNNNNNN NNNNNNNNNN NNNNNNNNNN NNNNNNNNNN NNNNNNNNNN
33351 NNNNNNNNNN NNNNNNNNNN NNNNNNNNNN NNNNNNNNNN NNNNNNNNNN
33401 NNNNNNNNNN NNNNNNNNNN NNNNNNNNNN NNNNNNNNNN NNNNNNNNNN
33451 NNNNNNNNNN NNNNNNNNNN NNNNNNNNNN NNNNNNNNNN NNNNNNNNNA
33501 GAAAAGAATG CTACACACTT TGTATTGTTA GAACATGTCC CATTTTGTTT
33551 TGTTAACTCT GTCTCAGGCT GATCATCTCC TTTCTTCACA GAGAAAAGTC
33601 TGATGATCCC AGGAAACATC ATTTCTTTAA AACGATCAAC TTTCCTCGCC
33651 TGGAAGCTGG CCTAATTGAA CCCCCATTTG TGCCAGACCC TTCAGTGGTT
33701 TATGCCAAAG ACATCGCTGA AATTGATGAT TTCTCTGAGG TTCGGGGGGT
33751 GGAATTTGAT GACAAAGATA AGCAGTTCTT CAAAAACTTT GCGACAGGTC
33801 CTGTTCCTAT AGCATGGCAG GAAGAAATTA TAGAAACGGG ACTGTTTGAG
33851 GAACTGAATG ACCCCAACAG ACCTACGGGT TGTGAGGAGG GTAATTCATC
33901 CAAGTCTGGC GTGTGTTTGT TATTGTAAAT TGCTCTCTTT ACCAGACAGG
33951 CAGCAGGAGT CTCGCCTGAC ATAATCCTCG AATGTTCCAC ACGTGGAAAT
34001 CTGTGGAATG AGGGCTAATC AGTTAGGAGG GACATCACAA CCACAAAACA
34051 ATTCAAAAGA CAGGCAAGCT CACTACTAGA ACACATTTTA TTTTCTTTTT
34101 CTTTCTTCAT AAAGATGAGT AAAGTCTCAG TTTCACTGA GGGCAGGGAA
34151 AAGGAACACT CAGGTTTATT TTGATAAACT GAAAGCATCA GCCTTTTACC
34201 ATCATGTCCC TGTGTATTAC GCAAAGTCCT ACGAACAGAG AATGGAACTT
34251 TGTGGTGTGC CCAGAAAATG AGCATTTGCA ATTCTTAGTA AATAATCATT
34301 TTAGTTTTTC TTTGTTTATA TCTTTTTTTC CCTTCATCTT TCTTCGCTTC
34351 TATACTTATA AAAAGGATTT TGAAGCTGGA AACAAATGTT TCTGACATTC
34401 TCCCCCTAAA AAGGAGTCGA TTACAATATT TTGCCAATGT TTTAAATCAC
34451 AGAATAATTT TCAATTTCAG TGACAGTTTC TTTTGCAATT TTGTGGAAAT
34501 AATTTACTAT CATAATGTTG AAGCATTTTA AACATAAACA TCCATGACAT
34551 CTGTGAATTA AAGCATTCTG TAAATTTAGT TGAGTCCTTT AAGTAATATG
34601 GTACAAATTG CTTCAACTTG CACTACCATA TGCCATCGGT TCCCAAACTC
34651 TGCTCAACTT TGGAATCATC TAGGGATCTT TTAAAAAACT AATGCCTGAT
34701 TCCCATCCAT AGACATTCTG ATCCCCACTC CCAGGTATGA GAACAGCTTG
34751 ACCATTTAGA ATTTCAGAAG CTCCCCAGGT GATTCTAATG TGCAGCAGAG
34801 TTTGGCAGCC ACTGCTGTGC ACATTTGAAT GTTATTACAT TCAATCTTAT
34851 TTTGGTTGCT CAAAACTTCA ATCATACATT TTGATGGCAA CTTTTCAAAT
34901 GTCCCCAAAG CATGTCATTT TAGTAATTGC AGTATAAATG AAACAAGACA
34951 GTCTATTCAT CTTATGGCTT CTCTTGTCCT TGCACACTTT AGTTTCTCAC
35001 ACGTATCTTG GGAGCTCGGT CTCTTGGCTA TTTCAAGTCC TGAAGGAGAC
35051 CTATGGGCTT ACAAATTGAG TTGAACACGC CAGGTGCGGT GGCTCATGCC
35101 TGCAATTCCA GCACTTTGCG AGGCCAAGGC AGATGGATCA TGAGGTCACG
35151 GGCTCAAGAC TAGCCTGGCC AACATGTTGT AAACCCGTC TCTACTAAAA
35201 ATACAAAAAT TAGCCGGGTG TGGTGGTGCA CATCTATAAT CCCAGTTACC
35251 CGGGAGCCTG AGGCAGGAGA ATTGCTTGAA CCCAGGAGGC GGAGGTTGTA
35301 GTGAGCCAAG ATCGCAACAT TGCACTCCAG CCTGGGCAGC AAGAGCAAGA
35351 CTCTATCTCA AAAAAAAACA AAACAAAACA AAACAAAAAA AACAGAAAAG
```

FIGURE 3L

```
35401 AAATTCAATT GAAAAATAC TAACCATCAT TTCAAGTGCC TGTCAGTGA
35451 ACACTGTATG GTAGAATTAG GACTTCTCAA AAGCACAGTC AAGGTGACAA
35501 TTCTACAGCT GCGAAAAAAT ATTTGGCATA CAAATATAAA GCTGACTGAT
35551 ATTTTTTAAA AGGATGTATG TGCACATAAT AAAATCTAAA TTTATCCCAC
35601 TGGTAAAAAA AACCTGGCTG AAGTCAGTTT AAAAGTTTTG TCCCTGACT
35651 TAAGGATTCA AGAGCTGCAA AAGTGCCGGT CAAAAAAATG TTGGTTAACT
35701 GGAATCTGAA TAACAGTAAT ACTCATCTAC AAGACAGCAT TAACTACACC
35751 TGCAACAAGT TAAGAAGAAG CCCTCTGACA GTTGAGGCCT CGGCCGGTGC
35801 ACCTGCGGCT CACTTTCCCG CTCCTCCTCC ATCCTCAGCA TGCTCCCTAA
35851 TGCTCCAAAT CCTAACCTAG GATGCTTAGA TTTCTGTGTC ACCAAAGCAG
35901 GATAGAAGTG TGCCCAGGAG ATTTTTTTTT TTCCTGAACT AAGAAAGTAA
35951 ATTAAAGTTT GGTTAAGTTT TCAACAAGTC CCTTTTAACA AAAAAACTGA
36001 TTGGTGATTA ACAGAAATCC AATTAACCAG AGCACTCCAA TGGTAGAGTT
36051 CTCAGGATTG GGCTTTATAG ACGTTAGACA TTTAAAAACA ACATTGTTA
36101 TTTGTTGATT ATGCCTTAAA GCTGGCAGAG GGACAAATGC AAACTAATAA
36151 TTAAAGATAA ATATCTCAGT TTTTAAAAGG ACAAAAATT TGGAGAGATA
36201 AAAAAATAAA AATGTCTTGT TGCATTGGTT CCTTAGTGTG AATTGCCTCT
36251 GCTTTCAATA AACTTTAAAT GCAAATCTGT TTATATCTT AGAACTAACT
36301 TAGGAAAATA ACTGAATAAG TAGTTGTATT AATCCATTCT CACACTGCTA
36351 TAAAGAAATA CCTGAGGCTG GCCATGGTGG CTCACGCCTG CAATCCCAGC
36401 ACTTTGGGAG TCCAAGGCAG GCAGATCACC TGAGATTAGG AGTTTGAGAC
36451 CAGCCTGGCC AACATGGTAA AATCCTGTCT CCACTAAAAA TATACAAATT
36501 AGCCAGGTGT GGTGGTGTGT GCCTATAATC CCAGCTACTA GGAAGGCTGA
36551 GACAGGAGGA TTGCTTCAAC CTGGGAGGAG GAGGTTGCAG TGAGCCGACA
36601 TTCAGCCACT GGACTCCAGC CTGGGTGACA GAGCAAGGCT CTGTCTCAGA
36651 A (SEQ ID NO:3)
```

FEATURES:
Start: 2076
Exon: 2076-2687
Intron: 2688-4164
Exon: 4165-4602
Intron: 4603-31231
Exon: 31232-31506
Intron: 31507-33591
Exon: 33592-33925
Stop: 33926

CHROMOSOME MAP POSITION:
Chromosome 3

ALLELIC VARIANTS (SNPs):

| DNA Position | Major | Minor | Domain | Protein Position | Major | Minor |
|---|---|---|---|---|---|---|
| 2022 | T | A | Beyond ORF(5') | | | |
| 3672 | T | C | Intron | | | |
| 3884 | C | T | Intron | | | |
| 4986 | C | T | Intron | | | |
| 5268 | T | C | Intron | | | |
| 7344 | C | T | Intron | | | |
| 7414 | T | C | Intron | | | |
| 8113 | G | A | Intron | | | |
| 8394 | C | T | Intron | | | |
| 9233 | C | A | Intron | | | |
| 9255 | A | T | Intron | | | |
| 9747 | C | T | Intron | | | |
| 9747 | - | A T | Intron | | | |
| 11635 | - | A T | Intron | | | |

FIGURE 3M

| | | | | | | | |
|---|---|---|---|---|---|---|---|
| 13721 | T | A | | Intron | | | |
| 13884 | C | G | | Intron | | | |
| 13987 | A | C | | Intron | | | |
| 14377 | T | - | | Intron | | | |
| 15045 | T | G | | Intron | | | |
| 15742 | A | G | | Intron | | | |
| 17482 | A | G | | Intron | | | |
| 17688 | A | G | | Intron | | | |
| 17992 | T | C | | Intron | | | |
| 19133 | - | C | | Intron | | | |
| 20105 | A | G | | Intron | | | |
| 24195 | A | - | | Intron | | | |
| 24220 | - | A | T | Intron | | | |
| 24278 | A | G | | Intron | | | |
| 30132 | T | C | | Intron | | | |
| 33800 | C | A | G | Exon | 512 | P | T A |
| 33800 | A | G | | Exon | 512 | T | A |
| 34513 | A | T | | Beyond ORF(3') | | | |
| 34821 | A | G | | Beyond ORF(3') | | | |
| 34983 | C | A | | Beyond ORF(3') | | | |
| 35153 | C | T | | Beyond ORF(3') | | | |
| 35153 | T | C | | Beyond ORF(3') | | | |
| 36368 | C | T | | Beyond ORF(3') | | | |

Context:

DNA
Position
2022     GGACCAGTGCGGGAGGTGGCCCCGGCAGGTCTCCCAGCAGCTTTCGCCTTGGCAGGTGGG
         AGCATCACCTATCGTGTGCAGTTCCTGGCGGGCTATACATAGCCAGTTAAAGCTTCTTAC
         AAGAGAAACCTCTTTCACACCCTCCACGGGTCCCACCCACAGCCCACACGACTCACTGTA
         AATCCCTTGGACGTTGTCTCACCCGGGAAGGGAAAGCAGCC
         [T,A]
         GCAGCCCTCCAGCCCTCTTGTGCTTTCCCTGGGAGTCCGCCCCGTGCTCAGCCATGGTGG
         ACATGGGGGCCCTGGACAACCTGATCGCCAACACCGCCTACCTGCAGGCCCGGAAGCCCT
         CGGACTGCGACAGCAAAGAGCTGCAGCGGCCGGCGTAGCCTGGCCCTGCCCGGGCTGC
         AGCGCTGCGCGGAGCTCCGGCCAGAAGCTGTCCCTGAACTTC 3672     TACAATGCAGTGGCACTTCGCACAAATGCAATGTTGGGTAAGCAACACCTCAATCTGGAT
         CCAAGACACTCTCATCACCCCTGTGCCCATTAATACTCCCTCCCCATCCCTCTCCTCCTC
         CAGCCCTGACAACCACTAGTCCGGCTTTCTGTCTCTAGGGATTTGCCTATTCTGGGTGTTT
         CACACAATATGTGACCTTTTGTGTCTGGCTTCTTTCACTCATTAGAATGTTTTTGGGGTT
         CATTCACACTGTAGCATGTGTCAATACTCCATTCCTTTTTATGGCTGTATAATATTCCAT
         [T,C]
         GTATGGATGTACTACATTTCATGTAGCCATTCATCTGTTGATGGACACTTGGGCTGTTTT
         CACCTTTTGGCTATTGTGTATGGTCCTGCTATTCATGCACAAGTATTTGTTTGAATCCTT
         GTTTTCATTTCTCTTGGATTTATGCCCAGGAGTGGAATTGCTAGGGCATATGGTGATACT
         ATGTTTAACTTTTCAAGGAGCCACCAAACTCTTCCACATTTTTTATTCCCACCAGCAATGC
         TTAAAGGTTTCGATTTCTCCACATCCTTGCCAACACTTGATATTTTCCTGTATTTTTTA 3884     TTTCACTCATTAGAATGTTTTTGGCGTTCATTCACACTGTAGCATGTGTCAATACTCCAT
         TCCTTTTTATGGCTGTATAATATTCCATCGTATGGATGTACTACATTTCATGTAGCCATT
         CATCTCTTGATGGACACTTGGGCTGTTTTCACCTTTTGGCTATTGTGTATGGTGCTGCTA
         TTCATGCACAAGTATTTGTTTGAATCCTTGTTTTCATTTCTCTTGGATTTATGCCCAGGA
         GTGGAATTGCTAGGGCATATGGTGATACTATGTTTAACTTTTCAAGGAGCCACCAAACTT
         [C,T]
         CCACATTTTTTATTCCCACCAGCAATGCTTAAAGGTTTCGATTTCTCCACATCCTTGCCA
         ACACTTGATATTTTCCTGTATTTTTTATGAAGGCCTGCCTAGTGAGCTGAAGGAGTATC
         GCACTGTAGTCCCCA

FIGURE 3N

```
4986  GAGCCTTGGACTTAATTCTTTTGCTTTTTTTTCCTAAAGGGCTTAAGTTCTCATCTTGCC
      TTAACATGACTGGTCTAAGAGGATTAGATTCATTGGCTATTTCAGGGCTACTTTGCTCTC
      CTCTCACAGGGGATGGGGGAGCCTCCTTTGTCAGTTGGGGATGGCCTCTGCTTTTGTGAT
      GAGATGCAAAAAGCTGAATCCATAGTCATGGTCCGGGTGTGTGCAATAACCACCTCTATGC
      TGCTCTCCTCCTGAGCCAATAGAGCCTTGGCTTCCTTTTCCTGGAAAATGAAGGGGCTGGA
      [C,T]
      CCTAAAATTCCATGATCCTAGGAGGTAAACTTTAATCAGATAAGAAAAGAATGATCCGG
      CTGGGTGTGATGGCTCACGCCTGTAATCCCAGCACTTTGGGAGGCCGAGGCGGGTGGAT
      CTGCTGAGGTCAGGAGTTTGAGACCAGCCTGGCCAACATGGTGAAACCCCATCTCTAGTA
      AAAATACAAAATTAGCCAGGCATGGTGACAGGCGCCTGTAATCCCAGCTACTCGGACG
      TTGAGGCAGCAGAATCGCTTGAACCCAGGAGGCGGAAGTTGTAGTGAGCCGAGATCATGC

5268  GAAAATGAAGGGGCTGGACCCTAAAATTCCATGATCCTAGGAGGTAAACTTTAATCAGAT
      AAGAAAAGAATGATCCGGCTGGGTGTGATGGCTCACGCCTGTAATCCCAGCACTTTGCC
      GACGGCCGAGGCGGGTGGATCTGCTGAGGTCAGGAGTTTGAGACCAGCCTGGCCAACATGG
      TGAAACCCCATCTCTAGTAAAAATACAAAAATTAGCCAGGCATGGTGACAGGCGCCTGTA
      ATCCCAGCTACTCGGGAGGTTGAGGCAGGAGAATCGCTTGAACCCAGGAGGCGGAAGTTG
      [T,C]
      AGTGAGCCGAGATCATGCCACTGCACTCCAGCCTGCTCGACAGAGCAAGACTCTGTCTCA
      AAAAAAAAAAGAAAGAAAGAAAAAGAAAAAAAATAAAGAAAGAAGGAAAAG
      AATGATCCTCTCACACCTAGAACATTAAAAGTAAAATATCTCCTTTCCTGTTTAGTGTGG
      AATGGGCGAATGTTTTGCATTGGATGAAGATGATATTTTAAATGAAAATATATGGAAGAA
      AACAAAGGCAACTGATGTTTATTTTAATCAGTTTTGTTCAAAGTGACTTGCTTAAAATTC

7344  CTGACAAATGACATTCTTGAAAATTCTTTGGTTAAAAAGGGAATTATAACTAAGCGATTA
      TAATTACTGAATTATATCTGGGCTGAGGAGAAGATCACCCGGCTCATGTCCAGGCCATGT
      GTGCCCACGTTGTAGATGTGGAACTTGAGGCAGGGGTGAAGGAGCGGGTTCTAGTTAGTA
      AGGATGAAGAACAGCTGGATATTGAGCAGGTAACTAGCAGCCTCTGCCACAGGAGCCAAA
      CAAGAGGATTTCAGGGAGGAAAGTGTGGTCAAAGTGTCAAGTGTTGCAAAGAGGTAACGT
      [C,T]
      GCCTGTGGGATTTGGCAATTAGGAAATCAGTGTAAGGGAATGGTGAGGTCTCAATTCAGA
      CTCTGGAGGTTGGATTGATCTAGAAGTAGGGAATGAGACTCTGGAAGGCCGAGACTGGTC
      CCTAGAAGGGGATACAGTGGGGAAATGGAGTTTTGAGATGGGCAGGGCAGAGCGGGTTTA
      GATGCTGAGGCAAAAGCCAGCAGAGTAGGTGTTGATCCTGTGGGAAGGAAAGACAGTAGA
      TGATGGCAGACAATGTGGGGAGGAGCTCAAGTAACACCGTCTCCTCTGTGGGTCGGAAGG

7414  ATTATATCTGGGCTGAGGAGAAGATCACCCGGCTCATGTCCAGGCCATCTGTGCCCACGT
      TGTAGATGTGGAACTTGAGGCAGGGGTGAAGGAGCGGGTTCTAGTTAGTAAGGATGAAGA
      ACAGCTGGATATTGAGCAGGTAACTAGCAGCCTCTGCCACAGGAGCCAAAGAAGAGGATT
      TCAGGCAGGAAAGTGTGGTCAAAGTGTCAAGTGTTGCAAACAGGTAACGTTGCCTGTGGG
      ATTTGGCAATTAGGAAATCAGTGTAAGGGAATGGTGAGGTCTCAATTCACACTCTGGAGG
      [T,C]
      TGGATTGATCTAGAAGTAGGGAATGAGACTCTGGAAGGGGCAGACTGGTCCCTAGAAGGG
      GATACAGTGGGGAAATGGAGTTTTCAGATGGGGAGGGCAGAGCGGGTTTAGATGCTGAGG
      CAAAACCCAGCAGAGTAGGTGTTGATCCTGTGGCAAGGAAACACAGTAGATGATGGCAGA
      GAATGTGGGGAGGAGCTGAAGTAACACCGTCTCCTCTGTGGGTGGAAGGACGAGCAGGC
      CAGGGAGGTGACACAGTGTTTGCCTCCTTGGGACATTCCTATGAACACAGGAACGCTGTG

8113  TTCTGAGTCCCCCATGGACATGTATCACACTAATTGTTCCTATATCTCGACCTTGCTGGA
      GGCTTAGGGGACACATACAGCTTTGGCTCACTCCAGTCTCCTTTCTCAGTCTCCTCAGGC
      TCTGTTCATGGGCCATGGCCATTTGGAAGGACAGCTCCTTCCTTGGCTCCCGGGTGCAGC
      TCTCTGGCTCATCTGGAACGTGCAGGAAGGTTTCTGTGCCTCCCCAGTGCTGTCCGCTAC
      CAGGAACGTACTTAGTAGAGAGGCTCACTGCCTACAGACCTTTGGCCCTTTTACCTCTGC
      [G,A]
      TCCCTCTCCGTCCCGTGACACCACACTTCAGGGTTTAGGCCACTTGCCTCATCCAAGAAG
      TTTTATGCCCCACTTTCCGGGCCTGCCACGGAAGCCAGGGGACCATCAGGAAGGGTGAG
      GGGAGAGAGATGGAGAGCAAGATTGAAACCCATAAAAAACAAAGAGAAGAGAAGGAAGG
      CCTCCTTTCTTCACTGTTTACCCTTCTACACAGCTAAGTAAACCCCCTAGTTTCCTATT
```

FIGURE 3O

```
              CATTGCAGCTCCCACACATATAATTGGGCTCACAACTAGACTGTAAGGTCATTATATTCA
     8394     TTGGCCTTTTTACCTCTGCGTCCCTCTCCGTCCCGTGAGACCACACTTCAGGGTTTAGGC
              CACTTGCCTCATCCAAGAAGTTTTATGCCCCAGTTTCCGGGCCTCCCACGGAAGCCCAGG
              GGACCATCAGGAAGGGTGAGGGCAGAGAGATGGAGACCAAGCATTCAAAGCCATAAAAAAC
              AAAGAGAAGAGAAAGCAAGGCCTCCTTTCTTCACTGTTTACGGTTCTACACAGCTAAGTA
              AACCCCCTTAGTTTCCTATTCATTGCAGCTCCCACACATATAATTGGGCTCACAAGTAGA
              [C,T]
              TCTAAGGTCATTATATTCACAACATTTCACAGAAAAAAAGACATATCATAGTTACAGGG
              CTTCTCTAACCACTAACGTTCAGTTGTGATGTCAACATACTGTGTTAGAGAATTACTGTG
              AACATTAATTCTGTGGTTTGAATGAGTCCTCAAAATTTGATGTGTTGGAAACTTAATCTC
              CAATGTGGCAGTGTTGGAGAGGTGGGGCCTTTAAGACGTGAGTGGACCATGAGGGCTCTG
              CCGCTGTGAATAGATGAATGGATTAATGGGTTATCACACGAGTGGAAATGGTAGCTTTAT
     9233     ACCCTGATGATGGAGCTTGAACTCTGCATTGAGTCTGAGCAGTTCTTCCAGAAAAGTTAA
              GGCATCATGGCTTTGGAAATTTGGCTAGCTTTTTCTCATTCAGAGAGTTATTTAGTCTTG
              TATAAGTTGGGATTTCTTTCTACTAAATATAACAGAATACCAGATTTTGGTATAGATTTG
              GCTGTTCAGCAATTTCACGGACAAGACCTCTGTTAAAAATCTCCTGGCTTGCGCTGGGTG
              TGGTGGCTCAGGCCTAATCCCAGCACTTTGGGCCCAGCAGGACAAGACCAGTCAATAGTG
              [C,A]
              GAACCCCATCTCTTAAAAAAATTTTTTTGTTTTGTTTTAGGCTGGCCGTGGTGGCTCAC
              ACCTGTAATCCCACACTTTGGGAGGCCAAGGCAGGTGGATCCCCTGAGGTCAGGAGTTCG
              AGACCAGCCTGGCCAACATGTTGAAACCCTGTCTCTACTAAAAATACAAAAATTAGCCAG
              GCATGGTGGTGGGTGCCTGTAATCCCAGCTACTTGGGAGGCTGCTGTGGGAGAATCATTT
              GAACCCGGAGGTGGAGGTTTTAGTGAGCCAAGATCATACCACTGCACTCCAGCCTGGAT
     9255     TCTGCATTGAGTCTGAGCAGTTCTTCCAGAAAAGTTAAGGCATCATGGCTTTGGAAATTT
              GGCTAGCTTTTTCTCATTCAGAGAGTTATTTAGTCTTGTATAAGTTGGGATTTCTTTCTA
              CTAAATATAACAGAATACCAGATTTTGGTATAGATTTGGCTGTTCAGCAATTTCACGGAC
              AAGACCTCTGTTAAAAATCTCCTGGCTTGCGCTGGGTGTGGTGGCTCAGGCCTAATCCCA
              GCACTTTGGGCCCAGGAGGACAAGACCAGTCAATAGTGCGAACCCCATCTCTTAAAAAAA
              [A,T]
              TTTTTTTGTTTTGTTTTAGGCTGGCCGTGGTGGCTCACACCTGTAATCCCACACTTTGGG
              AGGCCAAGGCAGGTGGATCCCCTGAGGTCAGGAGTTCGAGACCAGCCTGGCCAACATGTT
              GAAACCCTGTCTCTACTAAAAATACAAAAATTAGCCAGGCATGGTGGTGGGTGCCTGTAA
              TCCCAGCTACTTGGGAGGCTGCTGTGGGAGAATCATTTGAACCCGGGAGGTGGAGGTTTT
              AGTGAGCCAAGATCATACCACTGCACTCCAGCCTGGATGAAAGAGAAGAGTCTGTCTCA
     9747     TGCGACGGCTGCTGTGGGAGAATCATTTGAACCCGGGAGGTGGAGGTTTTAGTGAGCCAAG
              ATCATACCACTGCACTCCAGCCTGGATGAAAGAGAAAGAGTCTGTCTCAAAAAAAAAAA
              AAATTGTTTTAAACTTAGCCAGGTGTGGTGATGCATGCCTGTGGTCCCAGCTACTTGGGA
              GGCTGAGGTGGGAGGATTGCTTGAGCTCAGCAGTTCAAGGCTTCAGTGAGCTATGATCAT
              GCCACTGCACTCCAGCCTGGGTGACAGAACAATACCCTGTCTCAAAAAAAAAAAAAAAAA
              [C,T]
              CTTTTGGCCTTTTCCTCCTTGTCACAAGTGGCTGTTGCAACTCCAAATATTGAGTCTGCA
              TTCCAGGAGAAGAAAAAGAGGAGAAAAGAACAACATCCACAGATACCTGCTTATAGCCC
              ATTAGCCAGGACCATGTCATATGTTCACTTCTAGCAGCAAAGGAGGCTCAAAAATAGAGT
              ATTTCATTTTCCAGCCTCTGTTTTGGGGGATGTTAAAGGAGAGGAGGAATGAGATTAGCT
              GTTGGGTGAGCTGACAGCATCTGCCACACCAGGCCCAGGAAAAAATATTGATGAGGAT
     9747     TGCGAGGCTGCTGTGGGAGAATCATTTGAACCCGGGAGGTGGAGGTTTTAGTGAGCCAAC
              ATCATACCACTGCACTCCAGCCTGGATGAAAGAGAAAGAGTCTGTCTCAAAAAAAAAAAA
              AAATTGTTTTAAACTTAGCCAGGTGTGGTGATGCATGCCTGTGGTCCCAGCTACTTGGGA
              GGCTGAGGTGGGAGGATTGCTTGAGCTCAGCAGTTCAAGGCTTCAGTCAGCTATGATCAT
              GCCACTGCACTCCAGCCTCGGTGACAGAACAATACCCTGTCTCAAAAAAAAAAAAAAAAA
              [-,A,T]
              CTTTTGGCCTTTTCCTCCTTGTCACAAGTGGCTGTTGCAACTCCAAATATTGAGTCTGCA
              TTCCAGGAGAAGAAAAAGAGGAGAAAAGAACAACATCCACAGATACCTGCTTATAGCCCC
              ATTAGCCAGGACCATGTCATATGTTCACTTCTAGCAGCAAAGGAGGCTCAAAAATAGAGT
```

FIGURE 3P

```
        ATTTCATTTTCCAGCCTCTGTTTTCAAGTATGTTAAAGGAGAGGAGGAATCAGATTAGGT
        CTTGGGTGAGCTGACAGCATCTGGCACACCAGGCCCCAGGAAAAAATATTGATGAGGAT

11635   AACCTGGGAGGCACAAGCTTGCAGTGAGCCAAGATTGCGCCACTGCACTCCAGCCTGGGC
        AACAAAGTCACACTCTGCCTCAAAAAAAAAAAAAAAAAAAATTAATAGACAAGATATCAA
        CGTGCTGGACACTGTTAGAGGGATAATATTTTCCTTTCTCACAGGAATCAGAATACCTAC
        CACCAGTCAGGTGCTGTGACTCACGCCTGTAATCCCAACACTTTGGGAAGCCAAGGTGGG
        AGAATCGCTTGAGGCCAGAAGTTTGAGACCAGTCTAGGCAACATAGCAAGACTTTGTCTC
        [-,A,T]
        TAAAAAAAAAAAAAAAAAAAAATTACCTGGGCATGATCCTATGCACCTGTAATCCCAGCTAC
        TCAGGAGGCTGAGGCAGGAGGATTGCTTGAGCCTGGGAGTTTGAGGCTGCAGGTAGCCGT
        GATCACACCACTGCACTCCAGCCTGAGTGACAGAGCAAGACCTTGTCTCTAAACAAACAA
        ACAAACAAAAAACGAGAACAAAAACAAATAATACCTACTGCCTATTTTAATAGAACTGGA
        GGCTGTAATTGAATTTAGAACTTTGGACATGAGTCTTCCAAGTGGGTAACTCTTCCCTGG

13721   TGCAAAAGATGGGGACTGGATGCCAAATGGGCAAAAAAAAAAAAAAAAAAAAAAAAAAAA
        AACACAAAACAGTGGAGGCCCCTAATAACTGCTGTTACCTCAATGGTTTGAAAAGTTTAA
        AACCTTTCTGACCCCTTAATCACGGGATGATGAGACCTAAGAGTTCCAAGTAGGTAACTC
        TTTTCTACATATGAGCTGAGCCTCTTGGGACCCTTTACAAAAGATTCTGAGTTAGGTAC
        TGTTCTGAGCTCCATTGTACAGGTAGGCAAATTGAGACCCAAAGTCACAGTACTAGTATG
        [T,A]
        GATATGATTCCAGGCACATCAGATTTAAAAGCGCTCACAGTTTTGACTCCATCTTATTGA
        GTTCATGCACATGGCAACATATAGCCTTATGTTTTTTTGTTTGTTTGTTTCAGACAGAGT
        CTCACTCTGTAGCCCAGGCAGGAGTGCAGTGGCACGATCTCAGCTCACTGCAACCTCCGT
        CTCCCAGGTTCAAGTGATTCTCCCGCCTCAGCCTGCCGTGTAGCTGGGATTACAAGCGCA
        TGCTACCACGCCCAGCTAATTTTTTGTACTTCTAGTAGAGACAGGGTTTCACCGAGTTAA

13884   CCATCTTATTGAGTTCATGCACATGGCAACATATAGCCTTATGTTTTTTGTTTGTTTGT
        TTGAGACAGAGTCTCACTCTGTAGCCCAGGCAGGAGTCCAGTGGCACGATCTCA
        [C,G]
        CTCACTGCAACCTCCGTCTCCCAGGTTCAAGTGATTCTCCCGCCTCAGCCTGCCGTGTAG
        CTGGGATTACAAGCGCATGCTACCACGCCCAGCTAATTTTTTGTACTTCTAGTAGAGACA
        GGGTTTCACCGAGTTAACCAGGGTGGTCTTGATCTCCTGACATGATCTGCATGCCTCGGC
        CTCCCAAAGTGCTGGGATTACAGGCCTGAGCCACCGCACCCAGCCAGCATTATGGTTTTT
        AATGCTATAAAAGGCTTTTCACTTAGTAAGACTCAGACAGAATAAGTGCATGTGATGACA

13987   CCATCTTATTGAGTTCATGCACATGGCAACATATAGCCTTATGTTTTTTGTTTGTTTGT
        TTGAGACAGAGTCTCACTCTGTAGCCCAGGCAGGAGTGCAGTGGCACGATCTCAGCTCAC
        TGCAACCTCCGTCTCCCAGGTTCAAGTGATTCTCCCGCCTCAGCCTGCCGTGTAGCTGGG
        ATTACAAGCGCATGCTACCACGCCCAGCTAATTTTTT
        [A,G]
        TACTTCTAGTAGAGACAGGGTTTCACCGAGTTAACCAGGGTGGTCTTGATCTCCTGACAT
        GATCTGCATGCCTCGGCCTCCCAAAGTGCTGGGATTACAGGCCTGAGCCACCGCACCCAG
        CCAGCATTATGGTTTTTAATGCTATAAAAGGCTTTTCACTTAGTAAGACTCAGACAGAAT
        AAGTGCATGTGATGACATTAGCATATCTTCCCAGTCTGGTCTGATATCCACACCAACCAC
        AAGCCTAGCTGAACTTCTAAGAAAGGAAGACTTCAGAAAAGGATCAGCCCCACCTACACA

14377   TGCGATTACAGGCCTGAGCCACCGCACCCAGCCAGCATTATGGTTTTTAATGCTATAAAA
        GGCTTTTCACTTAGTAAGACTCAGACAGAATAAGTGCATGTGATGACATTAGCATATCTT
        CCCAGTCTGGTCTGATATGGACACCAACCACAAGCCTAGCTGAACTTCTAAGAAAGGAAG
        ACTTCAGAAAAGGATCAGCCCCACCTACACAGGGAATGACGGCCATTAATATTTCAGAGC
        CAGCTTCTTACCCATAGGTGCAGCACAATTAAACATGTTCCAGCCACTGTCTACATGCAC
        [T,-]
        TTTTTTTTTTTTTTTTTAGATGGAGTCTTGCTCTGTTGCCCAGGCTGGAGTGCAATGGCAC
        AATCTTGGCTCACTGCGACCTCTGCCTCCAGGGTTCAAGCAATTCTCATGCCTCAGCCTC
        CTGAGTAGCTGTCATTATAGGCACCCACCACCACACTCGGCTAATTTGTGTATTTTTAGT
        ACAGTCGGGGTTTCACCATCTTGCCCAGGCTGGTCTGGAACTCCTGACCTCAGGTGATCT
        GCCCACCTCGGCCTCTCAAAGTGCTGGGATTACAGGCGTAAGCCACCGCGCCCGGTCAAC
```

FIGURE 3Q

```
15045   AAACTACTTTCTATCATTCTAAAACATTCCAACTAAATATAATAGGAATATTGGGAGTG
        AGGATCATGCTTGTACTTTTAAATTCAGAATTCTATTTCCTGAGCAGTGACCTTGAGGT
        ATTATGCAATATGAGTCTTTAAAATTTGCTATTTTGTTAGCAATGGCAATGAGGTTAGAA
        TAGTGACCCAGAAGCTTGTTACATGTTTAGATACCTGGTCCTGCCTTGAAGTCTCTGACC
        AACTCCTCACATTCAGAGGGATAATGGGAGATAGAGGTTTGGTATTATATTTATTTCGAA
        [T,G]
        CATCTATTGTACCAAATACAATGCTACAGACATACTGGAAAGGTGATTTTTAAAAGACCT
        CTGAACATGTTTTCTTGGGAGTTAATGCCTCTATATGTCACAACCATCATGACCATGCCC
        CCCAGTTTTTTTTTCTTTAAGTGCTCACTTCTGAGATCTAGCTTAAGAAAGACATACAG
        GAGAGGCATTCTGGTCACATCAGGCATGAAGTCATGGTCACACTTTGGCCTGACCAAAAG
        GATTACCACCAGCATTGACCAAATTTAATTCCTACTAACTTTTGACCCCTACAGAAATTT

15742   TGCCTTTATTCACTCACTCACTCACTTGTTTATTCAACTTACATGTATCAAGTGTTTCCC
        ACATCCCAGGACTGTTCTAAATATGAGGGATAGCCAGGTGCCGTGGCTCATGCCTGTAAT
        CCCAGCACTTTGGGAGGCCAAGGTGGGCAGATCACTTGAGGTCAGGAGTTTCAGACCAGC
        CTGGCCAACATGGTGAAAACCTGTATCTACTAAAAATACAAAAATTAGCTGGGTGTGGTG
        GCGGGCCCCTATAATCCCAGCTACTTGGGAAGCTGAGGTAGGAGAATCGCTTGAACCCGG
        [A,G]
        AGGCGGAGGTTGTAGTGAGCCGAAATCATGCCATTGCACTCCAGCCTGGGAGACAGAGCG
        AGACTCCATCTAAAAAAAAAAAAAAAAAAAAAA

17482   CATCCAGCTCGCATCTGCTGCAGAATGGATTGCTGGCTGGTTTGTGTTTTGAGAGTATTG
        TGGGAGAAACTGAGTTTGTTTCTTCTACTCAGGAGTGCTCTCCTGAGATGCAGCCATGAG
        GAAGGCAGGACTGGGCAGAGAGAACCTCACCCCTAGTGCGGCAGGCGGTGGGGACTAAGA
        CCTCAGCCATCCTTCAGGGAGCTCTGGAGTTGGGATGACTCTTCTGAGTTGGCCCAAATT
        GAGGTGGGGTCCAGACTTGTGTATCCCTAAGGATGCAGTCAGTGACTGTCAGTAGCTGCC
        [A,G]
        GAAGGGGGCGGAAGCCTGGGATGCCATCCCCGCTGCAGAAGGCAGTTCCCAGGGAGGGGT
        GCAGCTCTGAGCCATCAGCAAGCAGTCGCCCAGCCAGGCATGGCTGCATAAATTTGGGG
        GCTCACTGTGAAATAAAAATATAGGGCCTCTTCTTCAAATATCGGGAAAAAGCCTCCTTT
        CATGCTCTATTTTTCAACCAGCCATAGGGTTTGGATTTGCTATTTAATGTCATACTTCCC
        CAGGCTCTGGGATACTCAAAGAGTGAGTAGAGACCCTCACAGACACCCAGGGCTCCAACC

17688   GAGTTGCCATGACTCTTCTCAGTTGGCCCAAATTGAGGTGGGGTCCAGACTTGTGTATCC
        CTAAGGATGCAGTCAGTGACTGTGAGTAGCTGCCAGAAGGGGGCGGAAGCCTGGGATGCC
        ATCCCCGCTGCAGAAGGCACTTCCCAGGGAGGGGTGCAGCTGTGAGCCATCAGCAAGCAG
        TGGCCCCAGCCAGGCATGGCTGCATAAATTTCGGGGCTCACTGTGAAATAAAAATATAGG
        GCCTCTTCTTCAAATATCGGGAAAAAGCCTCCTTTCATGCTCTATTTTTCAACCAGCCAT
        [A,G]
        GGGTTTCGATTTGCTATTTAATGTCATACTTCCCCAGGCTCTGGGATACTCAAAGAGTGA
        GTAGAGACCCTCACAGACACCCAGGGCTCCAACCCACGACTGGACCTGAGGAAGCATGTG
        CCTGACCCCAGCCCTCCCTGCACCTGAGTCCAGGCCCCTACCAGGCAGAAAGTGGCAATA
        GTCACTGGGTGAGGGTGGGGGTAGAAGTGGGAGGTGGGGAAGCAGACAGCCATGAACCCA
        TCCCCGGGAGCCAACCAGGTGGCAGGAGGGGGACTGTGTGAGCTGAGGCTCCAAGTACGG

17992   TTTGGATTTGCTATTTAATGTCATACTTCCCCAGGCTCTGGGATACTCAAAGAGTGAGTA
        GAGACCCTCACAGACACCCAGGGCTCCAACCCACGACTGGACCTGAGGAAGCATGTGCCT
        GACCCCAGCCCTCCCTGCACCTGAGTCCAGGCCCCTACCAGGCAGAAAGTGGCAATAGTC
        ACTGGGTGAGGGTGGGGGTAGAAGTGGGAGGTGGGGAAGCAGACAGCCATGAACCCATCC
        CGGGCACGCAAGCAGGTGCCAGGAGGGGGACTGTGTGAGCTGAGGCTCCAAGTACGGCTC
        [T,C]
        ATTGGCTTATTGGACTTCACTTAAAAGACACAAATTCAAAGATAAATGATTACAAACAGC
        ATTAAACCCAGTAAAGGTATGCCTCTGAGCACAGGGCCCTGTCCATGGGCACTGGAAAC
        TGGCCTCGCACCAGCAGCTGGAGGCTGGGGGCCAAGAACCTGAAGAGGGGATTGGAGCCA
        AGTAGCCCCCACAGGTGGGGAAGAGCATTTCAGGCCATGGGAATAGCCTGGCCAACTATC
        TCTTCCTTTACGGGAAATGAAAAGCAAGCCAGGAAATGAAAAGCACATCGTAAGAGGAAA

19133   TGTGATCAGGGTTGTCTGACCTGGGTACATAGGAAGGGCACCCAGCCCAACATGAGCACC
        TGGAGTCACAGGGTCAGGAAGGGCTTCCAAGGGCAAGGGACAACCAAGCTAAGACTTAAA
```

FIGURE 3R

```
           AGACATGAAGCCAGACAGGTAAAGATGAAGGAGCATCCGCTAGCTAAATGATCAGCAGA
           GCTCAATAGTCCTCAATGGTGGTGATTGTGCCAAACTTCCTGGTGATATTGGCAATGT
           CTGGAGACAGTTTTGGTTGTGCATGATGGGAACTGCTACCAGCATCTACTGGGTAGAGG
           [-,C]
           AGGGATACTGCCAAACATCTTACAATGAATAGCACAGCCCCAATACAAAGCATATTCAG
           CCCACAACATCCACAGTGCTACACTTGAAAACCCTGCCATAAAGGCCTTGCAGCACAAGG
           CCTGAGGCTCAGTCGCAGAACAGAGTGGCTTTGCAGCTGGCTGCAGTGTGGAGTCATGAG
           GTGGGAGGGGTGACTAACGATACAACTAGAGAGTTTAGCACACATCAGCCCTAGGGGCT
           GGAGGAGTTGCACAAGGGGAGTTTGAACCTATTGGCAAGGCTGCTGGGGAACCGATGAAA

20105    CCTGTCATCTAATCTAATATAGACACATGTTAGAAGCTCACAGCATTCATTTAGATCATG
           CGCAGCTGATGAAATATAGTCCTGCAGGTCAAGGAGAAAGCAGCTTGAGCATTTGAATCC
           TGGTTCTGCCACTTACTCCTGGCTGCTGTGTACAGATCTGCAGGCTGACTCCCCTGCATG
           GGAGAGTGGGGGCTCACGTCACATGGGAGGCTGGTTTCCTCCACCCACCAAGACATTTGG
           AGTGCCTTCTAATTGGCACAAATGTACTCATGGGTTGGCCACAGTCCTGCACATGATCTT
           [A,G]
           CGCAAGTCAGACTGCTTCTCTGAGCCTGCTTAATACTGCCTGCCTTTAGCGTTGATGAGA
           AGATTAAGAAACAAAGTAGATAAATGCCTAGCCGAGGGTCAGCCACTTGGTAGGCACTCA
           AGAAATGATTGTACAAGAAGCTCCAGACCTTCAGTCACAATCCCCGCTGTTGCAATTGTT
           TCTGCCTCACCTGACAGGCACTGTAGTTGCTCAGGTGACCTCTGCAGCTGTGCTTTGTTC
           TCTGCGAGGCACAGGGAGCCACCGGGACCCCAAGGCTGCAGCAGTGGCCAGTGGGTGAGC

24195    TATGCCTCTGCCACCCCAGCCAGAGTCATAAAGAACCAGACAGAAGCAGGACCCAAGAACA
           TCAGGCCCAAAGGAGAGCTGTGGGAAGTGAAATACTATATTCAGGGAGACCCTCAGCTCC
           TTCCCATCTCAGTTCCCCAAATGAGAGCAAGCAGGCTGATACTTCTCAGGTGGGGTATGG
           AGATATCCCACCTGATCCCTCTTGTCAGTTGATAAGCTGGACTCCACATAGCTTATAGTC
           AGCTTTTTGGTGCTTCACTCTTAAATATGAATGACTAGACAAAGATCAATTGTCATTTGT
           [A,-]
           AAAAAAAAAAAAAAAAAAAAAAAACTCTTCAAAATGAAAGACAGAACCAAAACAATCAGAG
           GAAAAGAACTTGTAGAAAACAGGAACGATGCAGGGAATAGAAGAGACTATTTTTTAAAAC
           TTGTAATTATTATCTTTTGACATTAAAGAGAAGATAAGGCCTCCATGAAACAAGAACAAA
           TGCTGTAAATCAAGGAACATTCAGAGAACAACAAGGACATTTCGAAATAAAAATATGTA
           AATACATTTGCAGAAAAACATGGACAAATCTTAAAGCATATGTTAAATACAATAAGTCAGA

24220    CATAAAGAACCAGACAGAAGCAGGACCCAAGAACATGAGGCCCAAAGGACAGCTGTGGGA
           AGTGAAATACTATATTCAGGGAGACCCTCAGCTCCTTCCCATCTCAGTTCCCCAAATGAG
           AGCAAGCAGGCTGATACTTCTCAGGTGGGGTATGGAGATATCCCACCTGATCCCTCTTGT
           CAGTTGATAAGCTGGACTCCACATAGCTTATAGTCAGCTTTTGGTGCTTCACTCTTAAA
           TATGAATGACTAGACAAAGATCAATTGTCATTTGTAAAAAAAAAAAAAAAAAAAAAAAAAC
           [-,A,T]
           CTTCAAAATGAAAGACAGAACCAAAACAATCAGAGCAAAAGAACTTGTAGAAAACAGCAA
           CGATGCAGGGAATAGAAGAGACTATTTTTTAAAACTTGTAATTATTATCTTTTGAGATTA
           AAGAGAAGATAAGGCCTCCATGAAACAAGAACAAATGCTGTAAATCAAGGAACATTCAGA
           GAACAACAAGGACATTTGGAAATAAAAAATATGTAAATACATTTGCAGAAAACATGGAC
           AAATCTTAAAGATATGTTAAATACAATAAGTCAGACATGAAAGAATACATACTATACTGT

24278    GAAGTGAAATACTATATTCAGGGAGACCCTCAGCTCCTTCCCATCTCAGTTCCCCAAATG
           AGAGCAAGCAGGCTGATACTTCTCAGGTGGGGTATGGAGATATCCCACCTGATCCCTCTT
           GTCAGTTGATAAGCTGGACTCCACATAGCTTATAGTCAGCTTTTTGGTGCTTCACTCTTA
           AATATGAATGACTAGACAAAGATCAATTGTCATTTGTAAAAAAAAAAAAAAAAAAAAAAA
           ACTCTTCAAAATGAAAGACAGAACCAAAACAATCAGAGGAAAAGAACTTGTAGAAAACAG
           [A,G]
           AACGATGCAGGGAATAGAAGAGACTATTTTTTAAAACTTGTAATTATTATCTTTTGAGAT
           TAAAGAGAAGATAAGGCCTCCATGAAACAAGAACAAATGCTGTAAATCAAGGAACATTCA
           GAGAACAACAAGGACATTTGGAAATAAAAAATATGTAAATACATTTGCAGAAAACATGG
           ACAAATCTTAAAGATATGTTAAATACAATAAGTCAGACATGAAAGAATACATACTATACT
           GTACCATTTATACAACATTCAAGGACAGACAAAACTAATCTATAGTAACAGAAATCAAAA

30132    TCTGTCATATCGCTCTCTGAAAAGTCCGAGTCGGCCAGCCACGGTGGCTCACATCTGTAA
```

FIGURE 3S

```
       TCTCAGCACTTTGGGAGGCCGAGGCGGGAGCATCACTTGAGGTCAGGCGTTCGAGACCAG
       CCTGGCCAACATGGTGAAACCCCATCTCCACGAAAAATAAAAAAATTAGCCAGGCCTGGT
       GGCAGGCGCCTGTAATGCCAGCTACCTGGGAGGCTGAGGCAGGAGAACGGCTTGAACCTA
       GGAGGTAGAGGTTGCACTGAGCTGAGATCAGGACCCTGCATTCCAGCCTGGGTGACACAA
       [T,C]
       GATACTCCATCTCAAAAATATATATATATATATACACACACACATATATATTTGAGTAAA
       TACATGTATTAAAATCAATGCAGCCATAAAAAGACAATTATTGCATGATTCCACTTATAT
       GAGGTACCTAGAGCAGTCAAATTCATAGAGAGAGAAAGTAAAATGCTGGCTGCCTGGCGT
       TGAGGGCAGGAAGAATGGCAAGTTGTTTAATGAGTGTAAATTATCGCTTTTGCAAGATGA
       GTAGTTCTGGAGATTGGTTGCACAACAGTGAGAATGTACTTAACACTACTGAACTTACAC

33800  AGAAAAGAATGCTACACACTTTGTATTGTTAGAACATGTCCCATTTTGTTTTGTTAACTC
       TGTCTCAGGCTGATCATCTCCTTTCTTCACAGAGAAAAGTCTGATGATCCCAGGAAACAT
       CATTTCTTTAAAACGATCAACTTTCCTCGCCTGGAAGCTGGCCTAATTGAACCCCCATTT
       GTGCCAGACCCTTCAGTGGTTTATGCCAAAGACATCGCTGAAATTGATGATTTCTCTGAG
       GTTCGGGGGGTGGAATTTGATGACAAAGATAAGCAGTTCTTCAAAAACTTTGCGACAGGT
       [C,A,G]
       CTGTTCCTATAGCATGGCAGCAACAAATTATAGAAACGGGACTGTTTGAGGAACTGAATG
       ACCCCAACAGACCTACGGGTTGTGAGGAGGGTAATTCATCCAAGTCTGCCGTGTGTTTGT
       TATTGTAAATTGCTCTCTTTACCAGACAGGCAGCAGCAGTCTCGGCTGACATAATCCTCG
       AATGTTCCACACGTGGAAATCTGTGGAATGAGGGCTAATCAGTTAGGACGGACATCACAA
       CCACAAAACAATTCAAAAGACAGGCAAGCTCACTACTAGAACACATTTTATTTTCTTTTT

33800  AGAAAAGAATGCTACACACTTTGTATTGTTAGAACATGTCCCATTTTGTTTTGTTAACTC
       TGTCTCAGGCTGATCATCTCCTTTCTTCACAGAGAAAAGTCTGATGATCCCAGGAAACAT
       CATTTCTTTAAAACGATCAACTTTCCTCGCCTGGAAGCTGGCCTAATTGAACCCCCATTT
       GTGCCAGACCCTTCAGTGGTTTATGCCAAAGACATCGCTGAAATTGATGATTTCTCTGAG
       GTTCGGGGGGTGGAATTTGATGACAAAGATAAGCAGTTCTTCAAAAACTTTGCGACAGGT
       [A,G]
       CTCTTCCTATAGCATGGCAGGAAGAAATTATAGAAACGGGACTGTTTGAGGAACTGAATG
       ACCCCAACACACCTACGCGTTGTGAGGAGGGTAATTCATCCAAGTCTGCCGTGTGTTTGT
       TATTGTAAATTGCTCTCTTTACCAGACAGGCAGCAGGAGTCTCGGCTGACATAATCCTCG
       AATGTTCCACACGTGGAAATCTGTGGAATGAGGGCTAATCAGTTAGGAGGGACATCACAA
       CCACAAAACAATTCAAAAGACAGGCAAGCTCACTACTAGAACACATTTTATTTTCTTTTT

34513  TGTATTACGCAAAGTCCTAGGAACAGAGAATGGAACTTTCTCGTGTGCCCAGAAAATGAG
       CATTTGCAATTCTTAGTAAATAATCATTTTAGTTTTTCTTTGTTTATATCTTTTTTTCCC
       TTCATCTTTCTTCGCTTCTATACTTATAAAAAGGATTTTGAAGCTGGAAACAAATGTTTC
       TGACATTCTCCCCCTAAAAAGGAGTGGATTACAATATTTGGCAATCTTTTAAATCACAG
       AATAATTTTCAATTTCAGTGACAGTTTTCTTTTGCAATTTTGTGGAAATAATTTACTATCA
       [A,T]
       AATGTTGAAGCATTTTAAACATAAACATCCATGACATCTGTGAATTAAAGCATTCTGTAA
       ATTTAGTTGAGTCCTTTAAGTAATATGGTACAAATTGCTTCAACTTGCACTACCATATGC
       CATCGGTTCCCAAACTCTGCTGAACTTTGGAATCATCTAGGGATCTTTTAAAAAACTAAT
       GCCTGATTCCCATCCATAGACATTCTGATCCCCACTCCCAGGTATGAGAACAGCTTGACC
       ATTTAGAATTTCAGAAGCTCCCCAGGTGATTCTAATGTGCAGCAGAGTTTGGCAGGCACT

34821  AAGCATTTTAAACATAAACATCCATGACATCTGTGAATTAAAGCATTCTGTAAATTTAGT
       TGAGTCCTTTAAGTAATATGGTACAAATTGCTTCAACTTGCACTACCATATGCCATCGGT
       TCCCAAACTCTGCTGAACTTTGGAATCATCTAGGGATCTTTAAAAAACTAATGCCTGAT
       TCCCATCCATAGACATTCTGATCCCCACTCCCAGGTATGAGAACAGCTTGACCATTTAGA
       ATTTCAGAAGCTCCCCAGGTGATTCTAATGTGCAGCAGAGTTTGGCAGGCACTGCTGTGC
       [A,G]
       CATTTGAATGTTATTACATTCAATCTTATTTTGGTTGCTCAAAACTTCAATCATACATTT
       TGATGGCAACTTTTCAAATGTCCCCAAAGCATGTCATTTAGTAATTGCAGTATAAATGA
       AACAAGACAGTCTATTCATCTTATGCCTTCTCTTGTCCTTGCACACTTAGTTTCTCACA
       CGTATCTTGGGAGCTCGGTCTCTTGGCTATTTCAAGTCCTGAAGGAGACCTATGGGCTTA
       GAAATTGAGTTGAACAGGCCAGGTGCGGTGGCTCATGCCTGCAATTCCAGCACTTTGGGA
```

FIGURE 3T

```
34983    CTGATTCCCATCCATAGACATTCTGATCCCACTCCTAGTTATGAGAACAGCTTGACCAT
         TTAGAATTTCACAACCTCCCAGGTGATTCTAATGTCCAGCACATTTTGGCAGGCACTGC
         TGTGCACATTTGAATGTTATTACATTCAATCTTATTTTGGTTGCTCAAAACTTCAATCAT
         ACATTTCGATCGCAACTTTTCAAATGTCCCCAAAGCATGTTATTTAGTAATTGCAGTAT
         AAATGAAACAAGACAGTCTATTCATCTTATGGCTTTTCTTCTTCGTG
         [C,A]
         ACACTTTAGTTTCTCACACCTATCTTGGGAGCTCCGTCTCTTGGCTATTTCAAGTCCTGA
         AGGAGACCTATGGGCTTAGAAATTGAGTTGAACAGGCCAGCTGCGGTGGCTCATGCCTGC
         AATTCCAGCACTTTGGGAGGCCAAGGCAGATGGATCATGAGGTCAGGGGCTCAAGACTAG
         CCTGGCCAACATGTTGTAAACCCCGTCTCTACTAAAAATACAAAAATTAGCCCGGTGTGG
         TGGTGCACATCTATAATCCCACTTACCCGGGAGCCTCAGGCAGGAGAATTGCTTGAACCC

35153    TGGTTGCTCAAAACTTCAATCATACATTTTGATGGCAACTTTTCAAATGTCCCCAAAGCA
         TGTCATTTTAGTAATTGCAGTATAAATGAAACAAGACAGTCTATTCATCTTATGGCTTCT
         CTTGTCCTTGCACACTTTAGTTTCTCACACGTATCTTGCGAGCTCGGTCTCTTGGCTATT
         TCAAGTCCTGAAGGAGACCTATGGGCTTAGAAATTGAGTTGAACAGGCCAGGTGCGGTGG
         CTCATGCCTGCAATTCCAGCACTTTGGGAGGCCAAGGCAGATGGATCATGAGGTCAGGGG
         [C,T]
         TCAAGACTAGCCTGGCCAACATGTTGTAAACCCCGTCTCTACTAAAAATACAAAAATTAG
         CCCGGTGTGGTGGTGCACATCTATAATCCCAGTTACCCGGGAGCCTCAGGCAGGAGAATT
         GCTTGAACCCAGGAGGCGGAGGTTGTAGTGAGCCAAGATCGCAACATTGCACTCCAGGCT
         GGGCAGCAAGAGCAAGACTCTATCTCAAAAAAAAACAAAACAAAACAAAACAAAAAAAAC
         AGAAAAGAAATTGAATTGAAAAAATACTAACCATCATTTCAAGTGGCTGCCCAGCCAACA

35153    CAGTCTATTCATCTTATGGCTTCTCTTGTCCTTGCACACTTTAGTTTCTCACACGTATCT
         TGGGAGCTCGGTCTCTTGGCTATTTCAAGTCCTGAAGGAGACCTATGGGCTTAGAAATTG
         AGTTGAACAGGCCAGGTGCGGTGGCTCATGCCTGCAATTCCAGCACTTTGGGAGGCCAAG
         GCAGATGGATCATGAGGTCAGGGG
         [T,C]
         TCAAGACTAGCCTGGCCAACATGTTGTAAACCCCGTCTCTACTAAAAATACAAAAATTAG
         CCCGGTGTGGTGGTGCACATCTATAATCCCAGTTACCCGGGAGCCTGAGGCAGGAGAATT
         GCTTGAACCCAGGAGGCGGAGGTTGTAGTGAGCCAAGATCGCAACATTGCACTCCAGGCT
         GGGCAGCAAGAGCAAGACTCTATC

36368    ATAAAAAAATAAAAATGTCTTGTTGCATTGGTTCCTTAGTCTGAATTGCCTCTGCTTTCA
         ATAAACTTTAAATGCAAATCTGTTTTATATCTTAGAACTAACTTAGGAAAATAACTGAAT
         AAGTAGTTGTATTAATCCATTCTCACACTGCTATAAAGAAATACCTGAGG
         [C,T]
         TGGGCATGGTGGCTCACGCCTGCAATCCCAGCACTTTGGGAGTCCAAGGCAGGCAGATCA
         CCTGAGATTAGGAGTTTGAGACCAGCCTGGCCAACATGGTAAAATCCTGTCTCCACTAAA
         AATATACAAATTAGCCAGGTGTGGTGGTGTGTGCCTATAATCCCAGCTAC
```

FIGURE 3U

US 6,579,709 B2

ISOLATED HUMAN KINASE PROTEINS, NUCLEIC ACID MOLECULES ENCODING HUMAN KINASE PROTEINS, AND USES THEREOF

RELATED APPLICATIONS

This present application is a divisional of U.S. Ser. No. 09/738,894, filed Dec. 18, 2000, now U.S. Pat. No. 6,331,423 issued Dec. 13, 2001, which claims priority to case No. 60/208,331 filed Jun. 1, 2000, now abandoned.

FIELD OF THE INVENTION

The present invention is in the field of kinase proteins that are related to the G-protein coupled receptor kinase subfamily, recombinant DNA molecules, and protein production. The present invention specifically provides novel peptides and proteins that effect protein phosphorylation and nucleic acid molecules encoding such peptide and protein molecules, all of which are useful in the development of human therapeutics and diagnostic compositions and methods.

BACKGROUND OF THE INVENTION

Protein Kinases

Kinases regulate many different cell proliferation, differentiation, and signaling processes by adding phosphate groups to proteins. Uncontrolled signaling has been implicated in a variety of disease conditions including inflammation, cancer, arteriosclerosis, and psoriasis. Reversible protein phosphorylation is the main strategy for controlling activities of eukaryotic cells. It is estimated that more than 1000 of the 10,000 proteins active in a typical mammalian cell are phosphorylated. The high energy phosphate, which drives activation, is generally transferred from adenosine triphosphate molecules (ATP) to a particular protein by protein kinases and removed from that protein by protein phosphatases. Phosphorylation occurs in response to extracellular signals (hormones, neurotransmitters, growth and differentiation factors, etc), cell cycle checkpoints, and environmental or nutritional stresses and is roughly analogous to turning on a molecular switch. When the switch goes on, the appropriate protein kinase activates a metabolic enzyme, regulatory protein, receptor, cytoskeletal protein, ion channel or pump, or transcription factor.

The kinases comprise the largest known protein group, a superfamily of enzymes with widely varied functions and specificities. They are usually named after their substrate, their regulatory molecules, or some aspect of a mutant phenotype. With regard to substrates, the protein kinases may be roughly divided into two groups; those that phosphorylate tyrosine residues (protein tyrosine kinases, PTK) and those that phosphorylate serine or threonine residues (serine/threonine kinases, STK). A few protein kinases have dual specificity and phosphorylate threonine and tyrosine residues. Almost all kinases contain a similar 250–300 amino acid catalytic domain. The N-terminal domain, which contains subdomains I–IV, generally folds into a two-lobed structure, which binds and orients the ATP (or GTP) donor molecule. The larger C terminal lobe, which contains subdomains VI A–XI, binds the protein substrate and carries out the transfer of the gamma phosphate from ATP to the hydroxyl group of a serine, threonine, or tyrosine residue. Subdomain V spans the two lobes.

The kinases may be categorized into families by the different amino acid sequences (generally between 5 and 100 residues) located on either side of, or inserted into loops of, the kinase domain. These added amino acid sequences allow the regulation of each kinase as it recognizes and interacts with its target protein. The primary structure of the kinase domains is conserved and can be further subdivided into 11 subdomains. Each of the 11 subdomains contains specific residues and motifs or patterns of amino acids that are characteristic of that subdomain and are highly conserved (Hardie, G. and Hanks, S. (1995) The Protein Kinase Facts Books, Vol I:7–20 Academic Press, San Diego, Calif.).

The second messenger dependent protein kinases primarily mediate the effects of second messengers such as cyclic AMP (cAMP), cyclic GMP, inositol triphosphate, phosphatidylinositol, 3,4,5-triphosphate, cyclic-ADPribose, arachidonic acid, diacylglycerol and calcium-calmodulin. The cyclic-AMP dependent protein kinases (PKA) are important members of the STK family. Cyclic-AMP is an intracellular mediator of hormone action in all prokaryotic and animal cells that have been studied. Such hormone-induced cellular responses include thyroid hormone secretion, cortisol secretion, progesterone secretion, glycogen breakdown, bone resorption, and regulation of heart rate and force of heart muscle contraction. PKA is found in all animal cells and is thought to account for the effects of cyclic-AMP in most of these cells. Altered PKA expression is implicated in a variety of disorders and diseases including cancer, thyroid disorders, diabetes, atherosclerosis, and cardiovascular disease (Isselbacher, K. J. et al. (1994) Harrison's Principles of Internal Medicine, McGraw-Hill, New York, N.Y., pp. 416–431, 1887).

Calcium-calmodulin (CaM) dependent protein kinases are also members of STK family. Calmodulin is a calcium receptor that mediates many calcium regulated processes by binding to target proteins in response to the binding of calcium. The principle target protein in these processes is CaM dependent protein kinases. CaM-kinases are involved in regulation of smooth muscle contraction (MLC kinase), glycogen breakdown (phosphorylase kinase), and neurotransmission (CaM kinase I and CaM kinase II). CaM kinase I phosphorylates a variety of substrates including the neurotransmitter related proteins synapsin I and II, the gene transcription regulator, CREB, and the cystic fibrosis conductance regulator protein, CFTR (Haribabu, B. et al. (1995) EMBO Journal 14:3679–86). CaM II kinase also phosphorylates synapsin at different sites, and controls the synthesis of catecholamines in the brain through phosphorylation and activation of tyrosine hydroxylase. Many of the CaM kinases are activated by phosphorylation in addition to binding to CaM. The kinase may autophosphorylate itself, or be phosphorylated by another kinase as part of a "kinase cascade".

Another ligand-activated protein kinase is 5'-AMP-activated protein kinase (AMPK) (Gao, G. et al. (1996) J. Biol Chem. 15:8675–81). Mammalian AMPK is a regulator of fatty acid and sterol synthesis through phosphorylation of the enzymes acetyl-CoA carboxylase and hydroxymethylglutaryl-CoA reductase and mediates responses of these pathways to cellular stresses such as heat shock and depletion of glucose and ATP. AMPK is a heterotrimeric complex comprised of a catalytic alpha subunit and two non-catalytic beta and gamma subunits that are believed to regulate the activity of the alpha subunit. Subunits of AMPK have a much wider distribution in non-lipogenic tissues such as brain, heart, spleen, and lung than expected. This distribution suggests that its role may extend beyond regulation of lipid metabolism alone.

The mitogen-activated protein kinases (MAP) are also members of the STK family. MAP kinases also regulate intracellular signaling pathways. They mediate signal transduction from the cell surface to the nucleus via phosphorylation cascades. Several subgroups have been identified, and each manifests different substrate specificities and responds to distinct extracellular stimuli (Egan, S. E. and Weinberg, R. A. (1993) *Nature* 365:781–783). MAP kinase signaling pathways are present in mammalian cells as well as in yeast. The extracellular stimuli that activate mammalian pathways include epidermal growth factor (EGF), ultraviolet light, hyperosmolar medium, heat shock, endotoxic lipopolysaccharide (LPS), and pro-inflammatory cytokines such as tumor necrosis factor (TNF) and interleukin-1 (IL-1).

PRK (proliferation-related kinase) is a serum/cytokine inducible STK that is involved in regulation of the cell cycle and cell proliferation in human megakaroytic cells (Li, B. et al. (1996) *J. Biol. Chem.* 271:19402–8). PRK is related to the polo (derived from humans polo gene) family of STKs implicated in cell division. PRK is downregulated in lung tumor tissue and may be a proto-oncogene whose deregulated expression in normal tissue leads to oncogenic transformation. Altered MAP kinase expression is implicated in a variety of disease conditions including cancer, inflammation, immune disorders, and disorders affecting growth and development.

The cyclin-dependent protein kinases (CDKs) are another group of STKs that control the progression of cells through the cell cycle. Cyclins are small regulatory proteins that act by binding to and activating CDKs that then trigger various phases of the cell cycle by phosphorylating and activating selected proteins involved in the mitotic process. CDKs are unique in that they require multiple inputs to become activated. In addition to the binding of cyclin, CDK activation requires the phosphorylation of a specific threonine residue and the dephosphorylation of a specific tyrosine residue.

Protein tyrosine kinases, PTKs, specifically phosphorylate tyrosine residues on their target proteins and may be divided into transmembrane, receptor PTKs and nontransmembrane, non-receptor PTKs. Transmembrane protein-tyrosine kinases are receptors for most growth factors. Binding of growth factor to the receptor activates the transfer of a phosphate group from ATP to selected tyrosine side chains of the receptor and other specific proteins. Growth factors (GF) associated with receptor PTKs include; epidermal GF, platelet-derived GF, fibroblast GF, hepatocyte GF, insulin and insulin-like GFs, nerve GF, vascular endothelial GF, and macrophage colony stimulating factor.

Non-receptor PTKs lack transmembrane regions and, instead, form complexes with the intracellular regions of cell surface receptors. Such receptors that function through non-receptor PTKs include those for cytokines, hormones (growth hormone and prolactin) and antigen-specific receptors on T and B lymphocytes.

Many of these PTKs were first identified as the products of mutant oncogenes in cancer cells where their activation was no longer subject to normal cellular controls. In fact, about one third of the known oncogenes encode PTKs, and it is well known that cellular transformation (oncogenesis) is often accompanied by increased tyrosine phosphorylation activity (Carbonneau H and Tonks N K (1992) *Annu. Rev. Cell Biol.* 8:463–93). Regulation of PTK activity may therefore be an important strategy in controlling some types of cancer.

G Protein-Coupled Receptor Kinases

G protein-coupled receptor kinases (GRKs), also referred to as rhodopsin kinases, phosphorylate light-activated rhodopsin and promote the binding of arrestin to terminate visual signaling by transducin in the rod cell of the mammalian retina. Experimental results indicate that GRKs perform analogous functions in cone visual signalling. One such GRK, GRK7, contains a consensus sequence for geranylgeranylation of the C terminus. Functional studies demonstrate that this kinase phosphorylates bovine rhodopsin in a light-dependent manner and can be autophosphorylated, similar to GRK1. (Hisatomi O, et al., *FEBS Lett* 1998 March 13;424(3):159–64 (1998); Lyubarsky A L, et al., *J Neurosci* March 15;20(6):2209–17 (2000); Weiss, Ellen R., et al., *Molecular Vision* 4:27 (1998)).

Kinase proteins, particularly members of the G-protein coupled receptor kinase subfamily, are a major target for drug action and development. Accordingly, it is valuable to the field of pharmaceutical development to identify and characterize previously unknown members of this subfamily of kinase proteins. The present invention advances the state of the art by providing previously unidentified human kinase proteins that have homology to members of the G-protein coupled receptor kinase subfamily.

SUMMARY OF THE INVENTION

The present invention is based in part on the identification of amino acid sequences of human kinase peptides and proteins that are related to the G-protein coupled receptor kinase subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate kinase activity in cells and tissues that express the kinase. Experimental data as provided in FIG. 1 indicates expression in humans in skin, germinal center B cells, colon, kidney, and lung (including fetal).

DESCRIPTION OF THE FIGURE SHEETS

FIGS. 1A–1B provide the nucleotide sequence of a cDNA molecule that encodes the kinase protein of the present invention. (SEQ ID NO:1) In addition, structure and functional information is provided, such as ATG start, stop and tissue distribution, where available, that allows one to readily determine specific uses of inventions based on this molecular sequence. Experimental data as provided in FIG. 1 indicates expression in humans in skin, germinal center B cells, colon, kidney, and lung (including fetal).

FIGS. 2A–2D provide the predicted amino acid sequence of the kinase of the present invention. (SEQ ID NO:2) In addition structure and functional information such as protein family, function, and modification sites is provided where available, allowing one to readily determine specific uses of inventions based on this molecular sequence.

FIGS. 3A–3U provides genomic sequences that span the gene encoding the kinase protein of the present invention. (SEQ ID NO:3) In addition structure and functional information, such as intron/exon structure, promoter location, etc., is provided where available, allowing one to readily determine specific uses of inventions based on this molecular sequence. As illustrated in FIG. 3, SNPs were identified at 37 different nucleotide positions.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a kinase protein or part of a kinase protein and are related to the G-protein coupled receptor kinase subfamily. Utilizing these sequences, additional genomic sequences were assembled and transcript and/or cDNA sequences were isolated and characterized. Based on this analysis, the present invention provides amino acid sequences of human kinase peptides and proteins that are related to the G-protein coupled receptor kinase subfamily, nucleic acid sequences in the form of transcript sequences, cDNA sequences and/or genomic sequences that encode these kinase peptides and proteins, nucleic acid variation (allelic information), tissue distribution of expression, and information about the closest art known protein/peptide/domain that has structural or sequence homology to the kinase of the present invention.

In addition to being previously unknown, the peptides that are provided in the present invention are selected based on their ability to be used for the development of commercially important products and services. Specifically, the present peptides are selected based on homology and/or structural relatedness to known kinase proteins of the G-protein coupled receptor kinase subfamily and the expression pattern observed. Experimental data as provided in FIG. 1 indicates expression in humans in skin, germinal center B cells, colon, kidney, and lung (including fetal). The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known G-protein coupled receptor kinase family or subfamily of kinase proteins.

Specific Embodiments

Peptide Molecules

The present invention provides nucleic acid sequences that encode protein molecules that have been identified as being members of the kinase family of proteins and are related to the G-protein coupled receptor kinase subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the kinase peptides of the present invention, kinase peptides, or peptides/proteins of the present invention.

The present invention provides isolated peptide and protein molecules that consist of, consist essentially of, or comprise the amino acid sequences of the kinase peptides disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the kinase peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated kinase peptide can be purified from cells that naturally express it, purified from cells that have been altered to express it (recombinant), or synthesized using known protein synthesis methods. Experimental data as provided in FIG. 1 indicates expression in humans in skin, germinal center B cells, colon, kidney, and lung (including fetal). For example, a nucleic acid molecule encoding the kinase peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the kinase peptides of the present invention are the naturally occurring mature proteins. A brief description of how various types of these proteins can be made/isolated is provided below.

The kinase peptides of the present invention can be attached to heterologous sequences to form chimeric or fusion proteins. Such chimeric and fusion proteins comprise a kinase peptide operatively linked to a heterologous protein having an amino acid sequence not substantially homologous to the kinase peptide. "Operatively linked" indicates that the kinase peptide and the heterologous protein are fused in-frame. The heterologous protein can be fused to the N-terminus or C-terminus of the kinase peptide.

In some uses, the fusion protein does not affect the activity of the kinase peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant kinase peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology*, 1992). Moreover, many expression vectors are commercially available that already encode a fusion moiety (e.g., a GST protein). A kinase peptide-encoding nucleic acid can be cloned into such an expression vector such that the fusion moiety is linked inframe to the kinase peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the kinase peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part 1*, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)) (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the kinase peptides of the present invention as well as being encoded by the same genetic locus as the kinase peptide provided herein. The gene encoding the novel kinase protein of the present invention is located on a genome component that has been mapped to human chromosome 3 (as indicated in FIG. 3), which is supported by multiple lines of evidence, such as STS and BAC map data.

Allelic variants of a kinase peptide can readily be identified as being a human protein having a high degree (significant) of sequence homology/identity to at least a portion of the kinase peptide as well as being encoded by the same genetic locus as the kinase peptide provided herein. Genetic locus can readily be determined based on the genomic information provided in FIG. 3, such as the genomic sequence mapped to the reference human. The gene encoding the novel kinase protein of the present invention is located on a genome component that has been mapped to human chromosome 3 (as indicated in FIG. 3), which is supported by multiple lines of evidence, such as STS and BAC map data. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a kinase peptide encoding nucleic acid molecule under stringent conditions as more fully described below.

FIG. 3 provides information on SNPs that have been found in and around the gene encoding the kinase proteins of the present invention. SNPs were identified at 37 different nucleotide positions, including non-synonymous coding SNPs at position 33800. The changes in the amino acid sequence that these SNPs cause can readily be determined using the universal genetic code and the protein sequence provided in FIG. 2 as a reference. SNPs outside the ORF and in introns may affect control/regulatory elements.

Paralogs of a kinase peptide can readily be identified as having some degree of significant sequence homology/identity to at least a portion of the kinase peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a kinase peptide encoding nucleic acid molecule under moderate to stringent conditions as more fully described below.

Orthologs of a kinase peptide can readily be identified as having some degree of significant sequence homology/identity to at least a portion of the kinase peptide as well as being encoded by a gene from another organism. Preferred orthologs will be isolated from mammals, preferably primates, for the development of human therapeutic targets and agents. Such orthologs will be encoded by a nucleic acid sequence that will hybridize to a kinase peptide encoding nucleic acid molecule under moderate to stringent conditions, as more fully described below, depending on the degree of relatedness of the two organisms yielding the proteins.

Non-naturally occurring variants of the kinase peptides of the present invention can readily be generated using recombinant techniques. Such variants include, but are not limited to deletions, additions and substitutions in the amino acid sequence of the kinase peptide. For example, one class of substitutions are conserved amino acid substitution. Such substitutions are those that substitute a given amino acid in a kinase peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306–1310 (1990).

Variant kinase peptides can be fully functional or can lack function in one or more activities, e.g. ability to bind substrate, ability to phosphorylate substrate, ability to mediate signaling, etc. Fully functional variants typically contain only conservative variation or variation in non-critical residues or in non-critical regions. FIG. 2 provides the result of protein analysis and can be used to identify critical domains/regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)), particularly using the results provided in FIG. 2. The latter procedure introduces single alanine mutations at every residue in the molecule. The resulting mutant molecules are then tested for biological activity such as kinase activity or in assays such as an in vitro proliferative activity. Sites that are critical for binding partner/substrate binding can also be determined by structural analysis such as crystallization, nuclear magnetic resonance or photoaffinity labeling (Smith et al., *J. Mol. Biol.* 224:899–904 (1992); de Vos et al. *Science* 255:306–312 (1992)).

The present invention further provides fragments of the kinase peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a kinase peptide. Such fragments can be chosen based on the ability to retain one or more of the biological activities of the kinase peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the kinase peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in kinase peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties,* 2nd Ed., T. E. Creighton, W. H. Freeman and Company, New York (1993). Many detailed reviews are available on this subject, such as by Wold, F., *Posttranslational Covalent Modification of Proteins,* B. C. Johnson, Ed., Academic Press, New York 1–12 (1983); Seifter et al. (*Meth. Enzymol* 182: 626–646 (1990)) and Rattan et al. (*Ann. N.Y. Acad. Sci.* 663:48–62 (1992)).

Accordingly, the kinase peptides of the present invention also encompass derivatives or analogs in which a substituted amino acid residue is not one encoded by the genetic code, in which a substituent group is included, in which the mature kinase peptide is fused with another compound, such as a compound to increase the half-life of the kinase peptide (for example, polyethylene glycol), or in which the additional amino acids are fused to the mature kinase peptide, such as a leader or secretory sequence or a sequence for purification of the mature kinase peptide or a pro-protein sequence.

Protein/Peptide Uses

The proteins of the present invention can be used in substantial and specific assays related to the functional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a kinase-effector protein interaction or kinase-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, kinases isolated from humans and their human/mammalian orthologs serve as targets for identifying agents for use in mammalian therapeutic applications, e.g. a human drug, particularly in modulating a biological or pathological response in a cell or tissue that expresses the kinase. Experimental data as provided in FIG. 1 indicates that kinase proteins of the present invention are expressed in humans in skin, germinal center B cells, colon, kidney, and lung (including fetal). Specifically, a virtual northern blot shows expression in skin, germinal center B cells, colon, kidney, and lung. In addition, PCR-based tissue screening panels indicate expression in fetal lung tissue. A large percentage of pharmaceutical agents are being developed that modulate the activity of kinase proteins, particularly members of the G-protein coupled receptor kinase subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in humans in skin, germinal center B cells, colon, kidney, and lung (including fetal). Such uses can readily be determined using the information provided herein, that which is known in the art, and routine experimentation.

The proteins of the present invention (including variants and fragments that may have been disclosed prior to the present invention) are useful for biological assays related to kinases that are related to members of the G-protein coupled receptor kinase subfamily. Such assays involve any of the known kinase functions or activities or properties useful for diagnosis and treatment of kinase-related conditions that are specific for the subfamily of kinases that the one of the present invention belongs to, particularly in cells and tissues that express the kinase. Experimental data as provided in FIG. 1 indicates that kinase proteins of the present invention are expressed in humans in skin, germinal center B cells, colon, kidney, and lung (including fetal). Specifically, a virtual northern blot shows expression in skin, germinal center B cells, colon, kidney, and lung. In addition, PCR-based tissue screening panels indicate expression in fetal lung tissue.

The proteins of the present invention are also useful in drug screening assays, in cell-based or cell-free systems. Cell-based systems can be native, i.e., cells that normally express the kinase, as a biopsy or expanded in cell culture. Experimental data as provided in FIG. 1 indicates expression in humans in skin, germinal center B cells, colon, kidney, and lung (including fetal). In an alternate embodiment, cell-based assays involve recombinant host cells expressing the kinase protein.

The polypeptides can be used to identify compounds that modulate kinase activity of the protein in its natural state or an altered form that causes a specific disease or pathology associated with the kinase. Both the kinases of the present invention and appropriate variants and fragments can be used in high-throughput screens to assay candidate compounds for the ability to bind to the kinase. These compounds can be further screened against a functional kinase to determine the effect of the compound on the kinase activity. Further, these compounds can be tested in animal or invertebrate systems to determine activity/effectiveness. Compounds can be identified that activate (agonist) or inactivate (antagonist) the kinase to a desired degree.

Further, the proteins of the present invention can be used to screen a compound for the ability to stimulate or inhibit interaction between the kinase protein and a molecule that normally interacts with the kinase protein, e.g. a substrate or a component of the signal pathway that the kinase protein normally interacts (for example, another kinase). Such assays typically include the steps of combining the kinase protein with a candidate compound under conditions that allow the kinase protein, or fragment, to interact with the target molecule, and to detect the formation of a complex between the protein and the target or to detect the biochemical consequence of the interaction with the kinase protein and the target, such as any of the associated effects of signal transduction such as protein phosphorylation, cAMP turnover, and adenylate cyclase activation, etc.

Candidate compounds include, for example, 1) peptides such as soluble peptides, including Ig-tailed fusion peptides and members of random peptide libraries (see, e.g., Lam et al., *Nature* 354:82–84 (1991); Houghten et al., *Nature* 354:84–86 (1991)) and combinatorial chemistry-derived molecular libraries made of D- and/or L- configuration amino acids; 2) phosphopeptides (e.g., members of random and partially degenerate, directed phosphopeptide libraries, see, e.g., Songyang et al., *Cell* 72:767–778 (1993)); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for substrate binding. Other candidate compounds include mutant kinases or appropriate fragments containing mutations that affect kinase function and thus compete for substrate. Accordingly, a fragment that competes for substrate, for example with a higher affinity, or a fragment that binds substrate but does not allow release, is encompassed by the invention.

The invention further includes other end point assays to identify compounds that modulate (stimulate or inhibit) kinase activity. The assays typically involve an assay of events in the signal transduction pathway that indicate kinase activity. Thus, the phosphorylation of a substrate, activation of a protein, a change in the expression of genes that are up- or down-regulated in response to the kinase protein dependent signal cascade can be assayed.

Any of the biological or biochemical functions mediated by the kinase can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the kinase can be assayed. Experimental data as provided in FIG. 1 indicates that kinase proteins of the present invention are expressed in humans in skin, germinal center B cells, colon, kidney, and lung (including fetal). Specifically, a virtual northern blot shows expression in skin, germinal center B cells, colon, kidney, and lung. In addition, PCR-based tissue screening panels indicate expression in fetal lung tissue.

Binding and/or activating compounds can also be screened by using chimeric kinase proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a substrate-binding region can be used that interacts with a different substrate then that which is recognized by the native kinase. Accordingly, a different set of signal transduction components is available as an end-point assay for activation. This allows for assays to be performed in other than the specific host cell from which the kinase is derived.

The proteins of the present invention are also useful in competition binding assays in methods designed to discover compounds that interact with the kinase (e.g. binding partners and/or ligands). Thus, a compound is exposed to a kinase polypeptide under conditions that allow the compound to bind or to otherwise interact with the polypeptide. Soluble kinase polypeptide is also added to the mixture. If the test compound interacts with the soluble kinase polypeptide, it decreases the amount of complex formed or activity from the kinase target. This type of assay is particularly useful in cases in which compounds are sought that interact with specific regions of the kinase. Thus, the soluble polypeptide that competes with the target kinase region is designed to contain peptide sequences corresponding to the region of interest.

To perform cell free drug screening assays, it is sometimes desirable to immobilize either the kinase protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of kinase-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a kinase-binding protein and a candidate compound are incubated in the kinase protein-presenting wells and the amount of complex trapped in the well can be quantitated. Methods for detecting such complexes, in addition to those described above for the GST-immobilized complexes, include immunodetection of complexes using antibodies reactive with the kinase protein target molecule, or which are reactive with kinase protein and compete with the target molecule, as well as enzyme-linked assays which rely on detecting an enzymatic activity associated with the target molecule.

Agents that modulate one of the kinases of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of kinase protein activity identified according to these drug screening assays can be used to treat a subject with a disorder mediated by the kinase pathway, by treating cells or tissues that express the kinase. Experimental data as provided in FIG. 1 indicates expression in humans in skin, germinal center B cells, colon, kidney, and lung (including fetal). These methods of treatment include the steps of administering a modulator of kinase activity in a pharmaceutical composition to a subject in need of such treatment, the modulator being identified as described herein.

In yet another aspect of the invention, the kinase proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with the kinase and are involved in kinase activity. Such kinase-binding proteins are also likely to be involved in the propagation of signals by the kinase proteins or kinase targets as, for example, downstream elements of a kinase-mediated signaling pathway. Alternatively, such kinase-binding proteins are likely to be kinase inhibitors.

The two-hybrid system is based on the modular nature of most transcription factors, which consist of separable DNA-binding and activation domains. Briefly, the assay utilizes two different DNA constructs. In one construct, the gene that codes for a kinase protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a kinase-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the kinase protein.

This invention further pertains to novel agents identified by the above-described screening assays. Accordingly, it is within the scope of this invention to further use an agent identified as described herein in an appropriate animal model. For example, an agent identified as described herein (e.g., a kinase-modulating agent, an antisense kinase nucleic acid molecule, a kinase-specific antibody, or a kinase-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The kinase proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. Experimental data as provided in FIG. 1 indicates expression in humans in skin, germinal center B cells, colon, kidney, and lung (including fetal). The method involves contacting a biological sample with a compound capable of interacting with the kinase protein such that the interaction can be detected. Such an assay can be provided in a single detection format or a multidetection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered kinase activity in cell-based or cell-free assay, alteration in substrate or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (*Clin. Exp. Pharmacol. Physiol.* 23(10–11):983–985 (1996)), and Linder, M. W. (*Clin. Chem.* 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the kinase protein in which one or more of the kinase functions in one population is different from those in another population. The peptides thus allow a target to ascertain a genetic predisposition that can affect treatment modality. Thus, in a ligand-based treatment, polymorphism may give rise to amino terminal extracellular domains and/or other substrate-binding regions that are more or less active in substrate binding, and kinase activation. Accordingly, substrate dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in humans in skin, germinal center B cells, colon, kidney, and lung (including fetal). Accordingly, methods for treatment include the use of the kinase protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or F(ab')$_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the kinase proteins. Antibodies can be prepared from any region of the peptide as described herein. However, preferred regions will include those involved in function/activity and/or kinase/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidinibiotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that kinase proteins of the present invention are expressed in humans in skin, germinal center B cells, colon, kidney, and lung (including fetal). Specifically, a virtual northern blot shows expression in skin, germinal center B cells, colon, kidney, and lung. In addition, PCR-based tissue screening panels indicate expression in fetal lung tissue. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in humans in skin, germinal center B cells, colon, kidney, and lung (including fetal). If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in humans in skin, germinal center B cells, colon, kidney, and lung (including fetal). The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in humans in skin, germinal center B cells, colon, kidney, and lung (including fetal). Thus, where a specific protein has been correlated with expression in a specific tissue, antibodies that are specific for this protein can be used to identify a tissue type.

The antibodies are also useful for inhibiting protein function, for example, blocking the binding of the kinase peptide to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nucleic acid arrays and similar methods have been developed for antibody arrays.

Nucleic Acid Molecules

The present invention further provides isolated nucleic acid molecules that encode a kinase peptide or protein of the present invention (cDNA, transcript and genomic sequence). Such nucleic acid molecules will consist of, consist essentially of, or comprise a nucleotide sequence that encodes one of the kinase peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5KB, 4KB, 3KB, 2KB, or 1KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the kinase peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (anti-sense strand).

The invention further provides nucleic acid molecules that encode fragments of the peptides of the present invention as well as nucleic acid molecules that encode obvious variants of the kinase proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene. The gene encoding the novel kinase protein of the present invention is located on a genome component that has been mapped to human chromosome 3 (as indicated in FIG. 3), which is supported by multiple lines of evidence, such as STS and BAC map data.

FIG. 3 provides information on SNPs that have been found in and around the gene encoding the kinase proteins of the present invention. SNPs were identified at 37 different nucleotide positions, including non-synonymous coding SNPs at position 33800. The changes in the amino acid sequence that these SNPs cause can readily be determined using the universal genetic code and the protein sequence provided in FIG. 2 as a reference. SNPs outside the ORF and in introns may affect control/regulatory elements.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in Current Protocols in Molecular Biology, John Wiley & Sons, N.Y. (1989), 6.3.1–6.3.6. One example of stringent hybridization conditions are hybridization in 6×sodium chloride/sodium citrate (SSC) at about 45C., followed by one or more washes in 0.2×SSC, 0.1% SDS at 50–65C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. As illustrated in FIG. 3, SNPs were identified at 37 different nucleotide positions.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. The gene encoding the novel kinase protein of the present invention is located on a genome component that has been mapped to human chromosome 3 (as indicated in FIG. 3), which is supported by multiple lines of evidence, such as STS and BAC map data.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data as provided in FIG. 1 indicates that kinase proteins of the present invention are expressed in humans in skin, germinal center B cells, colon, kidney, and lung (including fetal). Specifically, a virtual northern blot shows expression in skin, germinal center B cells, colon, kidney, and lung. In addition, PCR-based tissue screening panels indicate expression in fetal lung tissue. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in kinase protein expression relative to normal results.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express a kinase protein, such as by measuring a level of a kinase-encoding nucleic acid in a sample of cells from a subject e.g., mRNA or genomic DNA, or determining if a kinase gene has been mutated. Experimental data as provided in FIG. 1 indicates that kinase proteins of the present invention are expressed in humans in skin, germinal center B cells, colon, kidney, and lung (including fetal). Specifically, a virtual northern blot shows expression in skin, germinal center B cells, colon, kidney, and lung. In addition, PCR-based tissue screening panels indicate expression in fetal lung tissue.

Nucleic acid expression assays are useful for drug screening to identify compounds that modulate kinase nucleic acid expression.

The invention thus provides a method for identifying a compound that can be used to treat a disorder associated with nucleic acid expression of the kinase gene, particularly biological and pathological processes that are mediated by the kinase in cells and tissues that express it. Experimental data as provided in FIG. 1 indicates expression in humans in skin, germinal center B cells, colon, kidney, and lung (including fetal). The method typically includes assaying the ability of the compound to modulate the expression of the kinase nucleic acid and thus identifying a compound that can be used to treat a disorder characterized by undesired kinase nucleic acid expression. The assays can be performed in cell-based and cell-free systems. Cell-based assays include cells naturally expressing the kinase nucleic acid or recombinant cells genetically engineered to express specific nucleic acid sequences.

The assay for kinase nucleic acid expression can involve direct assay of nucleic acid levels, such as mRNA levels, or on collateral compounds involved in the signal pathway. Further, the expression of genes that are up- or downregulated in response to the kinase protein signal pathway can also be assayed. In this embodiment the regulatory regions of these genes can be operably linked to a reporter gene such as luciferase.

Thus, modulators of kinase gene expression can be identified in a method wherein a cell is contacted with a candidate compound and the expression of mRNA determined. The level of expression of kinase mRNA in the presence of the candidate compound is compared to the level of expression of kinase mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate kinase nucleic acid expression in cells and tissues that express the kinase. Experimental data as provided in FIG. 1 indicates that kinase proteins of the present invention are expressed in humans in skin, germinal center B cells, colon, kidney, and lung (including fetal). Specifically, a virtual northern blot shows expression in skin, germinal center B cells, colon, kidney, and lung. In addition, PCR-based tissue screening panels indicate expression in fetal lung tissue. Modulation includes both up-regulation (i.e. activation or agonization) or down-regulation (suppression or antagonization) or nucleic acid expression.

Alternatively, a modulator for kinase nucleic acid expression can be a small molecule or drug identified using the screening assays described herein as long as the drug or small molecule inhibits the kinase nucleic acid expression in the cells and tissues that express the protein. Experimental data as provided in FIG. 1 indicates expression in humans in skin, germinal center B cells, colon, kidney, and lung (including fetal).

The nucleic acid molecules are also useful for monitoring the effectiveness of modulating compounds on the expression or activity of the kinase gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in kinase nucleic acid expression, and particularly in qualitative changes that lead to pathology. The nucleic acid molecules can be used to detect mutations in kinase genes and gene expression products such as mRNA. The nucleic acid molecules can be used as hybridization probes to detect naturally occurring genetic mutations in the kinase gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the kinase gene associated with a dysfunction provides a diagnostic tool for an active disease or susceptibility to disease when the disease results from overexpression, underexpression, or altered expression of a kinase protein.

Individuals carrying mutations in the kinase gene can be detected at the nucleic acid level by a variety of techniques. FIG. 3 provides information on SNPs that have been found in and around the gene encoding the kinase proteins of the present invention. SNPs were identified at 37 different nucleotide positions, including non-synonymous coding SNPs at position 33800. The changes in the amino acid sequence that these SNPs cause can readily be determined using the universal genetic code and the protein sequence provided in FIG. 2 as a reference. SNPs outside the ORF and in introns may affect control/regulatory elements. The gene encoding the novel kinase protein of the present invention is located on a genome component that has been mapped to human chromosome 3 (as indicated in FIG. 3), which is supported by multiple lines of evidence, such as STS and BAC map data. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080 (1988); and Nakazawa et al., *PNAS* 91:360–364 (1994)), the latter of which can be particularly useful for detecting point mutations in the gene (see Abravaya et al., *Nucleic Acids Res.* 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a kinase gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant kinase gene and a wild-type gene can be determined by direct DNA sequencing. A variety of automated sequencing procedures can be utilized when performing the diagnostic assays (Naeve, C. W., (1995) *Biotechniques* 19:448), including sequencing by mass spectrometry (see, e.g., PCT International Publication No. WO 94/16101; Cohen et al., *Adv. Chromatogr.* 36:127–162 (1996); and Griffin et al., *Appl. Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al., *PNAS* 85:4397 (1988); Saleeba et al., *Meth. Enzymol.* 217:286–295 (1992)), electrophoretic mobility of mutant and wild type nucleic acid is compared (Orita et al., *PNAS* 86:2766 (1989); Cotton et al., *Mutat. Res.* 285:125–144 (1993); and Hayashi et al., *Genet. Anal. Tech. Appl.* 9:73–79 (1992)), and movement of mutant or wild-type fragments in polyacrylamide gels containing a gradient of denaturant is assayed using denaturing gradient gel electrophoresis (Myers et al., *Nature* 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship) Accordingly, the nucleic acid molecules described herein can be used to assess the mutation content of the kinase gene in an individual in order to select an appropriate compound or dosage regimen for treatment. FIG. 3 provides information on SNPs that have been found in and around the gene encoding the kinase proteins of the present invention. SNPs were identified at 37 different nucleotide positions, including non-synonymous coding SNPs at position 33800. The changes in the amino acid sequence that these SNPs cause can readily be determined using the universal genetic code and the protein sequence provided in FIG. 2 as a reference. SNPs outside the ORF and in introns may affect control/regulatory elements.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control kinase gene expression in cells, tissues, and organisms. A DNA antisense nucleic acid molecule is designed to be complementary to a region of the gene involved in transcription, preventing transcription and hence production of kinase protein. An antisense RNA or DNA nucleic acid molecule would hybridize to the mRNA and thus block translation of mRNA into kinase protein.

Alternatively, a class of antisense molecules can be used to inactivate mRNA in order to decrease expression of kinase nucleic acid. Accordingly, these molecules can treat a disorder characterized by abnormal or undesired kinase nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the kinase protein, such as substrate binding.

The nucleic acid molecules also provide vectors for gene therapy in patients containing cells that are aberrant in kinase gene expression. Thus, recombinant cells, which include the patient's cells that have been engineered ex vivo and returned to the patient, are introduced into an individual where the cells produce the desired kinase protein to treat the individual.

The invention also encompasses kits for detecting the presence of a kinase nucleic acid in a biological sample. Experimental data as provided in FIG. 1 indicates that kinase proteins of the present invention are expressed in humans in skin, germinal center B cells, colon, kidney, and lung (including fetal). Specifically, a virtual northern blot shows expression in skin, germinal center B cells, colon, kidney, and lung. In addition, PCR-based tissue screening panels indicate expression in fetal lung tissue. For example, the kit can comprise reagents such as a labeled or labelable nucleic acid or agent capable of detecting kinase nucleic acid in a biological sample; means for determining the amount of kinase nucleic acid in the sample; and means for comparing the amount of kinase nucleic acid in the sample with a standard. The compound or agent can be packaged in a suitable container. The kit can further comprise instructions for using the kit to detect kinase protein mRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS:1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al, PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides which cover the full length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the kinase proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the kinase gene of the present invention. FIG. 3 provides information on SNPs that have been found in and around the gene encoding the kinase proteins of the present invention. SNPs were identified at 37 different nucleotide positions, including non-synonymous coding SNPs at position 33800. The changes in the amino acid sequence that these SNPs cause can readily be determined using the universal genetic code and the protein sequence provided in FIG. 2 as a reference. SNPs outside the ORF and in introns may affect control/regulatory elements.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques,* Elsevier Science Publishers, Amsterdam, The Netherlands (1986); Bullock, G. R. et al., *Techniques in Immunocytochemistry,* Academic Press, Orlando, Fla. Vol. 1 (1982), Vol. 2 (1983), Vol. 3 (1985); Tijssen, P., *Practice and Theory of Enzyme Immunoassays: Laboratory Techniques in Biochemistry and Molecular Biology,* Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified kinase gene of the present invention can be routinely identified using the sequence information disclosed herein can be readily incorporated into one of the established kit formats which are well known in the art, particularly expression arrays.

Vectors/host cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extra-chromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual.* 2nd. ed., Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual.* 2nd. ed., Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli*, *Streptomyces*, and *Salmonella typhimurium*. Eukaryotic cells include, but are not limited to, yeast, insect cells such as Drosophila, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enterokinase. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11d (Studier et al., *Gene Expression Technology: Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990) 119–128). Alternatively, the sequence of the nucleic acid molecule of interest can be altered to provide preferential codon usage for a specific host cell, for example *E. coli*. (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J.* 6:229–234 (1987)), pMFa (Kurjan et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf 9 cells) include the pAc series (Smith et al., *Mol. Cell Biol.* 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al., *EMBO J.* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual. 2nd, ed., Cold Spring Harbor Laboratory,* Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual. 2nd, ed., Cold Spring Harbor Laboratory,* Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing finctions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell- free transcription and translation systems can also be used to produce these proteins using RNA derived from the DNA constructs described herein.

Where secretion of the peptide is desired, which is difficult to achieve with multi-transmembrane domain containing proteins such as kinases, appropriate secretion signals are incorporated into the vector. The signal sequence can be endogenous to the peptides or heterologous to these peptides.

Where the peptide is not secreted into the medium, which is typically the case with kinases, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of vectors and host cells

The recombinant host cells expressing the peptides described herein have a variety of uses. First, the cells are useful for producing a kinase protein or peptide that can be further purified to produce desired amounts of kinase protein or fragments. Thus, host cells containing expression vectors are useful for peptide production.

Host cells are also useful for conducting cell-based assays involving the kinase protein or kinase protein fragments, such as those described above as well as other formats known in the art. Thus, a recombinant host cell expressing a native kinase protein is useful for assaying compounds that stimulate or inhibit kinase protein function.

Host cells are also useful for identifying kinase protein mutants in which these functions are affected. If the mutants naturally occur and give rise to a pathology, host cells containing the mutations are useful to assay compounds that have a desired effect on the mutant kinase protein (for example, stimulating or inhibiting function) which may not be indicated by their effect on the native kinase protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a kinase protein and identifying and evaluating modulators of kinase protein activity. Other examples of transgenic animals include nonhuman primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the kinase protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence(s) can be operably linked to the transgene to direct expression of the kinase protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo,* (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect substrate binding, kinase protein activation, and signal transduction, may not be evident from in vitro cell-free or cell-based assays. Accordingly, it is useful to provide non-human transgenic animals to assay in vivo kinase protein function, including substrate interaction, the effect of specific mutant kinase proteins on kinase protein function and substrate interaction, and the effect of chimeric kinase proteins. It is also possible to assess the effect of null mutations, that is, mutations that substantially or completely eliminate one or more kinase protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

That which is claimed is:

1. An isolated polypeptide having an amino acid sequence consisting of SEQ ID NO:2.

2. An isolated G-protein-coupled receptor kinase having an amino acid sequence comprising SEQ ID NO:2.

3. A composition comprising the polypeptide of claim 1 and a carrier.

4. A composition comprising the G-protein-coupled receptor kinase of claim 2 and a carrier.

* * * * *

SEQUENCE LISTING

<160> NUMBER OF SEQ ID NOS: 4

<210> SEQ ID NO 1
<211> LENGTH: 1662
<212> TYPE: DNA
<213> ORGANISM: Human

<400> SEQUENCE: 1

```
atggtggaca tgggggccct ggacaacctg atcgccaaca ccgcctacct gcaggcccgg      60
aagccctcgg actgcgacag caaagagctg cagcggcggc ggcgtagcct ggccctgccc     120
```

-continued

```
gggctgcagg gctgcgcgga gctccgccag aagctgtccc tgaacttcca cagcctgtgt        180
gagcagcagc ccatcggtcg ccgcctcttc cgtgacttcc tagccacagt gcccacgttc        240
cgcaaggcgg caaccttcct agaggacgtg cagaactggg agctggccga ggagggaccc        300
accaaagaca gcgcgctgca ggggctggtg gccacttgtg cgagtgcccc tgccccgggg        360
aacccgcaac ccttcctcag ccaggccgtg gccaccaagt gccaagcagc caccactgag        420
gaagagcgag tggctgcagt gacgctggcc aaggctgagg ccatggcttt cttgcaagag        480 cagccctta aggatttcgt gaccagcgcc ttctacgaca agtttctgca gtggaaactc         540
ttcgagatgc aaccagtgtc agacaagtac ttcactgagt tcagagtgct ggggaaaggt        600
ggttttgggg aggtatgtgc cgtccaggtg aaaaacactg gaagatgta tgcctgtaag         660 aaactggaca agaagcggct gaagaagaaa ggtggcgaga agatggctct cttggaaaag        720
gaaatcttgg agaaggtcag cagcccttc attgtctctc tggcctatgc ctttgagagc         780
aagacccatc tctgccttgt catgagcctg atgaatgggg agacctcaa gttccacatc         840 tacaacgtgg gcacgcgtgg cctggacatg agccgggtga tctttttactc ggcccagata       900 gcctgtggga tgctgcacct ccatgaactc ggcatcgtct atcgggacat gaagcctgag        960
aatgtgcttc tggatgacct cggcaactgc aggttatctg acctggggct ggccgtggag       1020
atgaagggtg gcaagcccat cacccagagg gctggaacca atggttacat ggctcctgag       1080
atcctaatgg gaaaggtaag gttattccta cctgtggact ggtttgccat gggatgcagc       1140
atttatgaaa tggttgctgg acgaacacca ttcaaagatt acaaggaaaa ggtcagtaaa       1200
gaggatctga gcaaagaac tctgcaagac gaggtcaaat tccagcatga taacttcaca       1260
gaggaagcaa aagatatttg caggctcttc ttggctaaga aaccagagca acgcttagga       1320
agcagagaaa agtctgatga tcccaggaaa catcatttct ttaaaacgat caactttcct       1380
cgcctggaag ctggcctaat tgaaccccca tttgtgccag accttcagt ggtttatgcc        1440 aaagacatcg ctgaaattga tgatttctct gaggttcggg gggtggaatt tgatgacaaa       1500
gataagcagt tcttcaaaaa ctttgcgaca ggtgctgttc ctatagcatg gcaggaagaa       1560
attatagaaa cgggactgtt tgaggaactg aatgacccca acagacctac gggttgtgag       1620
gagggtaatt catccaagtc tggcgtgtgt ttgttattgt aa                          1662
```

<210> SEQ ID NO 2
<211> LENGTH: 553
<212> TYPE: PRT
<213> ORGANISM: Human

<400> SEQUENCE: 2

```
Met Val Asp Met Gly Ala Leu Asp Asn Leu Ile Ala Asn Thr Ala Tyr
 1               5                  10                  15

Leu Gln Ala Arg Lys Pro Ser Asp Cys Asp Ser Lys Glu Leu Gln Arg
             20                  25                  30

Arg Arg Arg Ser Leu Ala Leu Pro Gly Leu Gln Gly Cys Ala Glu Leu
         35                  40                  45

Arg Gln Lys Leu Ser Leu Asn Phe His Ser Leu Cys Glu Gln Gln Pro
     50                  55                  60

Ile Gly Arg Arg Leu Phe Arg Asp Phe Leu Ala Thr Val Pro Thr Phe
 65                  70                  75                  80

Arg Lys Ala Ala Thr Phe Leu Glu Asp Val Gln Asn Trp Glu Leu Ala
                 85                  90                  95

Glu Glu Gly Pro Thr Lys Asp Ser Ala Leu Gln Gly Leu Val Ala Thr
```

-continued

```
                    100                 105                 110
        Cys Ala Ser Ala Pro Ala Pro Gly Asn Pro Gln Pro Phe Leu Ser Gln
                    115                 120                 125
        Ala Val Ala Thr Lys Cys Gln Ala Ala Thr Thr Glu Glu Glu Arg Val
                    130                 135                 140
        Ala Ala Val Thr Leu Ala Lys Ala Glu Ala Met Ala Phe Leu Gln Glu
        145                 150                 155                 160
        Gln Pro Phe Lys Asp Phe Val Thr Ser Ala Phe Tyr Asp Lys Phe Leu
                            165                 170                 175
        Gln Trp Lys Leu Phe Glu Met Gln Pro Val Ser Asp Lys Tyr Phe Thr
                            180                 185                 190
        Glu Phe Arg Val Leu Gly Lys Gly Phe Gly Glu Val Cys Ala Val
                        195                 200                 205
        Gln Val Lys Asn Thr Gly Lys Met Tyr Ala Cys Lys Lys Leu Asp Lys
                        210                 215                 220
        Lys Arg Leu Lys Lys Gly Gly Glu Lys Met Ala Leu Leu Glu Lys
        225                 230                 235                 240
        Glu Ile Leu Glu Lys Val Ser Ser Pro Phe Ile Val Ser Leu Ala Tyr
                            245                 250                 255
        Ala Phe Glu Ser Lys Thr His Leu Cys Leu Val Met Ser Leu Met Asn
                        260                 265                 270
        Gly Gly Asp Leu Lys Phe His Ile Tyr Asn Val Gly Thr Arg Gly Leu
                    275                 280                 285
        Asp Met Ser Arg Val Ile Phe Tyr Ser Ala Gln Ile Ala Cys Gly Met
                290                 295                 300
        Leu His Leu His Glu Leu Gly Ile Val Tyr Arg Asp Met Lys Pro Glu
        305                 310                 315                 320
        Asn Val Leu Leu Asp Asp Leu Gly Asn Cys Arg Leu Ser Asp Leu Gly
                        325                 330                 335
        Leu Ala Val Glu Met Lys Gly Gly Lys Pro Ile Thr Gln Arg Ala Gly
                    340                 345                 350
        Thr Asn Gly Tyr Met Ala Pro Glu Ile Leu Met Gly Lys Val Ser Tyr
                355                 360                 365
        Ser Tyr Pro Val Asp Trp Phe Ala Met Gly Cys Ser Ile Tyr Glu Met
        370                 375                 380
        Val Ala Gly Arg Thr Pro Phe Lys Asp Tyr Lys Glu Lys Val Ser Lys
        385                 390                 395                 400
        Glu Asp Leu Lys Gln Arg Thr Leu Gln Asp Glu Val Lys Phe Gln His
                        405                 410                 415
        Asp Asn Phe Thr Glu Glu Ala Lys Asp Ile Cys Arg Leu Phe Leu Ala
                    420                 425                 430
        Lys Lys Pro Glu Gln Arg Leu Gly Ser Arg Glu Lys Ser Asp Asp Pro
                    435                 440                 445
        Arg Lys His His Phe Phe Lys Thr Ile Asn Phe Pro Arg Leu Glu Ala
                450                 455                 460
        Gly Leu Ile Glu Pro Pro Phe Val Pro Asp Pro Ser Val Val Tyr Ala
        465                 470                 475                 480
        Lys Asp Ile Ala Glu Ile Asp Asp Phe Ser Glu Val Arg Gly Val Glu
                        485                 490                 495
        Phe Asp Asp Lys Asp Lys Gln Phe Phe Lys Asn Phe Ala Thr Gly Ala
                        500                 505                 510
        Val Pro Ile Ala Trp Gln Glu Glu Ile Ile Glu Thr Gly Leu Phe Glu
                    515                 520                 525
```

```
              Glu Leu Asn Asp Pro Asn Arg Pro Thr Gly Cys Glu Glu Gly Asn Ser
                  530                 535                 540

Ser Lys Ser Gly Val Cys Leu Leu Leu
              545                 550

<210> SEQ ID NO 3
<211> LENGTH: 36651
<212> TYPE: DNA
<213> ORGANISM: Human
<220> FEATURE:
<221> NAME/KEY: misc_feature
<222> LOCATION: (1)...(36651)
<223> OTHER INFORMATION: n = A,T,C or G

<400> SEQUENCE: 3
ccaggaggcg gagtttgcag tgagccgaga tcacgccact gcactccagc ctgggtgata       60
gagcgagact ccgtctcaaa ataaaaatta aaaaaaataa aaaatatata taaatatgta      120
tatatctgtg atatcaatgc taccgttttc tcaaggttct accttgctag gctgccacta      180
cattcctaag aaccacggga aaaggcattt gctcctccga agaaattatc agaccaattt      240
ctcactactg aacaatgtgg accggggtaa catataaaga acagaaaagt atccaacatt      300
tcccgtgttg gtttcaaagc agacagcatg gttcagagca gcgggcaccg gtgcagatcg      360
cccatctcca cggcagaggt gatcgtttcc agcgcagcgg tgcaaagcca aagggcaccc      420
acgagttcat tacataattc ctggtagcat gaggccaagt gtgtatgtgc tctaggggaa      480
cagtcggagg ctctgacagg cagagcaagg cgatcatgac tatgttttca caagtgtat       540
gctagcagtt gtttggaaaa agactgacca gcttttttcc ccctccttct ccctctctct      600
ttttttttgct tgtaaacact ttggcataat actgaatgac ttgtttttaa gctgccttag      660
ccttgctttg tgaagaaaaa gcctgagtat cctttccctg tggggcacag gttgttattt      720
ttggagcaga agttcttagc ctgatctctg tctagatcaa tttctgtctt gatgaggccg      780
aggtctgtga cagctccgag cgtcctccgt ggaaggaagc ttcctcgctt ggtggggcgc      840
atgggcaaag atgttgaggg gccacgtctg aaacttcact gctcttggct ccacgcgaag      900
gctccttggc attcagagtc tgctcgttag attgtgccct tggaacagtc gcgaccgcat      960
gccgtgagtg gcgtgctttc tgtctttggg atcatggaaa attcttgtct cattcagagc     1020
ccagacactc caggccaagt cccttcattt caggaatatg gcttttttctg cttatactgc     1080
ttcatggtat gttttgggtg gagatggccc ctcttttttt tttttttttt tttgagacgg     1140
agtctcgctc tgtggcccag acgggagtgc agtggcgcaa tctcggctca ctgcaagctc     1200
cgcctcccgg gttcacgcca ttctcctgcc tcagcctccc gagtagctgg gactacaggc     1260
gcccgccatc aagcccggct aattttttttt tttttttgta tttttttttag tagagacggg     1320
gtttcaccgt gttagccagg atggtctcga tctcctgacc tcgtgatccg cccggagatg     1380
gcccctcttt taacccaagg tactccaggt cacagactcc tcagagctaa gacagctgca     1440
ggatttctgc aagctattca gggtgcatct gccctggcca acactggagt ccttagggcc     1500
tctgggaaca catctcggga ctcaaagctc acaacatccc ctctgtaacc tgctcttcgt     1560
gtcaggctgc tagaacctgg gaggaaactg ctctgacttc tcacagttcc tctgcctgac     1620
ctgctattcc taggagttta catagcttga ggctgatagg aaacaagtaa aattagaaac     1680
agattaaaact actgcatcag caacaaatta gatgacaacg gtatgatcac ttccttggaa     1740
cacagttcta gctagatatt cagggtacag ggctatgtgg agaaagaccc taagatgaag     1800
```

```
ggaccagtgg gggaggtggc cccggcaggt gtcccagcag ctttcgcctt ggcaggtggg   1860
agcatgacct atcgtgtgca gttcctggcg ggctatacat agccagtcaa agcttcttac   1920
aagagaaacc tctttcacac cctccacggg tcccacccac aggccacagg actcactgta   1980
aatcccttgg acgttgtctc acccgggaag ggaaagcagc cagcagccct ccagccctct   2040
tgtgctttcc ctgggagtgc gccccgtgct cagccatggt ggacatgggg gccctggaca   2100
acctgatcgc caacaccgcc tacctgcagg cccggaagcc ctcggactgc gacagcaaag   2160
agctgcagcg gcggcggcgt agcctggccc tgcccgggct gcagggctgc gcggagctcc   2220
gccagaagct gtccctgaac ttccacagcc tgtgtgagca gcagcccatc ggtcgccgcc   2280
tcttccgtga cttcctagcc acagtgccca cgttccgcaa ggcggcaacc ttcctagagg   2340
acgtgcagaa ctgggagctg ccgaggagg  acccaccaa agacagcgcg ctgcaggggc   2400
tggtggccac ttgtgcgagt gcccctgccc cggggaaccc gcaacccttc ctcagccagg   2460
ccgtggccac caagtgccaa gcagccacca ctgaggaaga gcgagtggct gcagtgacgc   2520
tggccaaggc tgaggccatg gctttcttgc aagagcagcc cttttaaggat ttcgtgacca   2580 gcgccttcta cgacaagttt ctgcagtgga aactcttcga gatgcaacca gtgtcagaca   2640
agtacttcac tgagttcaga gtgctgggga aggtggtttt tggggaggta agtgtctccc   2700
agtagccagg ctagaaggtg aagcatagag catgaaaggg ggtaatgttg cctttctttt   2760
tttaaatctc agttacttag aactaatttc agcaccatat gtggaggatt tctagccccg   2820
tctccccagc ccccttcttt gtgtgtgcca tggtgtgaaa taaaacacaa atggcatgag   2880
agagacaagc aaaatttata cttggccaag actctgtcat gggtctccat taggaacgtg   2940
ctgagatgcc tggacacttc agagaatgat agcaatgtgt gacagaagat ctccgtttcc   3000
cctaaattgt gataatgaag gcacttcaag aaaaatggat atttaagaaa atactctaac   3060
tagctgggtg tggtgacatg cctgtaatcc cagctacttg ggaggctgaa gcaggagaat   3120
cacttgagcc tgggaggtgg aggttgcagt gagccaagat cgtgccactg cactccagcc   3180
tgggtgacag agcaagactc aaaaaaaaaa aaaaaagaa agaaagaaaa gaaagaaaac   3240
acttatcttg aagtaaggtt gagaacctgt tttgtaccac tgttgtgccc agctttctgt   3300
ttttaagtaa taaaaaatat ttcaggtaaa atttgcttga tataaaacta accattaact   3360
gttttaaaat gtacaatgca gtggcacttc gcacaaatgc aatgttgggt aagcaacacc   3420
tcaatctgga tccaagacac tctcatcacc cctgtgccca ttaatagtgc ctccccatcc   3480
ctctcctcct ccagccctga caaccactag tccgctttct gtctctaggg atttgcctat   3540
tctgggtgtt tcacacaata tgtgaccttt tgtgtctggc ttctttcact cattagaatg   3600
tttttggggt tcattcacac tgtagcatgt gtcaatactc cattccttttt tatggctgta   3660 taatattcca tcgtatggat gtactacatt tcatgtagcc attcatctgt tgatggacac   3720
ttgggctgtt ttcaccttttt ggctattgtg tatggtgctg ctattcatgc acaagtattt   3780
gtttgaatcc ttgttttcat ttctcttgga tttatgccca ggagtggaat tgctagggca   3840
tatggtgata ctatgtttaa cttttcaagg agccaccaaa cttccacat  tttttattcc   3900 caccagcaat gcttaaaggt ttcgatttct ccacatcctt gccaacactt gatatttttcc   3960 tgtattttttt tatgaaggcc tgcctagtga ggtgaaggag tatcgcactg tagtccccac   4020
tttttcttga gaacacttct tatttacagc tactcctttc tccaatgcct aacatctttc   4080
cacccacctc ctccttttatc atctccacct ctctgcagta ccatctactt ctacctcttt   4140
ctcttctttt ctttctccctt taaggtatgt gccgtccagg tgaaaaacac tgggaagatg   4200
```

-continued

```
tatgcctgta agaaactgga caagaagcgg ctgaagaaga aggtggcga gaagatggct    4260 ctcttggaaa aggaaatctt ggagaaggtc agcagccctt tcattgtctc tctggcctat    4320
gcctttgaga gcaagaccca tctctgcctt gtcatgagcc tgatgaatgg gggagacctc    4380
aagttccaca tctacaacgt gggcacgcgt ggcctggaca tgagccgggt gatcttttac    4440
tcggcccaga tagcctgtgg gatgctgcac ctccatgaac tcggcatcgt ctatcgggac    4500
atgaagcctg agaatgtgct tctggatgac ctcggcaact gcaggttatc tgacctgggg    4560
ctggccgtgg agatgaaggg tggcaagccc atcacccaga gggtgagtga ctctccacct    4620
gccccaagtg cggggcacag agttggaaag gaggggagag ggcttttcta ttcccagggc    4680
aaatagagcc ttggacttaa ttcttttggt ttttttttcct aaagcgctta cgttgtcatc    4740
ttgccttaag atgagtggtg taagaggatt agattcattg ctatttgag ggctactttg    4800 ctctcctctc acaggggatg ggggagcctc ctttgtgagt tggggatggc ctgtgctttt    4860
gtgatgagat ggaaaaagct gaatccatag tcatggtccg ggtgtgtcaa taaccacctc    4920
tatggtgctg tgttcctgag ccaatagagc cttgggttcc ttttctggaa atgaaggggg    4980
ctggacccta aaattccatg atcctaggag gtaaacttta atcagataag aaaaagaatg    5040
atccggctgg gtgtgatggc tcacgcctgt aatcccagca cttggggag gccgaggcgg    5100 gtggatctgc tgaggtcagg agtttgagac cagcctggcc aacatggtga aaccccatct    5160
ctagtaaaaa tacaaaaatt agccaggcat ggtgacaggc gcctgtaatc ccagctactc    5220
gggaggttga ggcaggagaa tcgcttgaac ccaggaggcg gaagttgtag tgagccgaga    5280
tcatgccact gcactccagc ctgctcgaca gagcaagact ctgtctcaaa aaaaaaaag    5340 aaagaaagaa aaagaaaaaa gaaaaaaaat aaagaaagaa ggaaaagaa tgatcctctc    5400 acacctagaa cattaaaagt aaaatatctc ctttcctgtt tagtgtggaa tgggcgaatg    5460
ttttgcattg gatgaagatg atattttaaa tgaaaatata tggaagaaaa caaaggcaac    5520
tgatgtttat tttaatcagt tttgttcaaa gtgacttgct taaaattctt tggttaaaaa    5580
gagaattata attaagcgat tatgttaggt gaacgacgga aaatctctgg aattctaaca    5640
tctttacctc tgagtctctg tgcacaaagg tgggagattc cacagcaagg caagggctca    5700
aacctggctc ttaaatggtt acttaaaacc tcatttttgt acagttttca gcctacaggg    5760
cccaaaggaa atgagaaaaa tcatggcaag tttgggaaac tgctgtggtg atttttatgtg    5820 gctgtaatgg aagggatgtt gacaagactg aagggctggg cttcacagg tgctggaatg    5880 ccttcttgta ggggaagagg ggttcttgaa gggttttaag aagggaaatg acatgattag    5940
atttctgtct taaaaagacc aatgcggcaa caatttggaa gttagatggt aggtggggac    6000
atcagttagg aggctaaggt agtgagtggc ccaggcaaga aataatgggg gtctgtacag    6060
gacagtggga ttgaagaagt gggagcaaat tggagctttt ggaaagagat ctgatgggac    6120
ttcaggacca gctgggtatg ggggtgaggg gaaagtgagg gtctctagct ccagtggcca    6180
gaaggaagag cagatttgta ggcaagctgg caagtttaat tgtgattatg ctgtctatga    6240
ggttcctgta gaagggacag gcagagatgt tcactaggca tttagatcta taggcctggt    6300
gctgtggagg aagacctggg atagacgtgg ggatttggag ttatcatggt ttgggaagca    6360
gagggcactg ctgagtcact gggaaagagt aggggaagaa gaccaggaac agaagctgaa    6420
aaacaccaac atgtggggt atagaagaaa aggagccctg aagagtttta agaagtagga    6480
ggctacttgg gaggctgagg caggagaatg acgtcaaccc aggaggcgga gcttgcagtg    6540
```

-continued

```
agctgagatc acaccactgc actctagcct gggctacaaa gcgagactcc atcttaaaaa      6600
aagaaaaaaa aaaaaagaag taggaggaaa ggcaagagtg atatagtcat aggagctgta      6660
tcagttagag atgggtttca ggggcatatc ctagaaaacc caaataacaa tagattaaac      6720
aagacagagg tttatttttc ttatgtaaca gggtgtggaa ataagcactt gccagcatta      6780
gttcagcagc tgcagaataa tgggatctgc atctttataa ttctagcctt ttccatgtgc      6840
tgcaagatgg ctgctgtagc cccagccatc agggccatgt tccaggtagg agaaaggagg      6900
aagggtcagg agtaaatagg catgcatgca gcagttgagt gtggcccct ttaggagctt       6960
tccctgaagc tccatccaac agctttcact tagatgtcac tggctaagac tgtgatctgg      7020
ccacccccta gctgcagagg aagctgacaa atgacattct tgaaaattct ttggttaaaa      7080
agggaattat aattaagcga ttataattac tgaattatat ctgggctgag gagaagatca     7140
cccggctcat gtccaggcca tgtgtgccca cgttgtagat gtggaacttg aggcaggggt      7200
gaaggagcgg gttctagtta gtaaggatga agaacagctg gatattgagc aggtaactag     7260
cagcctctgc cacaggagcc aaagaagagg atttcaggga ggaaagtgtg gtcaaagtgt     7320
caagtgttgc aaagaggtaa cgttgcctgt gggatttggc aattaggaaa tcagtgtaag     7380
ggaatggtga ggtctcaatt cagactctgg aggttggatt gatctagaag tagggaatga    7440
gactctggaa gggggagact ggtccctaga aggggataca gtggggaaat ggagttttga     7500
gatggggagg gcagagcggg tttagatgct gaggcaaaag ccagcagagt aggtgttgat     7560
cctgtgggaa ggaaagacag tagatgatgg cagagaatgt ggggaggagc tgaagtaaca   7620
ccgtctcctc tgtgggtggg aaggaggagc aggccaggga ggtgacagag tgtttgcctc    7680
cttgggacat tcctatgaac acaggaacgc tgtgaatcgt ggatccatgt ctgcctaggc    7740
tggagaaaac tgaagtgcag cacttcacag tttggcattt gtattgtcca ttgtgctgag   7800
caggagcgtt ccttctgagt cgcccatgga catgtatcac actaattgtt gctatatctc    7860
gaccttgctg gaggcttagg ggacacatag agctttggct cactccagtc tcctttctca    7920
gtctcctcag gctctgttca tgggccatgg ccatttggaa ggacagctcc ttccttggct    7980
cccgggtgca gctctctggc tcatctggaa cgtgcaggaa ggtttctgtg cctccccagt    8040
gctgtccgct accaggaacg tacttagtag agaggctcac tgcctacaga cctttggccc    8100
ttttacctct gcgtccctct ccgtcccgtg agaccacact tcagggttta ggccacttgc    8160
ctcatccaag aagtttatg ccccagtttc cgggcctgcc acggaagccc aggggaccat     8220
caggaagggt gaggggagag agatggagag caagattgaa agccataaaa aacaaagaga    8280
agagaaagga aggcctcctt tcttcactgt ttacccttct acacagctaa gtaaaccccc    8340
ttagtttcct attcattgca gctcccacac atataattgg gctcacaagt agactgtaag    8400
gtcattatat tcacaacatt tcacagaaaa aaagacaga tcatagttac agggcttctg     8460
taaccactaa cgttcagttg tgatgtcaag atactgtgtt agagaattac tgtgaacatt    8520
aattctgtgg tttgaatgag tcctcaaaat ttgatgtgtt ggaaacttaa tctccaatgt    8580
ggcagtgttg gagaggtggg gccttaaga ggtgagtgga ccatgagggc tctgccgctg     8640
tgaatagatg aatggattaa tgggttatca caggagtgga aatggtagct ttataagaag    8700
agaaagacct gagctagcac atcagcacac tcagccccac gcgatgccct gagccatctc    8760
agtactcctc agagagttcc caccagcaat aagactctca tcctctcacc agacatttcc    8820
ctcaaccttc ctttccttat aaaatacttt ccttataaaa tactcagtct tagatactct    8880
gtcataagca acagaaaaca agttaagaca gaagaggtaa caaggaaaaa tcaccctgat    8940
```

```
gatggaggtt gaactctgca ttgagtctga gcagttcttc cagaaaagtt aaggcatcat      9000
ggctttggaa atttggctag cttttttctca ttcagagagt tatttagtct tgtataagtt     9060
gggatttctt tctactaaat ataacagaat accagatttt ggtatagatt tggctgttca      9120
gcaatttcac ggacaagacc tctgttaaaa atctcctggc ttgcgctggg tgtggtggct      9180
caggcctaat cccagcactt tgggcccagg aggacaagac cagtcaatag tgcgaacccc      9240
atctcttaaa aaaattttt ttgttttgtt ttaggctggc cgtggtggct cacacctgta       9300
atcccacact tgggaggcc aaggcaggtg gatcccctga ggtcaggagt tcgagaccag       9360
cctggccaac atgttgaaac cctgtctcta ctaaaaatac aaaaattagc caggcatggt      9420
ggtgggtgcc tgtaatccca gctacttggg aggctgctgt gggagaatca tttgaacccg      9480
ggaggtggag gttttagtga gccaagatca taccactgca ctccagcctg gatgaaagag      9540
aaagagtctg tctcaaaaaa aaaaaaaaat tgttttaaac ttagccaggt gtggtgatgc      9600
atgcctgtgg tcccagctac ttgggaggct gaggtgggag gattgcttga gctcaggagt     9660
tcaaggcttc agtgagctat gatcatgcca ctgcactcca gcctgggtga cagaacaata      9720
ccctgtctca aaaaaaaaa aaaaatctt ttggcctttt cctccttgtc acaagtggct        9780
gttgcaactc caaatattga gtctgcattc caggagaaga aaaagagga gaaagaaca       9840 acatccacag atacctgctt atagcccatt agccaggacc atgtcatatg ttcacttcta     9900
gcagcaaagg aggctgaaaa atagagtatt tcattttcca gcctctgttt tgggggatgt    9960 taaggagag gaggaatgag attaggtgtt gggtgagctg acagcatctg ccacaccagg      10020
cccagggaaa aaaatattga tgaggattag gaaatcaaat tcagattcat tacttttaca    10080
gacattggaa ctaaagaatg attgtgacaa tggtatggta gacaaaattc taagatggcc    10140
ccccatcaat gacccttgct tgcccttgta taatccccctc cccttgagtg tagacaagac   10200
ccgtgagtat gatgagatat cactgccatg gttgtgttat gttacagggc aaaagggact   10260 tcagagttttt aattacagtt actagtagca gggtgctgtg gctcacgcct gtaatcctag   10320 cacttttggga ggctgaggca ggcagatcat gatgtcagga gatcaagacc acgctggcta  10380
acacagtgaa acctggtctc tactaaaaat acaaaaaaat tagctgggca tgatggcacg    10440
tgcctgtagt cccagctact tgggaggctg aggcaggaga atcgcttgaa cccaggaggc    10500
agaggttgca gtaagccaag atcacgccac tgcactccag ccagggtgac agagtaagac    10560
tctcggaaaa aaaaaaaaaa agttactagt tagttgactt tgaattcatc aaaagagaaa   10620
ttatccaggt gggcctgacc tcatcacacc tatccttca atatgggcat agaggctaga     10680
gacagcagaa gtcagaaatg taaagcacag agggcctctg tgcaccctgc tggctttgaa    10740
gatggaggag caaggtgtgt aggtggactc taggcactca gagctgcctc tccctgacag    10800
ccagcaagga aacaggggcc tcctttctac agccagagtg aactgaattc tgccatcacc    10860
acatacactt ggaagaggac cttgggctcc agatcagaat gtagcctgac caacatctcc   10920
attttattag ccttgtgagt ccatgaccaa agagccctgc catgctgtgc cagaacttct   10980
gacctacgga actgcaagct aataaatgaa ctgttttaag ttactaagtt tgtggtaatt   11040
tgttacacat cagtagaaaa ctcatacaaa tagttaataa aggaaggtag ccagagaaat   11100
attgtagggt agcatcaaaa ttagtggaga agggctgggt gctatggctg atgcctataa    11160
tcccagcagt ttgggaggct gaggcgggtg gatcacctga ggtcaggagc ttgagaccag    11220
cctggccaac atggtgaaac ctcatctcta ctaaaaatac aaaaattagc cagatatgat    11280
```

-continued

```
ggcaggcacc tgtaatccca gctactcaag tggctgaggc aggagaattg cttgaacctg    11340
ggaggcagaa ggttgcagtg agccaagatt gcgccactgc actccagcct gggcaacaaa    11400
gtgagactct gcctcaaaaa aaaaaaaaaa aaaaattaat agagaagata tcaaggtgct    11460
ggacactgtt agagggataa tattttcctt tctcacagga atcagaatac ctaccaccag    11520
tcaggtgctg tgactcacgc tgtaatccca acactttgg gaagccaagg tgggagaatc    11580
ccttgaggcc agaagtttga ccagtctagg caacatag caagactttg tctcttaaaa    11640
aaaaaaaaa aaaaattacc tgggcatgat ggtatgcacc tgtaatccca gctactcagg    11700
aggctgaggc aggaggattg cttgagcctg ggagtttgag gctgcaggta gccgtgatca    11760
caccactgca ctccagcctg agtgacagag caagaccttg tctctaaaca aacaaacaaa    11820
caaaaaacga gaacaaaaac aaataatacc tactgcctat tttaatagaa ctggaggctg    11880
taattgaatt tagaactttg gacatgagtc ttccaagtgg gtaactcttc cctgggtatg    11940
agctgtgcct ccctggggggg gcacaggccc tttctcgcca ctgaaggaca ctgggtaaag    12000
tactttggat gttgttctac aggcagtagg gagccattga aggttttga acaagaaagt    12060
gccatgacca gagtgattcc ttaggaagat gattctgaca ctatctaaaa tgaaagagaa    12120
agagactaga gctggggaga aacgggaacc caccaagagc tactgtaata atctgcatat    12180
gaggtaatgc gggcctgagg ctgggtcctg ggctctaaac agagctcagc cccctggcct    12240
cttacctggg ctccatcaag atccagacct ttacatgctt ctcttaaaat ggggctgtcc    12300
tcagtggagg gctaggggac agagaacagc tcctagaaca cggtgacttc tgccccgtgg    12360
ggtcttctgg cagctggtag ctgggtagtg actccgggag gtgcttcaag gatggaaagg    12420
agcaggtctg cccaggtttg agagactgag gcagacacgc aaggagatgc cggggctgaa    12480
gagcattggc ctgggaggct gaaacctgag ctcttgtccc agcttcatca ctcattcacc    12540
atgtctgccc tctcaagtgg gccttaagac gtctctgcaa ttgctaccac ttttgagtct    12600
atgagatagt ctttgaatta tctggaggaa agaagtttgc ggtttgaaac aaagtctcat    12660
tctgtcgccc aggctggagt gcagtggtgt gatctcagct cactgaaacc tctacctctc    12720
acgttcaaag cactactaac gcctggctga ggttcaagcg ccaccatgcc tggctaattt    12780
ttgtattttt agtagagatg ggatttcacc atgttggcca agctagtctt gaactcctgg    12840
cctcatgtga tcaacttgcc tcagcctcct aaagtactgg gattgcaggt gtgagccact    12900
gcacctggcc taggaggaaa gaagttttaa actcaaaaga tgaacagata gagtaggtta    12960
ctgtgattta ctggactatc aatcagagtt attatgggac agaactatgt tacttcagaa    13020
aaatgaaatt aacggtttac ataactagga agccctggcc tgatccaggt gtctgagcag    13080
tgtccctggg agtctctgtc tctgtttccc agcttcgctc ttctctgtgt tgccctcact    13140
ctcaggcagg tactccctgc acgggagcca ccagtcgccc catacacttc ctaccaactg    13200
aaccactccc acagagggaa aacatttttct ttatgaatag ttccttcaca gttcccagag    13260
agggcgctca ctggacaact caggtcacat gtccaaccac aaccaatccc attggccgag    13320
actagatcac tgcctgtccc aggagccaga ggaaggtctg tcccacgtaa atctcatgga    13380
tcgagagcag aagaatgtgt tccccacagg aaaatcacaa tgcaaagat ggggactgga    13440
tgccaaatgg gcaaaaaaaa aaaaaaaaa aaaaaaaaaa aacacaaaac agtggaggcc    13500
cctaataact gctgttacct caatggtttg aaaagtttaa aaccttttctg acccccttaat    13560
cacgggatga tgagacctaa gagttccaag taggtaactc ttttctacat atgagctgag    13620
cctcttggga cccctttacaa aaagattctg agttaggtac tgttctgagc tccattgtac    13680
```

-continued

```
aggtagggaa attgagaccc aaagtcacag tactagtatg agatatgatt ccaggcacat    13740
cagatttaaa agcgctcaca gttttgactc catcttattg agttcatgca catggcaaca    13800
tatagcctta tgttttttg tttgtttgtt tgagacagag tctcactctg tagcccaggc    13860
aggagtgcag tggcacgatc tcagctcact gcaacctccg tctcccaggt tcaagtgatt    13920
ctcccgcctc agcctgccgt gtagctggga ttacaagcgc atgctaccac gcccagctaa    13980 tttttttgtac ttctagtaga cagggtttt caccgagtta accagggtgg tcttgatctc    14040
ctgacatgat ctgcatgcct cggcctccca agtgctggg attacaggcc tgagccaccg    14100
cacccagcca gcattatggt ttttaatgct ataaaaggct tttcacttag taagactcag    14160
acagaataag tgcatgtgat gacattagca tatcttccca gtctggtctg atatggacac    14220
caaccacaag cctagctgaa cttctaagaa aggaagactt cagaaaagga tcagccccac    14280
ctacacaggg aatgacggcc attaatattt cagagccagc ttcttaccca taggtgcagc    14340
acaattaaac atgttccagc cactgtctac atgcactttt ttttttttt tttagatgga    14400 gtcttgctct gttgcccagg ctggagtgca atggcacaat cttggctcac tgcgacctct    14460
gcctccaggg ttcaagcaat tctcatgcct cagcctcctg agtagctgtc attataggca    14520
cccaccacca cactcggcta atttgtgtat tttagtaga gtcggggttt caccatgttg    14580
gccaggctgg tctggaactc ctgacctcag gtgatctgcc cacctcggcc tctcaaagtg    14640
ctgggattac aggcgtaagc caccgcgccc ggtcaacatg cacttttaat aaatgtgata    14700
agcacttctg cctgtgctca gttgacatct acatgcacac agtgaaacta gtttgtatca    14760
ttgtaaaaga ttccaagtaa atataatagg aatattgggg agtgaggatc atgcttgtac    14820
tttttaaatt cagaattcta tttggtgagc agtgaccttc aggtattatg caatatgagt    14880
ctttaaaatt tgctattttg ttaggaatgg gaatgaggtt agaatagtga cccagaagct    14940
tgttacatgt ttagatacct ggtcctgcct tgaagtctct gaccaactcc tcacattcag    15000
agggataatg ggagacagag gtttggtatt atatttattt cgaagcatct attgtaccaa    15060
atacaatgct agagacatac tggaaaggtg attttaaaa gacctctgaa catgttttct    15120
tgggagttaa tgcctccata tgtcacaacc atcatgacca tgcccccag tttttttttt    15180 ctttaagtgc tcacttctga gatctagctt aagaaagaca tacaggagag gcattctggt    15240
cacatgaggc atgaagtcat ggtcacactt tggcctgacc aaaaggatta ccaccagcat    15300
tgaccaaatt taattcctac taacttttga cccctacaga aatttgaaat ctattcttaa    15360
attatttacc actaccaagg gcattcaaaa atattcatta cagtctgtaa ttacttttaa    15420
cattccttca tccaaaaggc atgcctttat tcactcactc actcacttgt ttattcaact    15480
tacatgtatc aagtgtttcc cacatgccag gactgttcta aatatgaggg atagccaggt    15540
gccgtggctc atgcctgtaa tcccagcact ttgggaggcc aaggtgggca gatcacttga    15600
ggtcaggagt ttcagaccag cctggccaac atggtgaaaa cctgtatcta ctaaaaatac    15660
aaaaattagc tgggtgtggt ggcgggcccc tataatccca gctacttggg aagctgaggt    15720
aggagaatcg cttgaacccg gaaggcggag gttgtagtga gccgaaatca tgccattgca    15780
ctccagcctg ggacagag cgagactcca tctaaaaaaa aaaaaaaaaa aaaaaattg    15840 agggatagaa ggaagagcag aaaatggaca tgattcctgc cttcatgaag cttacagtct    15900
agtggggaag atagaactta ataaacattc agactgggcg tggtggctca tgcctgtaat    15960
cccagcactt tgggaggccg aggcggacag atcacttgag gtcaggagtt cgagaccagc    16020
```

-continued

```
ctggccaacc tggtgaaacc ctgtctctac taaaaataca aaaaattagc cgggcattgt     16080
agcacatgcc tgtagtccca gctactcggg aggctgaggc aggggaattg cttgaaccca     16140
agagacggag gctgcagtga gtggagatca tgccactgca ctccaacctg gcaacagag      16200 caagattttg tctcaaaaaa aaaaaaaaaa gggaacttaa taatcattca ataagtatt      16260 aaatatcact tatgataaat gctgggaaga catggtacat tgggctctcc aaggaggatt     16320
tgacttaata tgtgaaaatc aaaagtaaa ccacatggga aattcaactt acatgatact      16380
agaaggaaag gaattcactc agcaaagagg ttccggtggt gtctcagatt gggctccctg     16440
gaaacagact gagacagatt tacacatgga agatattggg gagctatgat attgtgaaat     16500
atgtgtttgg tcttcatccc attttctggc atacaactcc aaatcttcaa agtgaaaagc     16560 atcttttgt atattaatga gttgactgat ggctggcagc ccctaggaag ctgcaggatg      16620
gagactggtc accagaaaag ccaaggtagg attagagggt taggactttc agcctatccc     16680
ccaatggcca atgattttat caatcatgcc tgtgtaatga agactccata aaacccaaa      16740 agggcagggt tcagagagct tcctgatagc caatcacgtg gaggcttcca ggaagatgaa     16800
caagaacaca tccacgtgct gggagtgtgg ctcaccccag ctccatgggg acagaagctt     16860
ctgaacttgg gacccttcca gacttggtcc tgtatgactc ttcatttggc tgcttatttg     16920
tgtcatttaa aatatccctt ataacaaacc agaaaacata agtgtttccc tgcattctgt     16980
gagctgctgt ggcaaattaa ttgaacccaa agagaggttt gtggggacct caatttacag     17040
ctggtgggtc agaagttttg aaggcctgga cttgccactg gcattcaaag cctagaggca     17100
gccttgggga ctgagccctc accctgtagg acctggcact gtctccagga gatagtgtca     17160
taatggattt gaattagagg acatccagct cgcatctgct gcagaatgga ttgctggctg     17220
gtttgtgttt tgagagtatt gtgggagaaa ctgagtttgt ttcttctact caggagtgct     17280
ctcctgagat gcagccatga ggaaggcagg actgggcaga gagaacctca cccctagtgc     17340
ggcaggcggt ggggactaag acctcagcca tccttcaggg agctctggag ttgggatgac     17400
tcttctgagt tgcccaaat tgaggtgggg tccagacttg tgtatcccta aggatgcagt      17460
cagtgactgt gagtagctgc cagaagggg cggaagcctg ggatgccatc cccgctgcag      17520
aaggcagttc ccagggaggg gtgcagctgt gagccatcag caagcagtgg ccccagccag     17580
gcatggctgc ataaatttgg gggctcactg tgaaataaaa atatagggcc tcttcttcaa     17640
atatcgggaa aaagcctcct ttcatgctct atttttcaac cagccatagg gtttggattt     17700
gctatttaat gtcatacttc cccaggctct gggatactca aagagtgagt agagaccctc     17760
acagacaccc agggctccaa cccacgactg gacctgagga agcatgtgcc tgaccccagc     17820
cctccctgca cctgagtcca ggcccctacc aggcagaaag tggcaatagt cactgggtga     17880
gggtgggggt agaagtggga ggtggggaag cagacagcca tgaacccatc ccggggaggc     17940
aagcaggtgg caggaggggg actgtgtgag ctgaggctcc aagtacggct ctattggctt     18000
attggacttc acttaaaaga cacaaattca agataaatg attacaaaca gcattaaacc      18060
ccagtaaagg tatgcctctg agcacagggc cctgtccatg ggcactggaa actggcctgg     18120
caccagcagc tggagggtgg gggccaagaa cctgaagagg ggattggagc caagtagccc     18180
ccacaggtgg ggaagagcat ttcaggccat gggaatagtc tgggcaagta tctcttgctt     18240
taggggaaat gaaaaggaag ccaggaaatg aaaagcacat cgtaagagga aatgtggttc     18300
aaatgaagat ggagaggtgg cagggccag acggaacctg cattatggg ccatgttaag       18360 gactttgggt gatcgtctct gatcactgga aaagctgtgg cagggtttca tgaagggga     18420
```

```
aacatgtttc aaattttgtt ttgaaaagat taccccaggt gaagtgaaac agattggagg   18480
agattcaggt agtttgtggt ctttgtaatc caggtaagag gtgatgggc tcagaccaca    18540 gagggagtag tggagacaga acgcagtgga tgaattgggg cgatataata tttcagagtg   18600
aataggcctc agtgatggtt tggatacggg gttaagggag atgggtgtc aagaatgatt    18660 tgttagataa ggctgtgtca caagcacaga cttagaccct gagtactaaa cagggaacca   18720
ggcaaacaaa gaccctgaat actaaacagg gaaccaggca aacaaatgcc tgccttcatg   18780
aagttccagg agaggaaagg gatggacaag gacatgggca gtgataatac ggtgtgatca   18840
gggttgtctg agctgggtac ataggaaggg cacccagccc aacatgagga cctggagtca   18900
cagggtcagg aagggcttcc aaggggaagg gacaaccaag ctaagactta aaagacatga   18960
agccagacag gtaaagagga aggagcatgc gctaggtaaa gggatcagca gagctcaata   19020
gtcctcaatg gcgggtgatt gtgccaaact tcctggggat acttggcaat gtctggagac   19080
agttttggtt gtcatgactg gggaactgct accagcatct agtgggtaga ggcagggata   19140
ctgccaaaca tcttacaatg aatagcacag cccccaacac aaagcatatt cagcccacaa   19200
catccacagt gccacacttg aaaaccctgg cataaaggcc tcgcagcaca aggcctgagg   19260
ctcagtcgca gaacagagtg gctttgcagc tggctgcagt gtggagtcat gaggtgggag   19320
gggtgactaa cgatacaact agagagttta gcagacacca ggccctaggg gctggaggag   19380
ttgcacaagg ggagtttgaa cctattggca agggtgctgg ggaaccgatg aaaggttttt   19440
agcagggaag tgacaaaatc aatcttgggg ccaggtgtgg tggctaatgc ctgtaatctc   19500
agcattttgg gaggccaagg cacaaggatt acttgagcct agcagatgga gaccagcctg   19560
ggcaacaaag cgagactctg ctctatgtta aaaaaaaaa atagccttgg aattacatca    19620
aagagaagga gttagaatga gcacagaaag gctgggaggg aagcagagga ctcagggaac   19680
tgtgggcttg cacattgtct aatggagtca cgggaataag gagaggctgg gccagggggt   19740
ctgcaggatg cggcaggagg gggctgtcat gtgacatgat acagttcagg gacctaatgg   19800
ttgccgtgtc atctaatcta atatagacac atgttagaag ctcagagcat tcatttagat   19860
catgcgcagc tgatgaaata tagtcctgca ggtcaaggag aaaggagctt gagcatttga   19920
atcctggttc tgccacttac tcctggctgc tgtgtacaga tgtgcaggct gactcccctg   19980
catgggagag tggggctga cgtcacatgg gaggctggtt tgctccacgc accaagacat    20040
ttggagtgcc ttctaattgg cacaaatgta ctcatggggt ggccacagcc ctgcacatga   20100
tcttacgcaa gtcagactgc ttctctgagc ctgcttaata ctgcctgcct ttagcgttga   20160
tgagaagatt aagaaacaaa gtagataaat gcctagccga gggtcagcca cttggtaggc   20220
actcaagaaa tgattgtaca agaagctcca gaccttcagt cacaatcccc gctgttgcaa   20280
ttgtttctgc ctcacctgac aggcactgta gttgctcagg tgacctctgc agctgtgctt   20340
tgttctctgc gaggcacagg gagccagcgg gaccccaagg ctgcagcagt gggcagtggg   20400
tgagcagctt gcatctgggt tgagccaagc agacactcac agttgtcttg cttcctcaca   20460
gctgtgtggg gtttcatttg tggttttctt ctgagcatct tagaggcacc gtggaaagta   20520
tgcctcagcc tgctgccaga gagattcata gcacatgaaa ccactgaaga acacgctcaa   20580
gtgaaagaac gggaactatt gatctctgac catgtgccag gccctgcctt tcagtctgat   20640
ggagtcttgt gtagctgtcc tgcctgagac aaccagaacc caggcatggt aacaacagcc   20700
gctaatacat actgtggtag caggcctgct gtgcgccagg ttttgggtcg acacccaatc   20760
```

-continued

```
tgttttatcg ttttaatctt cgtcacagtc ccataaggca agaactgttg aggctcagag    20820
gggttgagta agcggctgtg ggtgaccggc ttataactgg tagagctggg atctgaacta    20880
cagcaaacca acgccagtgt gggagccatt tcacccccaga ctctatgcct gcaaaaagtg   20940
ttattgtgac gaccccctctt ttgggctccc tgtgtgggct ctgtgaaatg ggtgtccttc   21000
cagggtgtc agggagagca ggaagccgcc tctgatggga tgcgccctcc ccgcccagga    21060
agtggcggca gaaagcgagc cctgagaagc caggggcagg agcggcctcc gcgcgacact    21120
gcggcgctcc tgattctgcg gcctgggccc gagcatgcgg ggcgggcgga gcctcgagct    21180
aagtcccctg gggtcccagg gccgcattcc tccgaggtct gcaaaggcca ctgcttaaag    21240
gcgcagagga gcagctggga acgagaacaa agcggccagg ccccctcgg aggaaggaag    21300
gagagagccc caggaaacag ctgatagcgc taagctcagc ttgtttttt cctctgctca    21360
acagttctcc tgccacggca acaaaaacat gtacattctg attccctctt ctgtttggat    21420
tgtgctgtcg actggatctg gtttgtgatg agctgggga agaggcatcc gcgggcgatt    21480
tctggctcgg cgtgccagtg tgcttttgct gggccgcgcc gggantcgcg gagcttcctc    21540
tccggctcct ttctccccgt ctgcgtcgct aatccagcct ggcccggcca ccccaaggga    21600
agacacggcc gtttcttttg atagtggaat tggaggttgc caagttttca gatttaatgg    21660
gaggtggagg gttgctcgtg tccttgacct tgaaggacct gcgcacactc atactttttc    21720
atggacttgt aaaactgtta agaggtgaac tgtgccctct cagctccacc agaagcccct    21780
ccatgttctc tgcactgcga aggtcacagt ctggttcctg gttgtccaga gccacactgg    21840
gactctgtcc aggccagcct gggccctgcc agttcggttc agagtgacag ctacagggtc    21900
aatggaagag gccagcaccc aacagcaaga acaatgtagg gggtatctgg acgggcttgg    21960
gatcttaatc acaccttaag gtgtctacct tcccccaatgt ctggacacct gttggtgaca    22020
ggtggccctg atgggactaa gcttgagatt actgtactag aaggacttcc cgctgcccct    22080
gaggggatgg gggaggggca ctggcactgc caggcgtgct aaaccccgtg aggtctgttg    22140
ttcgatgtcg cccaatgctg ggtatacttg gttttttgcct gaccaggtgt tgactgtgtg    22200
ggtctggaaa gggcaccata aaacccaaag taaaataagg taaaacccag aaaaggataa    22260
aacacataca cacacacaca cccacacacc cctccactaa gagtgctga tactcgggca    22320
atccctacag ccctgggcat ggcggttctg gtcacatgca ctgaaggaga cggttctgat    22380
gctgctgaga cagaggcgca gggccctgtg taactgcagg agttaaaccc agctgtaaga    22440
ggtcagcgtg gttggacctg ctccacgctg cttggcgcgt tctctcctcc caccctactc    22500
tgaggaggca gttcacatgc agaagacaaa tggcataaag gcaggcaat taatttttc     22560
agctggaggc tgcaatggaa tgtgggtgct taaagtctgg cgtgcgcctc taattccatt    22620
ctcctcagtt aaatacctcc gctcttcaag gaggtggtgc ccttcaaagc taccatggct    22680
gacattttct gtctttagga ccaagaggtg aatttagtcc tgaaaattat ttggaatgaa    22740
tctaaggcct tcctgcacgc tgtctcatgc tcttttccact acaccagggg gtctacagtg   22800
ctgtaaagat ggcaggccaa ttcttttactt atttccttgg ggaggtggtt gcagagcatg   22860
gcccagggtc tggtccccatc tcccagaacc ctctgctgtg tggagcagcc gagccagcct   22920
gaaacaggca aaaaatggag aattcactgg gataagggga agggaaacat ctttagcaag   22980
aatgctaaag atcaaggact tagtactggg caaatgggga gagggaagaa ggggactcta   23040
caaggagaa aagaaatcct gaaggaact tggagggta agaaaaagtc acttcaccta     23100
cttctataga ggcggaataa tgtagtagtg aaaagcgcag gccagggcag gcatggtggg   23160
```

-continued

```
tcacgcctgt aatcccagcc ctttgggagg ctgtggcgga tggatcacag gaggtcggga    23220
gttcgagacc agcctagcta acatggtgaa accctgtctc tactaaaaat acaaaattag    23280
ccgggcgtgg tggtgagcgc ctgtaatccc agctactcag gaggctgagg caggagaatc    23340
acttgaacct gggaggtgga ggttgcagtg agccaagatc atgccactgc actccagtct    23400
gggtgataga gtgaggctcg gtctaaaaaa aaaaaacaag gtgcagcctg tgtgtgattc    23460
ttaggttggt gatcttaggc aagatttaac ctctctatgg ttcagtttcc taatctgcaa    23520
aatggacgct atctcatagg gttactatgg agatcaaatg aggaattcac ataaagcact    23580
acagaaaata tttagcatgg aataagcact caataatgtt ttccattatt atttccaatt    23640
tttctctcag catgtgtttc acaatccttt gttcatggca aggtatgttg tccactttca    23700
ccctacacct tctaccgagc aacttaggtt tatccagtat cctcattagt aactttaatc    23760
cttaatgtca ctcacctttg aaatgtgctc attggacggg tgccacacag agcaagctcg    23820
caataaatgt tgctgaataa aacttactga ctgccactga cttaacttcg tttggatgtt    23880
gtttatagtc tctttatgcc tctgccaccc cagcagagtc ataaagaacc agacagaagc    23940
aggacccaag aacatgaggc ccaaaggaga gctgtgggaa gtgaaatact atattcaggg    24000
agaccctcag ctccttccca tctcagttcc ccaaatgaga gcaagcaggc tgatacttct    24060
caggtggggt atggagatat cccacctgat ccctcttgtc agttgataag ctggactcca    24120
catagcttat agtcagcttt ttggtgcttc actcttaaat atgaatgact agacaaagat    24180
caattgtcat ttgtaaaaaa aaaaaaaaa aaaaaaaact cttcaaaatg aaagacagaa    24240
ccaaaacaat cagaggaaaa gaacttgtag aaaacaggaa cgatgcaggg aatagaagag    24300
actatttttt aaaacttgta attattatct tttgagatta aagagaagat aaggcctcca    24360
tgaaacaaga acaaatgctg taaatcaagg aacattcaga gaacaacaag gacatttgga    24420
aataaaaaat atgtaaatac atttgcagaa aaacatggac aaatcttaaa gatatgttaa    24480
atacaataag tcagacatga aagaatacat actatactgt accatttata caacattcaa    24540
ggacagacaa aactaatcta tagtaacaga aatcaaaaag tgtttgcctg agaagtggcg    24600
aggactgact ggcaagggc acaagggaac tttctggaca gacagaaatg ttttatatct    24660
tgtttgggtg gtatttatga gggcgtattt aattattaaa attcattgag ctgaatgtct    24720
aagaactgta cacgttattg tatattaatt atgtatcaat aaaatcatat tgcaaaact     24780
gaaaagttaa gtagaagaat taagccacta tgtctagcca tcagtttaca agaaannnnn    24840
nnnnnnnnnn nnnnnnnnnn nnnnnnnnnn nnnnnnnnnn nnnnnnnnnn nnnnnnnnnn    24900
nnnnnnnnnn nnnnnnnnnn nnnnnnnnnn nnnnnnnnnn nnnnnnnnnn nnnnnnnnnn    24960
nnnnnnnnnn nnnnnnnnnn nnnnnnnnnn nnnnnnnnnn nnnnnnnnnn nnnnnnnnnn    25020
nnnnnnnnnt ggggaaaaaa gacagaggag gagcctataa aagagattta agagccaatc    25080
attgtatgaa ccacatttga tccaaattta aacaaaagtt taatgattgt ttaaatgatt    25140
gtatgattta agtttaaatt ttacttttaa agtttatag gacagttggt atacaaatat    25200
gtccagataa tattaaataa ttattcttat tttttaaatg agataatgtt attgtagtgc    25260
tttgttttag tgtgttttct aagtgacctt atcttttaga gattcatagt gaatacaaa     25320
tgatgcatga ctagaatagt caggagaagt gggaagggac atagatgaga caatattggc    25380
catgtgtggg taattgttga agccaggtga agactacttt gggtttatta ttctgcctct    25440
gttttgtata tatttgaagt ttcccataat aaaatacttt tttaaaaata gaagaattgg    25500
```

```
ggaaaaaaat gggggaagtt tcccccuatatg cccctcaaaa agaaataaga gacaagaatg  25560
gacattagga gcaaaaggta agaaacataa aggataagtt caatatttct gaaaaaaaga  25620
gaagagacaa aatgcaaggg agaaaatgat caaagaaata ctatgagagg ctggttgtgg  25680
tggctcatgc ctgtatccca gcactttgag aggccaaggc aggaggatcc cagaactagc  25740
ctgggaaaca gagagagacc ccgtctgtac caaagaaaaa aaaattaacc aggcatggtg  25800
gcatgcacct gtggttccag ctactcagga ggctgaagtg ggaagactgc ttgagcctag  25860
gaggtggaag ctgcagttag ccacgattga accactgcac ttccaacctg ggtgacagac  25920
tgaaactctc tttctctctt tctctgtcac acacacacac acacacacac acacacatag  25980
tgtgagataa tttcccagtg tagacagcca ttggtttctg gattgagggg ccagctgata  26040
gccatgatag ccatgatagc cagcaccgtg gatgaaaaaa gccccacatc aaagtatgtc  26100
cttgagaaat ttcatcatat tggtgtactg gaccacaaac ctcacatacc ttcctacatt  26160
ccctctactg cctccttttc tctccctctt ggacagttct ctgtcagcag catatccagg  26220
ctgcgttgcc cctccacttt cagagctgga taaaacatca tctggataaa acatcatcct  26280
gtggggtatg gagccttatt tcctgggcag ctgctaatca actggatgac atgtcggcaa  26340
tatagctctt cggataatcc ctgagcaatg gaaacgggag atgggaagga ctgggcagct  26400
gcatccccct catccactct ctcctgtgct tcctccttgt gcctcttcca gaagactccc  26460
ttgtgcctga tgaaccagca gccagctggg catcacatcc cccttccctc actctccttt  26520
tcccttctgc atattctatt ataaaatctt ccaagctag agcaaagttg aaagaatttc  26580
agaaagaatt tcagaaaaaa ttcagaaaga atttcacacg agcacctttg aaatacccat  26640
tacctagagt ttatcactga catttttaac agctttactg agatataatt taactactat  26700
aaaaaccatg catttaaagt gtactggctg ggcgcagtgg ctcacgcctg taatcccagc  26760
actttggaag ccaaagagg atggatcacc tgaggtcagg agtttaagac cagcctggcc  26820
aacatggtga aaccctgtct ctactgaaaa aaaaaaaaa aaaaagcca ggcgtggtgg  26880
tgcacgcctg tagtcccagc tattcaggag ctgaggcaga agaatcgctt gaaccggga  26940
ggtggaggct acagcgagcc aagatcacgc cactgcactc cagacggcga cagatgtctc  27000
aaaaaaaaaa attactggtt tttagtatat ttacagaggt gtgcaaacat taccacaatc  27060
aattttagaa cattttcttc accccaaaaa gaaatcccat atccttcagc agtcacttcc  27120
attacactgc tcttccaccc ctaagcaacc attcatctat tttctgtctc tatggaattg  27180
cctatattag acaccctgta taaatggaat catgtaatac atggtcattt gtgactagct  27240
tcttccattt agcatgtttt caaggttcac gaagcatgta tcagtacttc attcctttct  27300
tcccctctct ccctccccc aagacggagt cttgctgtgt cattcaggct ggggtgcaat  27360
ggcaccatct cggctcactg caacctctgc ctcccaggtt caagcgattc tcctgtctca  27420
gcctcccaag tagctgggat tacaggcacg cccagctatt ttttgtattt ttagtagaga  27480
cgggttttca ccatgttgac caggctggtc tcaactcctg atctcatgat ccgcccgcct  27540
cagcctcaca aagtgctggg attacaggca tgagccacca cctgccggct agtacttcat  27600
tcctttctat ggccaaataa tactcccttg tatatcatta acattttact agatttgctt  27660
tatcaaatgt ccatctatcc atcctctcta tccatccatg taatcaatct tacatctttt  27720
attttcgagt aaactcactt ctcttttttc caagcccttg caccttcagc ttgcacacct  27780
ctcaaataaa gctcatatca ctatcctgtg tgcaaaggag gctgggagag atgttgtctt  27840
tagtcatctg ggatttcgtg atagagggag gcaaaggaaa agggagactg ggaatagatt  27900
```

```
ctgctacctt agcatacagt ttctcaatcc catctcccct ccctccatgg catgccccaa   27960
atcatgtatt ctagaaacac caaattcctt aaagctccct caataccttg cactttttct   28020
gactccatct cttgcacatg ctcattacct ggatagcctt ctaggtgttt ccctcatatt   28080
cagccagctg tggctcttca gtgaagtatt ctcaacacac acacatac acacactcac      28140 ataacacaca catacacata cacacataca catacaggca ctcacacacg catacacacg    28200
ctcatacata cacacactca cacacatgca catatacaca cacatacaca tgcacagata    28260
cacacataca cacatgctct catatacaca tgcacattca cacatacact caccctcaca    28320
tacacataca tatgcacact cacatgcaca catacacaca tgctcacata cacgcacaca    28380
tacacacatg cacatacaaa catgctcaca tacactcaca tgcacacata cacatacacg    28440
ctctcataca catgctcaca tacactcaca tgcacattaa cacatacgca tgctcacaca    28500
cacatgcata ctcacacata cactcacata cacacataca caccacactc acatacacac    28560
acccactcgc acacacacat acactcacac acactcatac acccacacac gcatacaccc    28620
actcacacac actcatatgc ccacacacac acacacacac gcacatacac tcacatacac    28680
acacaatcac atacacacac aatcagatac acacacatgc acacactgac cccgtgggcc    28740
cccctgcgcg tgctccacac tctattgaat caaccttctg acctgtctgt ctctaccagt    28800
ctctaaatcc tcaagggcaa gggccaggcc ttacaggtct cggtatccct ggaactcatt    28860
gcagggcatg actcaacaaa tgttttctgc gtagtgaatg gaaaacatct agtcaccgtc    28920
tttgtcgtta tttatttaaa acatggcat gcaccaggtg aggccctgtg ataagtgcct     28980
ggatttggag acaaagatga gtaagactgt atcctgggcc tcagaggcgc ctacaggacc    29040
cttttgtctg gacaaatgca aaactggaca agacgccagg gcaacagatg taaaccggga    29100
ctgtcccaag caaaccggaa catatggtca cccaaattat ataccagctt ctctgaaaac    29160
agcactgcca tgctgactca tgcacagccc gttagatcct agtcacttcc agaactttct    29220
tgttcaggcc aatcactctt cattagtact tggattattc atgttttttc ttgttgtgat    29280
ccatgtagaa attatccatg aaatttcata tttctaaagc attacattaa aaatactta    29340 agcaactaga aataaaacac ctaatgcaca gctcaacact ttctaatgtt ttcttcatag    29400
agacggggtc tcacaaagtt acccaggcta gagtgctgtg gctcgtctat cgcactacag    29460
cctcgaactc cttggctgaa gggatcctcc catttcagcc ttttgagtag ctgggactac    29520
aggcacacac cactgcatcc aacttttcca acctttcctg aagtactgaa atgcatagtt    29580
gtaatcagtg ggtgacaatc attacatata taaattcctt ggtattaaca atagactctg    29640
gtttatcatc ttattgatgg gcctttgggt gtttccagct cgtgaccatt ctgagttaat    29700
gaagttatga acatctcaat atagattcct ttttctttct tctgagtctc ttctttgagg    29760
tacatactcc acagttaaat aatctggttg aaagacagga acaatttgtt acctttcgtt    29820
tcccattgct ctctgtcata tcgctctctg aaaagtccga gtcggccagg cacggtggct    29880
cacatctgta atctcagcac tttgggaggc cgaggcggga ggatcacttg aggtcagggg    29940
ttcaagacca gcctggccaa catggtgaaa ccccatctcc acgaaaaata caaaaattag    30000
ccaggcgtgg tggcaggcgc ctgtaatgcc agctacctgg gaggctgagg caggagaacg    30060
gcttgaacct aggaggtaga ggttgcagtg agctgagatc aggaccctgc attccagcct    30120
gggtgacaca atgatactcc atctcaaaaa tatatatata tatatacaca cacacatata    30180
tatttgagta aatacatgta ttaaaatcaa tgcagccata aaaagacaat tattgcatga    30240
```

-continued

```
ttccacttat atgaggtacc tagagcagtc aaattcatag agagagaaag taaaatggtg    30300
gttgcctggc gttgagggga ggaagaatgg caagttgttt aatgagtgta aattatcggt    30360
tttgcaagat gagtagttct ggagattggt tgcacaacag tgagaatgta cttaacacta    30420
ctgaacttac actgcaaaat gatttagata gtaaatttta tggggtaatt taccatacac    30480
acaagtatat ataaatagat atgtcttata tatagaaata aatatgtatg tatatatann    30540
nnnnnnnnnn nnnnnnnnnn nnnnnnnnnn nnnnnnnnnn nnnnnnnnnn nnnnnnnnnn    30600
nnnnnnnnnn nnnnnnnnnn nnnnnnnnnn nnnnnnnnnn nnnnnnnnnn nnnnnnnnct    30660
caattaaaat gacagtgtta attattcagt gcagagacag gcagaggaga gcgatgttaa    30720
tgttattaca tagcacacag agtaagaaac atgatagact agacaacata tgaacattta    30780
atattagtaa taaagtgctc aaccttaaaa aatcaataat acatctaatt ttctattatc    30840
tgtgaaattt ttaaaaaagc agagcttagg ggatcttata gacatccact tgaactttc    30900
atcttaaaga tgaggtgatg agcctaagag aggtaacaga ttttcccaca tcaggagcag    30960
ctacggcttc ccttttcatg tgaccttagc caccaactct ttatctcatt ggccaaaacg    31020
ggtcgcatgg cctcccctgg ctgcacccaa agctgccggg aaagcagcac aaagaatagg    31080
ttagacacat tgccacccca aacaaattag ggttccctca acaagggaag aaaaggagaa    31140
tgtgtattag gtaggcagtc agcagtgtct gctacactca ccttagtgtc tttgttctgt    31200
gttgtcttgt tttttgtttg ggatgttaca ggctggaacc aatggttaca tggctcctga    31260
gatcctaatg gaaaaggtaa gttattccta tcctgtggac tggtttgcca tgggatgcag    31320
catttatgaa atggttgctg gacgaacacc attcaaagat tacaaggaaa aggtcagtaa    31380
agaggatctg aagcaaagaa ctctgcaaga cgaggtcaaa ttccagcatg ataacttcac    31440
agaggaagca aaagatattt gcaggctctt cttggctaag aaaccagagc aacgcttagg    31500
aagcaggtaa actagcatgt aacagagagg attgctgaca ccagtattgt ccacagggat    31560
taggagaata cttttgattt gtggcaaagt cttggaatta agtattatga ttttcttatt    31620
tttatttgca tattatatgg ttaaacattt ctaaatactt caaacactat tagcactttg    31680
ctatggaaca atttcccaag atgtattta agggaaaag tgaggtgcaa agcagcttgc    31740
gttaaaaaaa gaaaaagaa tacataattc aaatggttgt atagaatatt tcaaggaatt    31800
tataggattg gttatgtcag atgaagggaa attgggggct ggggatgggg atgcaaataa    31860
gaattttcac tgtatcacct tagtttcttt tgcatctgaa ccatgttgag taaataaatg    31920
tattaaaatc acatgcagcc ataaaacaaa acaaatatta catgattcca cttatatgag    31980
gtacctagag tagtcgaatt catagagaca gaaagtagaa ggccgggcag ggtggctcat    32040
gcctgtaatg ccagtacttt gggaggccga gtcaggtgga tcacgaggtc aggagttcaa    32100
gaccagcctg gccaagatgg tgaaacccca tctgtaataa aactacaaaa attagccggg    32160
ggcggtggca ggtgcctgta atcccaacta ctcgggaggc taaggcagga gaatcgcttg    32220
aacccaggga gcagaggttg cagtgagcca agatcaagcc actgcactcc agcctgggtg    32280
acagagtgaa actccatctc aaaaaaaag aagaaagta agtagaacgg cagtttcctg    32340
gggttaaggg gaggagaaat gggaagttgt ctaatgagta taaattttct gttttacaag    32400
atgaagagtt ctggagattg gttgcataac aacgtagtgt gaatgtactt aacactgtta    32460
cattatctat tcaaaaataa ttaaaacagg ctgggcacag tggctcacac tgtgagccag    32520
gcatggtggt tcacgccagc acttgggagg ttgaggtnnn nnnnnnnnn nnnnnnnnnn    32580
nnnnnnnnnn nnnnnnnnnn nnnnnnnnnn nnnnnnnnnn nnnnnnnnnn nnnnnnnnnn    32640
```

```
nnnnnnnnnn nnnnnnnnnn nnnnnnnnnn nnnnnnnnnn nnnnnnnnnn nnnnnnnnnn      32700
nnnnnnnnnn nnnnnnnnnn nnnnnnnnnn nnnnnnnnnn nnnnnnnnnn nnnnnnnnnn      32760
nnnnnnnnnn nnnnnnnnnn nnnnnnnnnn nnnnnnnnnn nnnnnnnnnn nnnnnnnnnn      32820
nnnnnnnnnn nnnnnnnnnn nnnnnnnnnn nnnnnnnnnn nnnnnnnnnn nnnnnnnnnn      32880
nnnnnnnnnn nnnnnnnnnn nnnnnnnnnn nnnnnnnnnn nnnnnnnnnn nnnnnnnnnn      32940
nnnnnnnnnn nnnnnnnnnn nnnnnnnnnn nnnnnnnnnn nnnnnnnnnn nnnnnnnnnn      33000
nnnnnnnnnn nnnnnnnnnn nnnnnnnnnn nnnnnnnnnn nnnnnnnnnn nnnnnnnnnn      33060
nnnnnnnnnn nnnnnnnnnn nnnnnnnnnn nnnnnnnnnn nnnnnnnnnn nnnnnnnnnn      33120
nnnnnnnnnn nnnnnnnnnn nnnnnnnnnn nnnnnnnnnn nnnnnnnnnn nnnnnnnnnn      33180
nnnnnnnnnn nnnnnnnnnn nnnnnnnnnn nnnnnnnnnn nnnnnnnnnn nnnnnnnnnn      33240
nnnnnnnnnn nnnnnnnnnn nnnnnnnnnn nnnnnnnnnn nnnnnnnnnn nnnnnnnnnn      33300
nnnnnnnnnn nnnnnnnnnn nnnnnnnnnn nnnnnnnnnn nnnnnnnnnn nnnnnnnnnn      33360
nnnnnnnnnn nnnnnnnnnn nnnnnnnnnn nnnnnnnnnn nnnnnnnnnn nnnnnnnnnn      33420
nnnnnnnnnn nnnnnnnnnn nnnnnnnnnn nnnnnnnnnn nnnnnnnnnn nnnnnnnnnn      33480
nnnnnnnnnn nnnnnnnnna gaaaagaatg ctacacactt tgtattgtta gaacatgtcc      33540
cattttgttt tgttaactct gtctcaggct gatcatctcc tttcttcaca gagaaaagtc      33600
tgatgatccc aggaaacatc atttctttaa acgatcaac tttcctcgcc tggaagctgg       33660
cctaattgaa cccccatttg tgccagaccc ttcagtggtt tatgccaaag acatcgctga      33720
aattgatgat ttctctgagg ttcgggggt ggaatttgat gacaaagata agcagttctt       33780
caaaaacttt gcgacaggtg ctgttcctat agcatggcag gaagaaatta tagaaacggg      33840
actgtttgag gaactgaatg accccaacag acctacgggt tgtgaggagg gtaattcatc      33900
caagtctggc gtgtgtttgt tattgtaaat tgctctcttt accagacagg cagcaggagt      33960
ctcggctgac ataatcctcg aatgttccac acgtggaaat ctgtggaatg agggctaatc      34020
agttaggagg gacatcacaa ccacaaaaca attcaaaaga caggcaagct cactactaga      34080
acacatttta ttttcttttt ctttcttcat aaagatgagt aaagtctcag ttttcactga      34140
gggcagggaa aaggaacact caggtttatt ttgataaact gaaagcatca gcctttacc       34200 atcatgtccc tgtgtattac gcaaagtcct aggaacagag aatggaactt tgtggtgtgc      34260
ccagaaaatg agcatttgca attcttagta aataatcatt ttagtttttc tttgtttata      34320 tcttttttc ccttcatctt tcttcgcttc tatacttata aaaaggattt tgaagctgga       34380
aacaaatgtt tctgacattc tccccctaaa aaggagtgga ttacaatatt ttggcaatgt      34440
tttaaatcac agaataattt tcaatttcag tgacagtttc ttttgcaatt ttgtggaaat      34500
aatttactat cataatgttg aagcatttta aacataaaca tccatgacat ctgtgaatta      34560
aagcattctg taaatttagt tgagtccttt aagtaatatg gtacaaattg cttcaacttg      34620
cactaccata tgccatcggt tcccaaactc tgctgaactt tggaatcatc tagggatctt      34680
ttaaaaaact aatgcctgat tcccatccat agacattctg atccccactc ccaggtatga      34740
gaacagcttg accatttaga atttcagaag ctccccaggt gattctaatg tgcagcagag      34800
tttggcaggc actgctgtgc acatttgaat gttattacat tcaatcttat tttggttgct      34860
caaaacttca atcatacatt ttgatggcaa cttttcaaat gtccccaaag catgtcattt      34920
tagtaattgc agtataaatg aaacaagaca gtctattcat cttatggctt ctcttgtcct      34980
```

-continued

```
tgcacacttt agtttctcac acgtatcttg ggagctcggt ctcttggcta tttcaagtcc    35040
tgaaggagac ctatgggctt agaaattgag ttgaacaggc caggtgcggt ggctcatgcc    35100
tgcaattcca gcactttggg aggccaaggc agatggatca tgaggtcagg ggctcaagac    35160
tagcctggcc aacatgttgt aaaccccgtc tctactaaaa atacaaaaat tagcccggtg    35220
tggtggtgca catctataat cccagttacc cgggagcctg aggcaggaga attgcttgaa    35280
cccaggaggc ggaggttgta gtgagccaag atcgcaacat tgcactccag gctgggcagc    35340
aagagcaaga ctctatctca aaaaaaaaca aaacaaaaca aaacaaaaaa aacagaaaag    35400
aaattgaatt gaaaaaatac taaccatcat ttcaagtggc tgcccagcca acactgtatg    35460
gtagaattag cacttctcaa aagcacagcc aaggtgagaa ttctacagct gcgaaaaaat    35520
atttgggata caaatataaa gctgagtgat attttttaaa aggatgtatg tgcacataat    35580
aaaatctaaa tttatcccag tggtaaaaaa aacctggctg aagtcagttt aaaagttttg    35640
tcccttgagt taaggattca agagctgcaa aagtgccggt caaaaaaatg ttggttaact    35700
ggaatctgaa taacagtaat actcatctac aagacagcat taaccacacc tggaacaagt    35760
taagaagaag ccctctgaga gttgaggcct cggccggtgc acctgcggct cactttcccg    35820
ctcctcctcc atcctcagca tgctccctaa tgctccaaat cctaacctag gatgcttaga    35880
tttctgtgtc accaaagcag gatagaagtg tgcccaggag attttttttt ttcctgaagt    35940
aagaaagtaa attaaagttt ggttaagttt tgaacaagtc ccttttaaca aaaaaactga    36000
ttggtgatta acagaaatcc aattaaccag agcactccaa tggtagagtt ctcaggattg    36060
ggctttatag acgttagaca tttaaaaaca acattggtta tttgttgatt atgccttaaa    36120
gctggcagag ggacaaatgc aaactaataa ttaaagataa atatctcagt ttttaaaagg    36180
acaaaaaatt tggagagata aaaaaataaa aatgtcttgt tgcattggtt ccttagtgtg    36240
aattgcctct gctttcaata aactttaaat gcaaatctgt tttatatctt agaactaact    36300
taggaaaata actgaataag tagttgtatt aatccattct cacactgcta taaagaaata    36360
cctgaggctg gcatggtgg ctcacgcctg caatcccagc actttgggag tccaaggcag    36420
gcagatcacc tgagattagg agtttgagac cagcctggcc aacatggtaa aatcctgtct    36480
ccactaaaaa tatacaaatt agccaggtgt ggtggtgtgt gcctataatc ccagctacta    36540
ggaaggctga gacaggagga ttgcttcaac ctgggaggag gaggttgcag tgagccgaga    36600
ttcagccact ggactccagc ctgggtgaca gagcaaggct ctgtctcaga a             36651
```

<210> SEQ ID NO 4
<211> LENGTH: 548
<212> TYPE: PRT
<213> ORGANISM: Spermophilus tridecemlineatus

<400> SEQUENCE: 4

```
Met Asp Met Gly Gly Leu Asp Asn Leu Ile Ala Asn Thr Ala Tyr Leu
 1               5                  10                  15

Gln Ala Arg Lys Thr Asp Ser Ser Arg Glu Leu Gln Arg Arg
            20                  25                  30

Arg Ser Leu Ala Leu Pro Gly Pro Gln Gly Cys Ala Glu Leu Arg Gln
        35                  40                  45

Ser Leu Ser Pro His Phe His Ser Leu Cys Glu Gln Gln Pro Ile Gly
    50                  55                  60

Arg Arg Leu Phe Arg Asp Phe Leu Ala Thr Val Pro Lys Tyr Ser Gln
65                  70                  75                  80
```

-continued

```
Ala Val Ala Phe Leu Glu Asp Val Gln Asn Trp Glu Leu Ala Glu Glu
                 85                  90                  95
Gly Pro Ala Lys Thr Ser Thr Leu Gln Gln Leu Ala Thr Cys Ala
            100                 105                 110
Arg Asp Pro Gly Pro Gln Ser Phe Leu Ser Gln Asp Leu Ala Thr Lys
            115                 120                 125
Cys Arg Ala Ala Ser Thr Asp Glu Glu Arg Lys Thr Leu Val Glu Gln
130                 135                 140
Ala Lys Ala Glu Thr Met Ser Phe Leu Gln Glu Gln Pro Phe Gln Asp
145                 150                 155                 160
Phe Leu Ala Ser Pro Phe Tyr Asp Arg Phe Leu Gln Trp Lys Leu Phe
                165                 170                 175
Glu Met Gln Pro Val Ser Asp Lys Tyr Phe Thr Glu Phe Arg Val Leu
                180                 185                 190
Gly Lys Gly Gly Phe Gly Glu Val Cys Ala Val Gln Val Arg Asn Thr
            195                 200                 205
Gly Lys Met Tyr Ala Cys Lys Lys Leu Asp Lys Lys Arg Leu Lys Lys
            210                 215                 220
Lys Gly Gly Glu Lys Met Ala Leu Leu Glu Lys Glu Ile Leu Glu Lys
225                 230                 235                 240
Val Asn Ser Pro Phe Ile Val Ser Leu Ala Tyr Ala Phe Glu Ser Lys
                245                 250                 255
Thr His Leu Cys Leu Val Met Ser Leu Met Asn Gly Gly Asp Leu Lys
            260                 265                 270
Phe His Ile Tyr Asn Val Gly Thr Arg Gly Leu Ala Met Ser Arg Val
            275                 280                 285
Ile Phe Tyr Thr Ala Gln Met Thr Cys Gly Val Leu His Leu His Gly
            290                 295                 300
Leu Gly Ile Val Tyr Arg Asp Leu Lys Pro Glu Asn Val Leu Leu Asp
305                 310                 315                 320
Asp Leu Gly Asn Cys Arg Leu Ser Asp Leu Gly Leu Ala Val Glu Val
                325                 330                 335
Gln Asp Asp Lys Pro Ile Thr Gln Arg Ala Gly Thr Asn Gly Tyr Met
                340                 345                 350
Ala Pro Glu Ile Leu Met Asp Lys Ala Ser Tyr Ser Tyr Pro Val Asp
            355                 360                 365
Trp Phe Ala Met Gly Cys Ser Ile Tyr Glu Met Val Ala Gly Arg Thr
370                 375                 380
Pro Phe Lys Asp Phe Lys Glu Lys Val Ser Lys Glu Asp Leu Lys Glu
385                 390                 395                 400
Arg Thr Met Lys Asp Glu Val Ala Phe His Glu Asn Phe Thr Glu
                405                 410                 415
Glu Thr Lys Asp Ile Cys Arg Leu Phe Leu Ala Lys Lys Pro Glu Gln
            420                 425                 430
Arg Leu Gly Ser Arg Glu Lys Ala Asp Asp Pro Arg Lys His Pro Phe
            435                 440                 445
Phe Gln Thr Val Asn Phe Pro Arg Leu Glu Ala Gly Leu Val Glu Pro
    450                 455                 460
Pro Phe Val Pro Asp Pro Ser Val Val Tyr Ala Lys Asp Val Asp Glu
465                 470                 475                 480
Ile Asp Asp Phe Ser Glu Val Arg Gly Val Glu Phe Asp Asp Lys Asp
                485                 490                 495
Lys Gln Phe Phe Gln Arg Phe Ser Thr Gly Ala Val Pro Val Ala Trp
```

```
                    500                 505                 510
Gln Glu Glu Ile Ile Glu Thr Gly Leu Phe Glu Glu Leu Asn Asp Pro
        515                 520                 525

Asn Arg Pro Ser Gly Asp Gly Lys Gly Asp Ser Ser Lys Ser Gly Val
    530                 535                 540

Cys Leu Leu Leu
545
```